(12) United States Patent
Crowe, Jr. et al.

(10) Patent No.: US 11,524,994 B2
(45) Date of Patent: Dec. 13, 2022

(54) ANTIBODIES TO HUMAN RESPIRATORY SYNCYTIAL VIRUS PROTEIN F PRE-FUSION CONFORMATION AND METHODS OF USE THEREFOR

(71) Applicant: Vanderbilt University, Nashville, TN (US)

(72) Inventors: James E. Crowe, Jr., Nashville, TN (US); Jarrod Mousa, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 650 days.

(21) Appl. No.: 16/470,604

(22) PCT Filed: Dec. 18, 2017

(86) PCT No.: PCT/US2017/066963
§ 371 (c)(1),
(2) Date: Jun. 18, 2019

(87) PCT Pub. No.: WO2018/118754
PCT Pub. Date: Jun. 28, 2018

(65) Prior Publication Data
US 2019/0367586 A1    Dec. 5, 2019

Related U.S. Application Data

(60) Provisional application No. 62/436,017, filed on Dec. 19, 2016.

(51) Int. Cl.
*C07K 16/10* (2006.01)
*G01N 33/569* (2006.01)

(52) U.S. Cl.
CPC ... *C07K 16/1027* (2013.01); *G01N 33/56983* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/622* (2013.01)

(58) Field of Classification Search
None
See application file for complete search history.

(56) References Cited

U.S. PATENT DOCUMENTS 9,856,313 B2 *   1/2018  Zheng ................. A61K 31/7084
2009/0035322 A1  2/2009  Martin et al.
2016/0031972 A1  2/2016  Zheng et al.

OTHER PUBLICATIONS

Anderson, Larry J., et al. "Antigenic characterization of respiratory syncytial virus strains with monoclonal antibodies." *Journal of Infectious Diseases* 151.4 (1985): 626-633.

Boyington, Jeffrey C., et al. "Structure-based design of head-only fusion glycoprotein immunogens for respiratory syncytial virus." *PLoS One* 11.7 (2016): e0159709.
Extended European Search Report issued in European Application No. 17885369.3, dated Jul. 9, 2020.
Gilman, Morgan SA, et al. "Characterization of a prefusion-specific antibody that recognizes a quaternary, cleavage-dependent epitope on the RSV fusion glycoprotein." *PLoS pathogens* 11.7 (2015): e1005035.
IMpact-RSV Study Group. "Palivizumab, a humanized respiratory syncytial virus monoclonal antibody, reduces hospitalization from respiratory syncytial virus infection in high-risk infants." *Pediatrics* 102.3 (1998): 531-537.
International Preliminary Report on Patentability issued in International Application No. PCT/US2017/066963, dated Jul. 4, 2019.
International Search Report and Written Opinion issued in International Application No. PCT/US2017/066963, dated May 9, 2018.
Invitation to Pay Additional Fees issued in International Application No. PCT/US2017/066963, dated Mar. 13, 2018.
Lopez, Juan A., et al. "Antigenic structure of human respiratory syncytial virus fusion glycoprotein," *Journal of virology* 72.8 (1998): 6922-6928.
McLellan, Jason S., "Neutralizing epitopes on the respiratory syncytial virus fusion glycoprotein." *Current opinion in virology* 11 (2015): 70-75.
McLellan, Jason S., et al. "Structure of respiratory syncytial virus fusion glycoprotein in the postfusion conformation reveals preservation of neutralizing epitopes." *Journal of Virology* 85.15 (2011): 7788-7796.
McLellan, Jason S., et al., "Structure-based design of a fusion glycoprotein vaccine for respiratory syncytial virus," *science* 342. 6158 (2013): 592-598.
Mousa, Jarrod J., et al. "A novel pre-fusion conformation-specific neutralizing epitope on the respiratory syncytial virus fusion protein." *Nature Microbiology* 2.4 (2017): 1-8.
Mousa, Jarrod J., et al. "Structural basis for nonneutralizing antibody competition at antigenic site II of the respiratory syncytial virus fusion protein." *Proceedings of the National Academy of Sciences* 113.44 (2016): E6849-E6858.
Ngwuta, Joan O., et al. "Prefusion F-specific antibodies determine the magnitude of RSV neutralizing activity in human sera." *Science translational medicine* 7.309 (2015): 309ra162-309ra162.
Rossey, Iebe, et al., "Potent single-domain antibodies that arrest respiratory syncytial virus fusion protein in its prefusion state." *Nature communications* 8.1 (2017): 1-12.
Widjaja, Ivy, et al. "Characterization of epitope-specific antirespiratory syncytial virus (anti-RSV) antibody responses after natural infection and after vaccination with formalin-inactivated RSV." *Journal of Virology* 90.13 (2016): 5965-5977.
Wu, Herren, et al. "Development of motavizumab, an ultra-potent antibody for the prevention of respiratory syncytial virus infection in the tipper and lower respiratory tract." *Journal of molecular biology* 368.3 (2007b): 652-665.
Wu, Sheng-Jiun, et al., "Characterization of the epitope for antihuman respiratory syncytial virus F protein monoclonal antibody 101F using synthetic peptides and genetic approaches." *Journal of General Virology* 88.10 (2007a): 2719-2723.

* cited by examiner

*Primary Examiner* — Agnieszka Boesen
(74) *Attorney, Agent, or Firm* — Parker Highlander PLLC

(57) ABSTRACT

The present disclosure is directed to antibodies binding to human respiratory syncytial virus F protein, including both neutralizing and non-neutralizing antibodies, and methods for use thereof.

13 Claims, 32 Drawing Sheets

Specification includes a Sequence Listing.

| | | | | | | | | | | | | | | | | | | |
|---|---|---|---|---|---|---|---|---|---|---|---|---|---|---|---|---|---|---|
| II | 131 | 133 | 92 | 157 | 94 | 40 | 14 | 7 | 10 | 2 | 4 | 4 | 3 | 8 | 0 | 3 | 63 | 30 |
| | 75 | 68 | 93 | 58 | 85 | 3 | 3 | 1 | 2 | 1 | 2 | 1 | 0 | 2 | 0 | 4 | 105 | 3 |
| | PVZ | 22 | 17 | 48 | 81 | 8 | 6 | 8 | 8 | 9 | 9 | 11 | 17 | 12 | 2 | 13 | 76 | 85 |
| | MVZ | 5 | 6 | 79 | 71 | 34 | 54 | 3 | 2 | 9 | 4 | [66] | 4 | 1 | 2 | 1 | 76 | 104 |
| IV | AM14 | 42 | 63 | -2 | 72 | 85 | 53 | 16 | 9 | 24 | 18 | 27 | 52 | [96] | 53 | 73 | -2 | 2 |
| | 101F | 95 | 89 | 116 | 104 | 84 | 81 | 82 | 83 | 90 | 88 | 113 | 80 | 52 | 43 | 87 | 106 | 8 |

FIG. 2B

*Coomassie-stained SDS-PAGE*

*Anti-polyhistidine-alkaline phosphatase antibody
BM purple chromogenic substrate*

FIG. 12

ANTIBODIES TO HUMAN RESPIRATORY SYNCYTIAL VIRUS PROTEIN F PRE-FUSION CONFORMATION AND METHODS OF USE THEREFOR

This application is a national phase application under 35 U.S.C. § 371 of International Application No. PCT/US2017/066963, filed Dec. 18, 2017, which claims benefit of priority to U.S. Provisional Application Ser. No. 62/436,017, filed Dec. 19, 2016, the entire contents of each of which are hereby incorporated by reference.

This invention was made with government support under grant nos. S10 RR026915 and T32 AI 07474 awarded by the National Institutes of Health. The government has certain rights in the invention.

BACKGROUND

1. Field of the Disclosure

The present disclosure relates generally to the fields of medicine, infectious disease, and immunology. More particular, the disclosure relates to human antibodies binding to respiratory syncytial virus (RSV).

2. Background

RSV expresses three surface proteins, the attachment (G), small hydrophobic (SH), and fusion (F) proteins. The G and F glycoproteins are the targets of neutralizing antibodies. While the RSV G protein does induce neutralizing antibodies, antigenic diversity in G proteins among RSV strains makes it difficult to design a broadly protective vaccine candidate based on immunogenicity to this protein. Although there is no licensed RSV vaccine, a prophylactic monoclonal antibody (mAb), palivizumab (Group et al., 1998) (Synagis; MedImmune), is available for prophylactic treatment of high-risk infants, yet the high cost and moderate efficacy limit its use. The F protein is a class I fusion glycoprotein that adopts two conformations during viral infection. The pre-fusion F conformation is meta-stable and is triggered easily to the post-fusion conformation, resulting in a dramatic change involving the formation of a 6-helix bundle extending the hydrophobic fusion peptide into the host cell membrane (Smith et al., 2009). Recent structural breakthroughs in X-ray crystallography have provided atomic-resolution detail of the post-fusion and pre-fusion F conformations (McLellan et al., 2011; 2013a). Furthermore, structure-based designed of the F protein has resulted in stabilized F constructs (DsCav1 and SC-TM) that retain components of the pre-fusion F conformation and induce neutralizing antibody immune responses (McLellan et al., 2013b; Krarup et al., 2015). Four major neutralizing antigenic sites have been reported previously, recognized by the representative mAbs 131-2a (Anderson et al., 1985) (site I), palivizumab (Group et al., 1998) and motavizumab (Wu et al., 2007a) (site II), 101F (Wu et al., 2007b) (site IV), 7.936 (Lopez et al., 1998) (site V, near amino acid 447), 7.916 and 9.432 (Lopez et al., 1998) (site VI, near amino acid 432), and the recently discovered pre-fusion specific mAb D25 (McLellan et al., 2013b) (site 0). Furthermore, a quaternary-dependent pre-fusion-specific epitope has been described using mAb AM14 (Gilman et al., 2015). Antigenic sites II and IV-VI are retained in both the pre- and post-fusion conformations of F (McLellan et al., 2015), evidenced by the X-ray structures having exposed epitopes at these sites in both conformations. Antigenic site I is present in the post-fusion conformation, while site Ø is pre-fusion specific, as the conformational epitope is lost in the post-fusion rearrangement.

The inventors recently described the isolation and characterization of several new human mAbs targeting antigenic sites I and II, which were identified by screening for binding to the RSV strain A2 F protein in the post-fusion conformation (Mousa et al., 2016). Several site II mAbs were described that are potently neutralizing, including clones with binding poses on site II that differ from that of palivizumab and exhibit distinct functional patterns. While site II is the target of palivizumab and the second-generation mAb motavizumab, and has been shown to induce potently neutralizing mAbs, antigenic site II may not be the optimal antigenic site to induce protective mAbs against RSV infection. Non-neutralizing mAbs that recognize a nearby newly recognized antigenic site (site VII centered near amino acid Leu467) compete for binding at antigenic site II, particularly in the context of the post-fusion conformation (Mousa et al., 2016). These data suggest non-neutralizing post-fusion RSV F mAbs may interfere with the binding and protective effect of site II-specific neutralizing mAbs. Recent experiments suggested a dominant role for epitopes in the pre-fusion conformation of RSV F in induction of serum neutralizing antibodies, particularly a major role for antigenic site Ø in immunogenicity (Ngwuta et al., 2015). However, while site Ø-specific mAbs are indeed among the most potently neutralizing, very few human mAbs to this site have been isolated and characterized.

SUMMARY

Thus, in accordance with the present disclosure, there is provided a method of detecting a human respiratory syncytial virus infection in a subject comprising (a) contacting a sample from said subject with an antibody or antibody fragment having clone-paired heavy and light chain CDR sequences from Tables 3 and 4, respectively; and (b) detecting human respiratory syncytial virus in said sample by binding of said antibody or antibody fragment to a Human respiratory syncytial virus antigen in said sample. The sample may be a body fluid, such as blood, sputum, tears, saliva, mucous or serum, urine, exudate, transudate, tissue scrapings or feces. Detection may comprise ELISA, RIA or Western blot. The method may further comprise performing steps (a) and (b) a second time and determining a change in human respiratory syncytial virus antigen levels as compared to the first assay. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be is a recombinant scFv (single chain fragment variable) antibody, Fab fragment, F(ab')$_2$ fragment, or Fv fragment.

In another embodiment, there is provided a method of treating a subject infected with human respiratory syncytial virus, or reducing the likelihood of infection of a subject at risk of contracting human respiratory syncytial virus, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be is a recombinant scFv (single chain fragment variable) antibody, Fab fragment, F(ab')$_2$ fragment, or Fv fragment.

The antibody or antibody fragment may recognize an epitope on pre-fusion RSV F protein in antigenic site VIII, and optionally is specific for an epitope on pre-fusion RSV F protein in antigenic site VIII. The antibody or antibody fragment may neutralize RSV A and B subgroups, and/or bind to metapneumovirus fusion protein. The antibody or antibody fragment may be administered prior to infection, or after infection. Delivering may comprise antibody or antibody fragment administration, or genetic delivery with an RNA or DNA sequence or vector encoding the antibody or antibody fragment.

In yet another embodiment, there is a provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be is a recombinant scFv (single chain fragment variable) antibody, Fab fragment, F(ab')$_2$ fragment, or Fv fragment. The antibody may be a chimeric antibody, a bispecific antibody, and/or is an IgG. The antibody or antibody fragment may recognize an epitope on pre-fusion RSV F protein in antigenic site VIII, and optionally is specific for an epitope on pre-fusion RSV F protein in antigenic site VIII, and/or neutralizes RSV A and B subgroups, and/or may bind to metapneumovirus fusion protein. The antibody or antibody fragment may further comprise a cell penetrating peptide and/or is an intrabody.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be is a recombinant scFv (single chain fragment variable) antibody, Fab fragment, F(ab') 2 fragment, or Fv fragment. The antibody may be a chimeric antibody, a bispecific antibody, and/or is an IgG. The antibody or antibody fragment may recognize an epitope on pre-fusion RSV F protein in antigenic site VIII, and optionally may be specific for an epitope on pre-fusion RSV F protein in antigenic site VIII, and/or neutralizes RSV A and B subgroups, and/or may bind to metapneumovirus fusion protein. The antibody or antibody fragment may further comprise a cell penetrating peptide and/or is an intrabody.

A further embodiment comprises a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be is a recombinant scFv (single chain fragment variable) antibody, Fab fragment, F(ab')$_2$ fragment, or Fv fragment. At least one of said antibodies may be a chimeric antibody, is bispecific antibody, and/or is an IgG. At least of said antibodies or antibody fragments may recognize an epitope on pre-fusion RSV F protein in antigenic site VIII, and optionally may be specific for an epitope on pre-fusion RSV F protein in antigenic site VIII, and/or may neutralize RSV A and B subgroups, and/or may bind to metapneumovirus fusion protein. A least one of said antibodies or antibody fragments may further comprise a cell penetrating peptide and/or is an intrabody.

An additional embodiment comprises a method of identifying an anti-human respiratory syncytial virus (hRSV) protein F site VIII-specific neutralizing monoclonal antibody or polyclonal serum comprising (a) contacting a candidate antibody or serum with hRSV protein F in the presence of a known site VIII-specific neutralizing antibody or antigen binding fragment thereof; (b) assessing binding of said candidate antibody or serum to hRSV protein F; and (c) identifying said candidate antibody or serum as a protein F siteVIII-specific neutralizing antibody when said known site VIII-specific neutralizing antibody or antigen binding fragment thereof blocks binding of said candidate antibody or serum to hRSV protein F. The method may further comprise performing a control reaction where said candidate antibody or serum is contacted with hRSV protein F in the absence of a known site VIII-specific neutralizing antibody or fragment thereof. Detection may comprise ELISA, RIA or Western blot. The known site VIII-specific neutralizing antibody or fragment thereof may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The known site VIII-specific neutralizing antibody or fragment thereof may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment.

Other embodiments include (i) a monoclonal antibody or fragment thereof, wherein said antibody or fragment thereof recognizes an epitope on pre-fusion RSV F protein in antigenic site VIII, such as where said antibody or antibody fragment is specific for an epitope on pre-fusion RSV F protein in antigenic site VIII, (ii) a monoclonal antibody or fragment thereof, wherein said antibody or antibody fragment recognizes an epitope on pre-fusion RSV F protein in antigenic site VIII and neutralizes RSV A and B subgroups, and (iii) a monoclonal antibody or fragment thereof, wherein said antibody or antibody fragment recognizes an epitope on pre-fusion RSV F protein in antigenic site VIII and binds to metapneumovirus fusion protein.

In still another embodiment, there is provided a method of identifying the presence of human respiratory syncytial virus (hRSV) protein F site VIII protective antigen in a vaccine or virus preparation using human respiratory syncytial virus (hRSV) protein F site VIII-specific monoclonal or polyclonal neutralizing antibodies comprising (a) contacting a candidate vaccine or virus composition with a known site VIII-specific neutralizing antibody or antigen binding fragment thereof; (b) assessing binding of said candidate vaccine or virus composition to a known site VIII-specific neutralizing antibody or antigen binding fragment; and (c) identifying said candidate vaccine or virus composition as containing the protein F site VIII protective epitope when one or more known site VIII-specific neutralizing antibodies bind to the candidate vaccine or virus composition.

Also provided is a method of determining the antigenic integrity of an antigen comprising (a) contacting a sample comprising said antigen with a first antibody or antibody fragment having clone-paired heavy and light chain CDR sequences from Tables 3 and 4, respectively; and (b) determining antigenic integrity of said antigen by detectable binding of said antibody or antibody fragment to said antigen. The sample may comprise recombinantly produced antigen. The sample may comprise a vaccine formulation or vaccine production batch. The detection may comprise ELISA, RIA, western blot, a biosensor using surface plasmon resonance or biolayer interferometry, or flow cytometric staining. The first antibody or antibody fragment may be encoded by clone-paired variable sequences as set forth in Table 1. The first antibody or antibody fragment may be encoded by light and heavy chain variable sequences having 70%, 80%, or 90% identity to clone-paired variable sequences as set forth in Table 1. The first antibody or antibody fragment may be encoded by light and heavy chain variable sequences having 95% identity to clone-paired sequences as set forth in Table 1. The first antibody or antibody fragment may comprise light and heavy chain variable sequences according to clone-paired sequences from Table 2. The first antibody or antibody fragment may comprise light and heavy chain variable sequences having 70%, 80% or 90% identity to clone-paired sequences from Table 2. The first antibody or antibody fragment may comprise light and heavy chain variable sequences having 95% identity to clone-paired sequences from Table 2. The first antibody fragment may be a recombinant ScFv (single chain fragment variable) antibody, Fab fragment, F(ab')$_2$ fragment, or Fv fragment. The method may further comprise steps (a) and (b) a second time to determine the antigenic stability of the antigen over time. The method may further comprise (c) contacting a sample comprising said antigen with an antibody or antibody fragment having clone-paired heavy and light chain CDR sequences from Tables 3 and 4, respectively; and (d) determining antigenic integrity of said antigen by detectable binding of said antibody or antibody fragment to said antigen. The second antibody or antibody fragment may be encoded by clone-paired variable sequences as set forth in Table 1. The second antibody or antibody fragment may be encoded by light and heavy chain variable sequences having 70%, 80%, or 90% identity to clone-paired variable sequences as set forth in Table 1. The second antibody or antibody fragment may be encoded by light and heavy chain variable sequences having 95% identity to clone-paired sequences as set forth in Table 1. The second antibody or antibody fragment may comprise light and heavy chain variable sequences according to clone-paired sequences from Table 2. The second antibody or antibody fragment may comprise light and heavy chain variable sequences having 70%, 80% or 90% identity to clone-paired sequences from Table 2. The second antibody or antibody fragment may comprise light and heavy chain variable sequences having 95% identity to clone-paired sequences from Table 2. The second antibody fragment may be a recombinant ScFv (single chain fragment variable) antibody, Fab fragment, F(ab')$_2$ fragment, or Fv fragment. The method may further comprise steps (c) and (d) a second time to determine the antigenic stability of the antigen over time.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1. Epitope binning for select RSV F specific mAbs. Data indicate the percent binding of the competing antibody in the presence of the primary antibody, as compared to the second antibody alone. Cells filled in black indicate full competition, in which <33% of the un-competed signal was observed, intermediate competition (grey) if signal was between 33-66%, and non-competing (white) if signal was ≥66%. Antigenic sites are highlighted at the top and side based on competition-binding with the control mAbs D25 (site Ø), palivizumab (PVZ) or motavizumab (MVZ) (site II), or 101F (site IV). Those colored in yellow are encoded by $V_H3-9*01$, and those in light blue are encoded by $V_H1-8*01$. Competition for binding with D25 and palivizumab/motavizumab revealed a novel antigenic site VIII bound by antibodies that compete with both mAbs specific for site Ø or mAb specific for site II. The site VIII competition-binding group is indicated by a green border.

FIGS. 2A-B. X-ray crystal structure of hRSV90-RSV F SC-TM complex. (FIG. 2A) Overall structure of the hRSV90-RSV F trimer. Antigenic sites are labeled with site IV in red, site II in orange, and site Ø in blue. hRSV90 Fab (magenta) binds at a unique site between antigenic sites II and Ø. The structure is turned 90° and shown looking down at the viral membrane. One protomer is shown as a cartoon in each representation, where the RSV F is colored green. (FIG. 2B) Overall interactions between hRSV90 and prefusion RSV F. hRSV90 binds at two clefts around the newly identified antigenic site VIII (green). The heavy chain is close to site Ø (blue), while the light chain is close to site II (orange). The unique features of Site VIII comprise residues 163-181 of the RSV F protein. The structure is turned 180° to show both sides of the Fab-RSV F interaction.

(FIG. 3A) Known X-ray structures are superimposed upon the hRSV90-RSV F structure to compare antigenic sites. MAb AM14 (PDB: 4ZYP) and mAb D25 (PDB: 4JHW) were overlaid at RSV F, motavizumab (PDB: 3IXT) was overlaid at the site II peptide, and mAb 101F (PDB: 3041) was overlaid at the site IV peptide. The structure is turned 90° to show the comparison looking down on the viral membrane. hRSV90 overlaps with mAbs at sites II and Ø. (FIG. 3B) Specific interactions between the hRSV90 heavy chain and RSV F are shown. hRSV90 is shown in purple, antigenic site VIII in green, site II in orange, and site Ø in blue, while the RSV F protein is colored cyan. The heavy chain CDR3 mediates binding to site VIII and site Ø. (FIG. 3C) Interactions between the hRSV90 light chain and RSV F. The colors are the same as in (b). The hRSV90 light chain mediates binding to antigenic site VIII and II.

(FIG. 6A) Gating strategy for measuring binding of mAb to Jurkat cells. (FIG. 6B) Representative flow cytometry histograms showing dose-dependent binding of antigen-specific, self-reactive, or hRSV90 mAbs to Jurkat cells. Binding of BDBV289 Ebola virus GP-specific mAb to transfected Jurkat cells that express Ebola virus GP on their surface served as positive control for antigen-specific mAb (orange histogram); a mAb with known self-reactivity (BDBV223) served as a control for self-reactivity (light blue histogram); Jurkat stained with secondary detection PE-conjugated Ab only served as a control for assay background (red histogram). (FIG. 6C) Dose-dependent binding of hRSV mAbs to Jurkat cells measured as mean fluorescence intensity (MFI). Data represent mean±SD of two experiments.

(FIG. 7A) $2F_o-2F_c$ density map. (FIG. 7B) Simulated annealing composite omit density map of the same interface. (FIG. 7C) $2F_o-2F_c$ Density map of the entire structure showing density for the fold-on trimerization domain.

(FIG. 8A) Structural regions of the RSV F protein are shown with corresponding labels in both pre-fusion and post-fusion structures. HRA is heptad repeat A (red as part of DIII), HRB is heptad repeat B (blue as part of DII), FP is fusion peptide (green), and DI is shown in yellow. (FIG. 8B) Antigenic regions in the pre-fusion and post-fusion RSV F structures are colored. Site IV is red, site II is orange, site Ø is blue, and site VIII is magenta. Residues comprising antigenic sites Ø and VIII are rearranged in the post-fusion conformation, resulting in loss of mAb binding. Site VIII becomes part of the six-helix bundle of the post-fusion RSV F protein.

(FIG. 9A) A Coomassie-stained SDS-PAGE is displayed with bands displayed for each purified mutant protein. (FIG. 9B) A corresponding western blot is shown using a monoclonal anti-polyhistidine-alkaline phosphatase antibody with BM purple chromogenic substrate to visualize the RSV F mutants directly on the PVDF membrane.

Figure 12:
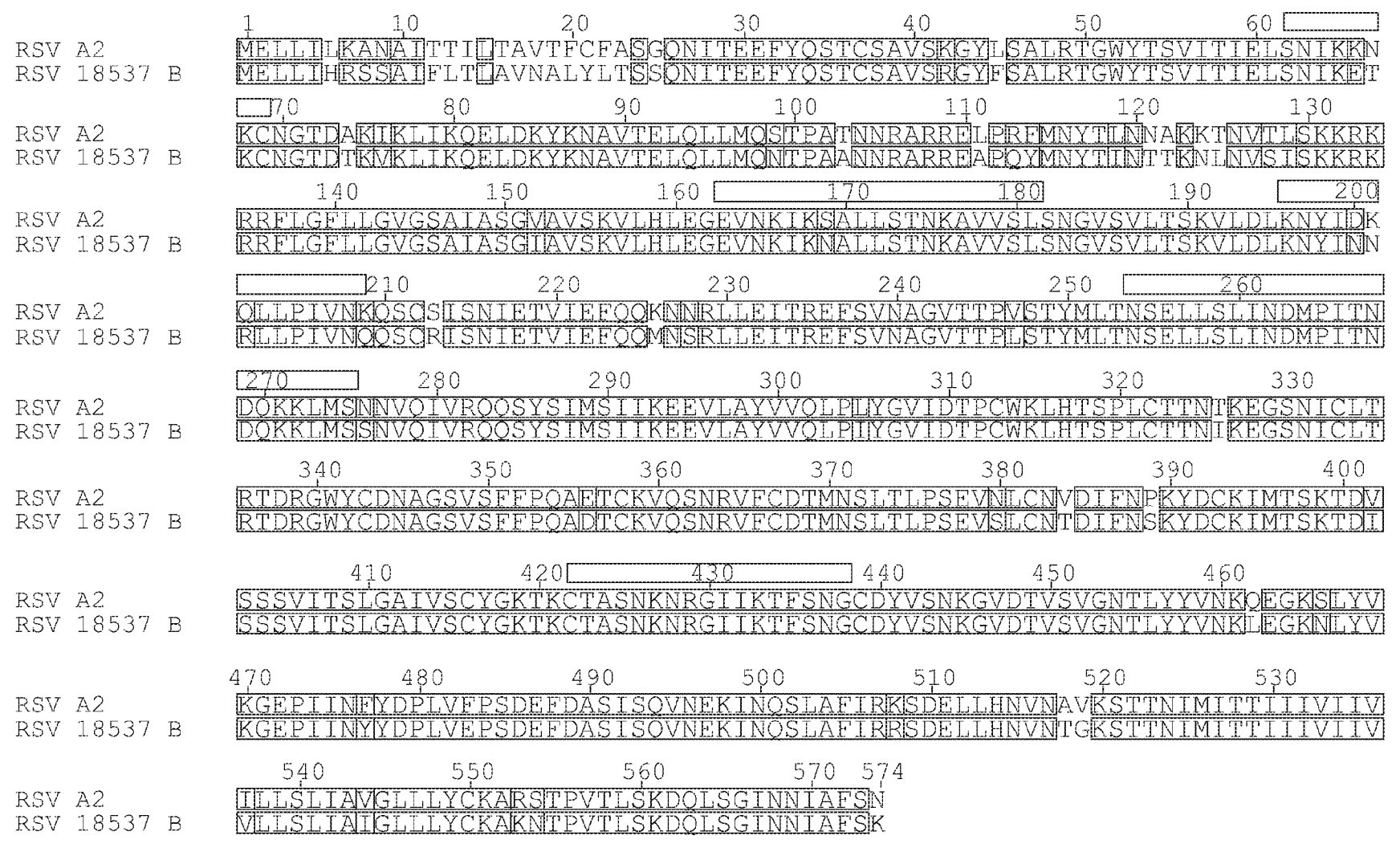

FIG. 12. Alignment of RSV F proteins from subgroups A and B. Amino acids in green are conserved among the two proteins, those in light green are semi-conserved, and those in white are not conserved. Antigenic sites are shaded above the corresponding sequences, with site Ø in blue, site VIII in magenta, site II in orange, and site IV in red. (subgroup A, upper=SEQ ID NO: 147; subgroup B, lower=SEQ ID NO: 148)

DESCRIPTION OF ILLUSTRATIVE EMBODIMENTS

Figure 2A:
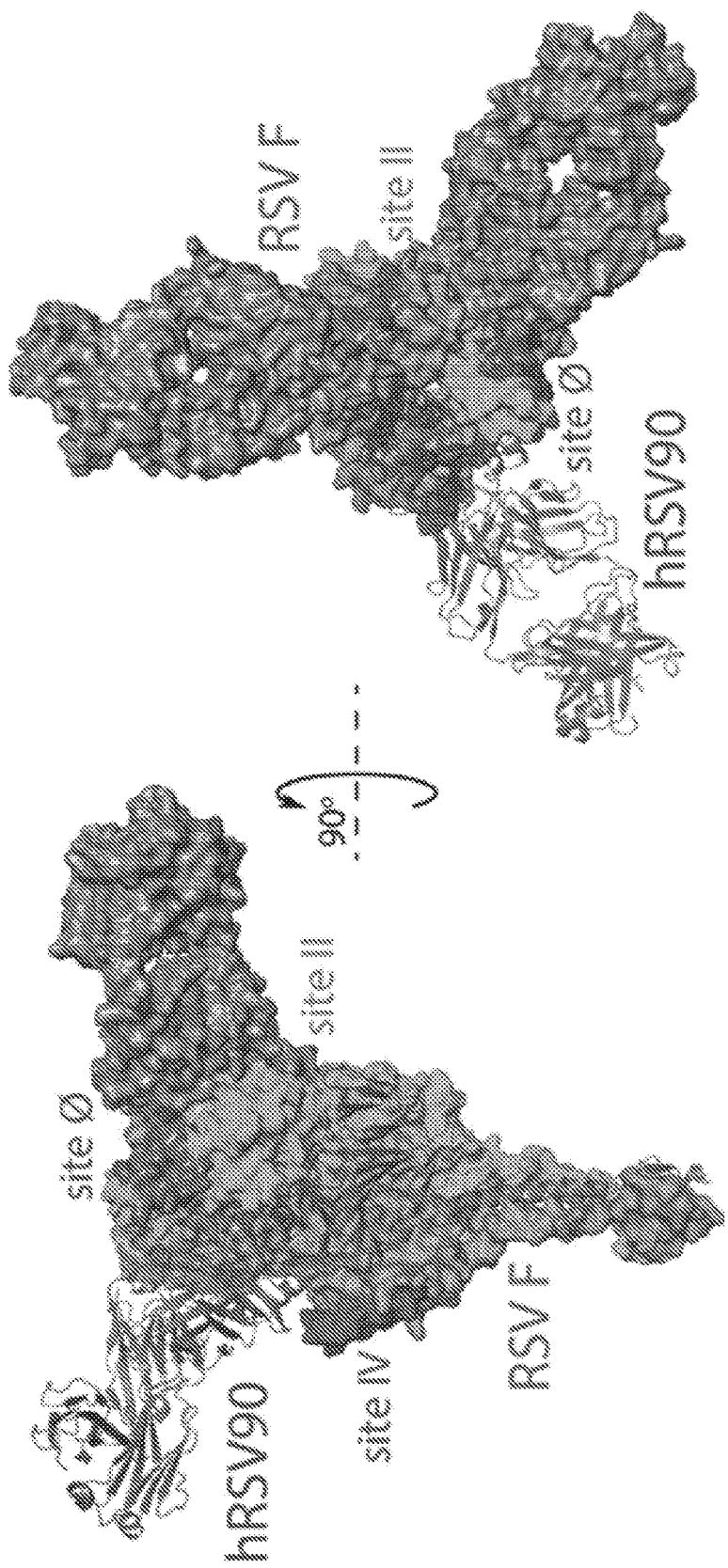

Respiratory syncytial virus (RSV) remains a major human pathogen, infecting the majority of infants before age two and causing reinfection throughout life. Despite decades of RSV research, there is no licensed RSV vaccine. Most candidate vaccines studied to date have incorporated the RSV fusion (F) surface glycoprotein, since the sequence of F is highly conserved among strains of RSV. In order to better define the human B cell response to RSV F, the inventors isolated from a single donor thirteen new neutralizing human monoclonal antibodies (mAbs) that recognized the RSV F protein in the pre-fusion conformation. Epitope binning studies showed that the majority of neutralizing mAbs targeted a new antigenic site on the globular head domain of F, designated here antigenic site VIII, which occupies an intermediate position between the previously defined major antigenic sites II and site Ø. Antibodies to site VIII competed for binding with antibodies to both of those adjacent neutralizing sites. The new mAbs exhibited unusual breadth for pre-fusion F-specific antibodies, cross-reacting with F proteins from both RSV subgroups A and B viruses. The inventors solved the X-ray crystal structure of one site VIII mAb, hRSV90, in complex with pre-fusion RSV F protein. The structure revealed a large footprint of interaction for hRSV90 on RSV F, in which the heavy chain and light chain both have specific interactions mediating binding to site VIII, the heavy chain overlaps with site Ø, and the light chain interacts partially with site II. These and other aspects of the disclosure are set forth in detail below. These and other aspects of the disclosure are described in detail below.

I. RESPIRATORY SYNCYTIAL VIRUS

Human respiratory syncytial virus (RSV) is a syncytial virus that causes respiratory tract infections. It is a major cause of lower respiratory tract infections and hospital visits during infancy and childhood. A prophylactic medication, palivizumab, can be employed to prevent human RSV in preterm (under 35 weeks gestation) infants, infants with certain congenital heart defects (CHD) or bronchopulmonary dysplasia (BPD), and infants with congenital malformations of the airway. Treatment is limited to supportive care (e.g., C-PAP), including oxygen therapy.

Human RSV is a negative-sense, single-stranded RNA virus of the family Pneumoviridae. Its name comes from the fact that F proteins on the surface of the virus cause the cell membranes on nearby cells to merge, forming syncytia. It was first isolated in 1956 from a chimpanzee, and called Chimpanzee Coryza Agent (CCA). Also in 1956, a new type of cytopathogenic myxovirus was isolated from a group of human infants with infantile croup.

In temperate climates there is an annual epidemic during the winter months. In tropical climates, infection is most common during the rainy season. In the United States, 60% of infants are infected during their first RSV season, and nearly all children will have been infected with the virus by 2-3 years of age. Of those infected with RSV, 2-3% will develop bronchiolitis, necessitating hospitalization. Natural infection with HRSV induces protective immunity which wanes over time—possibly more so than other respiratory viral infections— and thus people can be infected multiple times. Sometimes an infant can become symptomatically infected more than once, even within a single HRSV season. Severe HRSV infections have increasingly been found among elderly patients. Young adults can be re-infected every five to seven years, with symptoms looking like a sinus infection or a cold (infections can also be asymptomatic).

The incubation time (from infection until symptoms arrive) is 4-5 days. For adults, HRSV produces mainly mild symptoms, often indistinguishable from common colds and minor illnesses. The Centers for Disease Control consider HRSV to be the "most common cause of bronchiolitis (inflammation of the small airways in the lung) and pneumonia in children under 1 year of age in the United States." For some children, RSV can cause bronchiolitis, leading to severe respiratory illness requiring hospitalization and, rarely, causing death. This is more likely to occur in patients that are immunocompromised or infants born prematurely. Other HRSV symptoms common among infants include listlessness, poor or diminished appetite, and a possible fever.

Recurrent wheezing and asthma are more common among individuals who suffered severe HRSV infection during the first few months of life than among controls; whether HRSV infection sets up a process that leads to recurrent wheezing or whether those already predisposed to asthma are more likely to become severely ill with HRSV has yet to be determined.

Symptoms of pneumonia in immuno-compromised patients such as in transplant patients and especially bone marrow transplant patients should be evaluated to rule out HRSV infection. This can be done by means of polymerase chain reaction (PCR) testing for HRSV nucleic acids in peripheral blood samples if all other infectious processes have been ruled out or if it is highly suspicious for RSV such as a recent exposure to a known source of HRSV infection.

Complications include bronchiolitis or pneumonia, asthma, recurring infections, and acute otitis media.

Transmission. The incubation period is 2-8 days, but is usually 4-6 days. RSV spreads easily by direct contact, and can remain viable for a half an hour or more on hands or for up to 5 hours on countertops. Childcare facilities allow for rapid child-to-child transmission in a short period of time. RSV can last 2-8 days, but symptoms may persist for up to three weeks.

The human RSV is virtually the same as chimpanzee coryza virus and can be transmitted from apes to humans, although transmission from humans to apes is more common. The virus has also been recovered from cattle, goats and sheep, but these are not regarded as major vectors of transmission and there is no animal reservoir of the virus.

Virology. Human RSV is a medium-sized (120-200 nm) enveloped virus that contains a lipoprotein coat and a linear negative-sense RNA genome (must be converted to an anti-sense genome prior to translation). The former contains virally encoded F, G, and SH lipoproteins. The F and G lipoproteins are the only two that target the cell membrane, and are highly conserved among RSV isolates. HRSV is divided into two antigenic subgroups, A and B, on the basis of the reactivity of the virus with monoclonal antibodies against the attachment (G) and fusion (F) glycoproteins. Subtype B is characterized as the asymptomatic strains of the virus that the majority of the population experiences. The more severe clinical illnesses involve subtype A strains, which tend to predominate in most outbreaks.

The genome is ~15,000 nucleotides in length and is composed of a single strand of RNA with negative polarity. It has 10 genes encoding 11 proteins. To date, 10 HRSV-A genotypes have been designated, GA1 to GA7, SAA1, NA1, and NA2. The HRSV-B genotypes include GB1 to GB4, SAB1 to SAB3, and BA1 to BA6. The genome of HRSV was completely sequenced in 1997.

Diagnosis. Human respiratory syncytial virus may be suspected based on the time of year of the infection; prevalence usually coincides with the winter flu season. Tests include (a) chest X-rays to check for typical bilateral perihilar fullness of bronchiolitis induced by the virus, (b) skin monitoring to check for hypoxemia, a lower than usual level of oxygen in the bloodstream, (c) blood tests to check white cell counts or to look for the presence of viruses, bacteria or other organisms, and (d) lab testing of respiratory secretions.

Several different types of laboratory tests are commercially available for diagnosis of RSV infection. Rapid diagnostic assays performed on respiratory specimens are available commercially. Most clinical laboratories currently utilize antigen detection tests. Compared with culture, the sensitivity of antigen detection tests generally ranges from 80% to 90%. Antigen detection tests and culture are generally reliable in young children but less useful in older children and adults.

Sensitivity of virus isolation from respiratory secretions in cell culture varies among laboratories. RT-PCR assays are now commercially available. The sensitivity of these assays is equal to or exceeds the sensitivity of virus isolation and antigen detections methods. Highly sensitive RT-PCR assays should be considered when testing adults, because they may have low viral loads in their respiratory specimens.

Serologic tests are less frequently used for diagnosis. Although useful for research, a diagnosis using a collection of paired acute and convalescent sera to demonstrate a significant rise in antibody titer to HRSV cannot be made in time to guide care of the patient. On top of that, the antibody level does not always correlate with the acuteness or activity level of the infection.

RSV infection can be confirmed using tests for antigens or antibodies, or viral RNA by reverse transcription PCR. Quantification of viral load can be determined by various assay tests.

Prevention. As the virus is ubiquitous in all parts of the world, avoidance of infection is not possible. However, palivizumab (brand name Synagis manufactured by MedImmune), a moderately effective prophylactic drug, is available for infants at high risk. Palivizumab is a monoclonal antibody directed against RSV surface fusion protein. It is given by monthly injections, which are begun just prior to the RSV season and are usually continued for five months. HRSV prophylaxis is indicated for infants that are premature or have either cardiac or lung disease, but the cost of prevention limits use in many parts of the world.

Vaccine Research. A vaccine trial in 1960s using a formalin-inactivated vaccine (FI-RSV) increased disease severity in children who had been vaccinated. There is much active investigation into the development of a new vaccine, but at present no vaccine exists. Some of the most promising candidates are based on temperature sensitive mutants which have targeted genetic mutations to reduce virulence.

Scientists are attempting to develop a recombinant human respiratory syncytial virus vaccine that is suitable for intranasal instillation. Tests for determining the safety and level of resistance that can be achieved by the vaccine are being conducted in the chimpanzee, which is the only known animal that develops a respiratory illness similar to humans.

The development of a commercial human RSV vaccine has remained elusive. Recent breakthroughs have sparked continued interest in this highly sought after vaccine as the annual medical burden relating to human RSV has remained high, equal to Influenza and Pneumococcus.

Treatment. To date, treatment has been limited to supportive measures. Adrenaline, bronchodilators, steroids, antibiotics, and ribavirin confer "no real benefit." Studies of nebulized hypertonic saline have shown that the use of nebulized 3% HS is a safe, inexpensive, and effective treatment for infants hospitalized with moderately severe viral bronchiolitis where respiratory syncytial virus (RSV) accounts for the majority of viral bronchiolitis cases. One study noted a 26% reduction in length of stay: 2.6±1.9 days, compared with 3.5±2.9 days in the normal-saline treated group (p=0.05). Supportive care includes fluids and oxygen until the illness runs its course. Salbutamol may be used in an attempt to relieve any bronchospasm if present. Increased airflow, humidified and delivered via nasal cannula, may be supplied in order to reduce the effort required for respiration.

II. MONOCLONAL ANTIBODIES AND PRODUCTION THEREOF

A. General Methods

It will be understood that monoclonal antibodies binding to Human respiratory syncytial virus will have several applications. These include the production of diagnostic kits for use in detecting and diagnosing Human respiratory syncytial virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^6$ to $1 \times 10^8$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microliter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In particular, the antibodies of the present disclosure, in one aspect, relate to the identification, through their binding specificity, of a previously unrecognized epitope that lies within what the inventors now term "antigenic site VIII." This epitope is located between sites II and Ø, while also being close to the trimer-dependent mAb AM14 site and distant from antigenic site IV. Residues 16, 173, 174, 194, and 201 of RSV F all appear to have some involvement.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (–0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (–0.4), sulfur containing amino acids: cysteine (–1.0) and methionine (–1.3); hydrophobic, nonaromatic amino acids: valine (–1.5), leucine (–1.8), isoleucine (–1.8), proline (–0.5±1), alanine (–0.5), and glycine (0); hydrophobic, aromatic amino acids: tryptophan (–3.4), phenylalanine (–2.5), and tyrosine (–2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fe region to have a different isotype, different functionalities can be achieved. For example, changing to $IgG_1$ can increase antibody dependent cell cytotoxicity, switching to class A can improve tissue distribution, and switching to class M can improve valency. Modifications in the Fc region can be introduced to extend the in vivo half-life of the antibody, or to alter Fc mediated functions such as complement activation, antibody dependent cellular cytotoxicity (ADCC), and FcR mediated phagocytosis.

Other types of modifications include residue modification designed to reduce oxidation, aggregation, deamidation, and immunogenicity in humans. Other changes can lead to an increase in manufacturability or yield, or reduced tissue cross-reactivity in humans.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido)

ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF HUMAN RESPIRATORY SYNCYTIAL VIRUS INFECTION

A. Formulation and Administration

The present disclosure provides pharmaceutical compositions comprising anti-human respiratory syncytial virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of Human respiratory syncytial virus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to from an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/ or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting Human respiratory syncytial virus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of human respiratory syncytial virus antibodies directed to specific viral epitopes in samples also is provided. The steps of various useful immunodetection methods have been described in the scientific literature, such as, e.g., Doolittle and Ben-Zeev (1999), Gulbis and Galand 11993), De Jager et al. (1993), and Nakamura et al. (1987). In general, the immunobinding methods include obtaining a sample suspected of containing Human respiratory syncytial virus, and contacting the sample with a first antibody in accordance with the present disclosure, as the case may be, under conditions effective to allow the formation of immunocomplexes.

These methods include methods for purifying human respiratory syncytial virus or related antigens from a sample. The antibody will preferably be linked to a solid support, such as in the form of a column matrix, and the sample suspected of containing the Human respiratory syncytial virus or antigenic component will be applied to the immobilized antibody. The unwanted components will be washed from the column, leaving the human respiratory syncytial virus antigen immunocomplexed to the immobilized antibody, which is then collected by removing the organism or antigen from the column.

The immunobinding methods also include methods for detecting and quantifying the amount of human respiratory syncytial virus or related components in a sample and the detection and quantification of any immune complexes formed during the binding process. Here, one would obtain a sample suspected of containing human respiratory syncytial virus or its antigens, and contact the sample with an antibody that binds Human respiratory syncytial virus or components thereof, followed by detecting and quantifying the amount of immune complexes formed under the specific conditions. In terms of antigen detection, the biological sample analyzed may be any sample that is suspected of containing human respiratory syncytial virus or Human respiratory syncytial virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Human respiratory syncytial virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Human respiratory syncytial virus or Human respiratory syncytial virus antigen is added to the wells. After binding and washing to remove non-specifically bound immune complexes, the bound antigen may be detected. Detection may be achieved by the addition of another anti-Human respiratory syncytial virus antibody that is linked to a detectable label. This type of ELISA is a simple "sandwich ELISA." Detection may also be achieved by the addition of a second anti-Human respiratory syncytial virus antibody, followed by the addition of a third antibody that has binding affinity for the second antibody, with the third antibody being linked to a detectable label.

In another exemplary ELISA, the samples suspected of containing the Human respiratory syncytial virus or Human respiratory syncytial virus antigen are immobilized onto the well surface and then contacted with the anti-Human respiratory syncytial virus antibodies of the disclosure. After binding and washing to remove non-specifically bound immune complexes, the bound anti-Human respiratory syncytial virus antibodies are detected. Where the initial anti-Human respiratory syncytial virus antibodies are linked to a detectable label, the immune complexes may be detected directly. Again, the immune complexes may be detected using a second antibody that has binding affinity for the first anti-Human respiratory syncytial virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Human respiratory syncytial virus antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled Human respiratory syncytial virus monoclonal antibodies to determine the amount of Human respiratory syncytial virus antibodies in a sample. The basic format would include contacting a known amount of Human respiratory syncytial virus monoclonal antibody (linked to a delectable label) with Human respiratory syncytial virus antigen or particle. The Human respiratory syncytial virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Human respiratory syncytial virus or Human respiratory syncytial virus antigens, the antibodies may be included in the kit. The immunodetection kits will thus comprise, in suitable container means, a first antibody that binds to Human respiratory syncytial virus or Human respiratory syncytial virus antigen, and optionally an immunodetection reagent.

In certain embodiments, the Human respiratory syncytial virus antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Human respiratory syncytial virus or Human respiratory syncytial virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VI. QUALITY CONTROL AND VACCINE TESTING

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity, and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns, but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against our oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

VII. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Enzyme linked immunosorbent assay (ELISA). For recombinant protein capture ELISA, 384-well plates were treated with 2 µg/mL of antigen overnight at 4° C. The plates were blocked for one hour with 2% milk supplemented with 2% goat serum. Plates were washed three times with PBS-T, and primary mAbs or hybridoma cell culture supernatants were applied to wells for one hour. Plates were washed with PBS-T four times before applying 25 µL secondary antibody (goat anti-human IgG Fc, Meridian Life Science) at a dilution of 1:4,000 in blocking solution. After a one-hour incubation, the plates were washed five times with PBS-T, and 25 µL of phosphatase substrate solution (1 mg/mL phosphatase substrate in 1 M Tris aminomethane, Sigma) was added to each well. The plates were incubated at room temperature for approximately 30 min before reading the optical density at 405 nm on a Biotek plate reader. Experiments with the RSV F mutants were conducted similarly.

Human hybridoma generation. The generation of human hybridomas has been described previously (McLellan, J. S., 2015). Briefly, PBMCs were isolated from a single human donor and were transformed with Epstein-Barr virus (EBV). After seven to ten days, culture supernatants were screened for binding to recombinant RSV A2 F SC-TM. Cells from positive wells were fused with HMMA2.5 myeloma cells by electrofusion to generate hybridomas (Yu et al., 2008). Hybridomas were placed in HAT and ouabain selection media and screened after two weeks for mAb production by ELISA. Cells from wells with reactive supernatants were expanded to 48-well plates for one week before being screened again by ELISA, and then subjected to single-cell flow cytometric cell sorting. After cell sorting into 384-well plates containing Medium E (StemCell Technologies), hybridomas were screened by ELISA before expansion into both 48-well and 12-well plates. Hybridoma cells lines were expanded in Medium E until 80% confluent in 75-cm² flasks. For antibody production, cells from one 75-cm² cell culture flask were collected with a cell scraper and expanded to four 225-cm² cell culture flasks in serum-free medium (Hybridoma-SFM, GIBCO). After 21 days, supernatants were sterile filtered using 0.45 μm pore size filter devices.

RSV plaque neutralization experiments. MAbs isolated from hybridoma supernatants were incubated 1:1 with a suspension of infectious RSV strain A2, 18537 B, or Long for 1 hr. Following this, confluent HEp-2 cell culture monolayers, maintained in Opti-MEM I+GlutaMAX (Fisher) supplemented with 2% fetal bovine serum at 37° C. in a $CO_2$ incubator, in 24-well plates were inoculated with 50 μL of the antibody:virus mixture for 1 hr. After the hour, cells were overlaid with 1 mL of 0.75% methylcellulose dissolved in Opti-MEM I+GlutaMAX. Cells were incubated for four days, after which the plaques were visualized by fixing cells with 10% neutral-buffered formalin and staining with crystal violet. Plaques were counted and compared to a virus control. Data were analyzed with Prism software (Graph-Pad) to obtain $IC_{50}$ values.

Human mAb and Fab production and purification. For antibody purification from hybridoma supernates, HiTrap MabSelectSure columns (GE Healthcare Life Sciences) were used to purify antibodies using the manufacturer's protocol. To obtain Fab fragments, papain digestion was used (Pierce Fab Preparation Kit, Thermo Scientific). Fab fragments were purified by removing IgG and Fc contaminants using a HiTrap MabSelectSure column followed by purification with an anti-CH1 column (GE Healthcare Life Sciences).

Assessing self-reactivity of mAbs by flow cytometry. Cultures of Jurkat E6-1 (ATCC) and lentivirus transducted Jurkat E6-1 cells that express Zaire Ebolavirus glycoprotein on the surface (kind gift by Carl Davis and Rafi Ahmed, Emory University School of Medicine) were grown in RPMI-1640 medium supplemented with 10% fetal bovine serum (FBS; HyClone) according to the ATCC recommendations. Cells were washed with ice-cold FACS buffer (Dulbecco's PBS containing 2% FBS and 50 nM Dasatinib), counted, seeded at approx. 50,000 viable cells per well in V-bottom 96-well plate for each mAb to be tested, and incubated 60 min at 4° C. with serial 10-fold dilutions of mAb in total volume 100 μL per staining. Cells were washed with FACS buffer by centrifugation 2 min at 800×g followed by incubation with 1:500 dilution of secondary goat anti-human IgG PE Ab (SouthernBiotech) in FACS buffer. After washing, 5,000-10,000 live cell events were acquired using a 3-laser LSR-II flow cytometer (BD Biosciences) and analyzed with FlowJo software (Tree Star). Dead cell population was excluded using propidium iodide staining.

Production and purification of recombinant RSV F protein RSV mAbs, and epitope immunogens. Plasmids encoding cDNAs for RSV subgroup A strain A2 F protein (wild-type post-fusion lacking the signal peptide and transmembrane domain), the SC-TM construct, and the subgroup B strain 18537 protein construct (wild-type post-fusion F protein lacking the signal peptide and transmembrane domain) were synthesized (Genscript). The RSV B 18537 Ds-Cav1 (pre-fusion) construct was a gift from Barney Graham (NIH). Plasmids were expanded in *E. coli* DH5α cells, and DNA was purified using Qiagen Plasmid Maxiprep kits (Qiagen). For each liter of protein expression, 1.3 mg of plasmid DNA was mixed with 2 mg of polyethylenimine in Opti-MEM I+GlutaMAX cell culture medium (Fisher). After 10 min, the DNA mixture was added to HEK293 cells at $1 \times 10^6$ cells/mL. The culture supernatant was harvested after 6 days, and the protein was purified by HiTrap Talon crude (GE Healthcare Life Sciences) column for RSV F protein variants and mutants. Expression and purification of mAbs 101F, motavizumab, and D25 was previously described (Mousa et al., 2016. Commercial preparations of palivizumab (Synagis; Medimmune) were obtained from the pharmacy at Vanderbilt University Medical Center.

Crystallization and structure determination of 14N4-Fab and 14N4-Fab-RSV F. To crystallize hRSV90 Fab in complex with RSV A2 F SC-TM, both Fab cleaved from hybridoma-derived IgG of hRSV90 and RSV A2 F were buffer-exchanged in excess into 50 mM Tris pH 7.5, 50 mM NaCl. hRSV90-Fab was mixed in excess with RSV A2 F SC-TM protein and incubated at 37° C. for two hours. Following this, the sample was subjected to size exclusion chromatography (S200, 16/300, GE Healthcare Life Sciences) in 50 mM Tris pH 7.5, 50 mM NaCl. The complex was concentrated to 10 mg/mL and crystals were obtained in Hampton Crystal Screen HT in various conditions. The best diffracting crystals were obtained in 30% PEG 400, 200 mM $MgCl_2.6H_2O$, and 100 mM HEPES pH 7.5. X-ray diffraction data were collected at the Advanced Photon Source LS-CAT beamline 21-ID-G. Data were indexed and scaled using XDS (Kabsch, 2010) and were significantly anisotropic. The data was submitted to the diffraction anisotropy server and the data were truncated to 3.1 Å along the c* axis, and to 3.6 Å along the a*/b* axes. A molecular replacement solution was obtained in Phaser (Emsley & Cowtan, 2004) using the RSV A2 F SC-TM structure (PDB 5C6B), and by separately searching the variable and constant regions of a poly-alanine truncated Fab structure (PDB: 4Q9Q). The structure of the complex was completed by manually building in COOT (Emsley & Cowtan, 2004) followed by subsequent rounds of manual rebuilding and refinement in Phenix (Adams et al., 2010). The data collection and refinement statistics are shown in Table S1.

RSV F mutant western blot. An SDS-PAGE gel (4-12% Bis-Tris) was run for the RSV F SC-TM protein mutants. The proteins were transferred to a PVDF membrane using the iBlot system (Thermo Fisher Scientific). The membrane was blocked in 5% non-fat milk for one hour, and then washed 3× with PBS-T. Following this, the membrane was incubated with a 1:1,000 dilution of monoclonal anti-polyhistidine-alkaline phosphatase antibody (Sigma, #A5588) in 5% nonfat milk for one hour. The membrane was washed 3× with PBS-T and incubated with BM purple chromogenic substrate.

Example 2—Results

In order to further characterize the human immune response to the RSV F protein, and in particular the pre-fusion form of RSV F, the inventors used hybridoma technology (Smith & Crowe, 2015) to isolate new mAbs to RSV and identified thirteen new neutralizing human mAbs that recognized the pre-fusion conformation of RSV F protein. Peripheral blood mononuclear cells were isolated from a single 8-year-old human donor by Ficoll-gradient centrifugation, and the cells were frozen for later use. For B cell screening, thawed cells were transformed with Epstein-Barr virus and plated in 384-well plates to generate immortalized B cell clusters. Supernatants from the transformed cells were screened for antibodies binding to a highly-stable pre-fusion conformation of RSV A2 F, using single-chain triple mutant (SC-TM) construct (Krarup et al., 2015). B cells from cultures producing antibodies reactive with the pre-fusion F protein were electrofused with the HMMA2.5 myeloma cell line to generate stable hybridoma cell lines. To obtain homogeneous antibody secretions, hybridoma cells were cloned biologically by single-cell flow cytometric sorting. Hybridomas were expanded step-wise to 1 L cultures, and mAbs were purified from filtered culture supernatants. Purified mAb yields from the cultures ranged widely depending on the hybridoma clone, with the lowest being 1.5 mg/L, and the highest nearing 30 mg/L (Table 5). RSV-specific mAbs were characterized by antibody isotyping analysis. All mAbs except hRSV130 were of the IgG1 subclass, and the majority of light chains were of the kappa subtype (Table 5).

Figure 4:
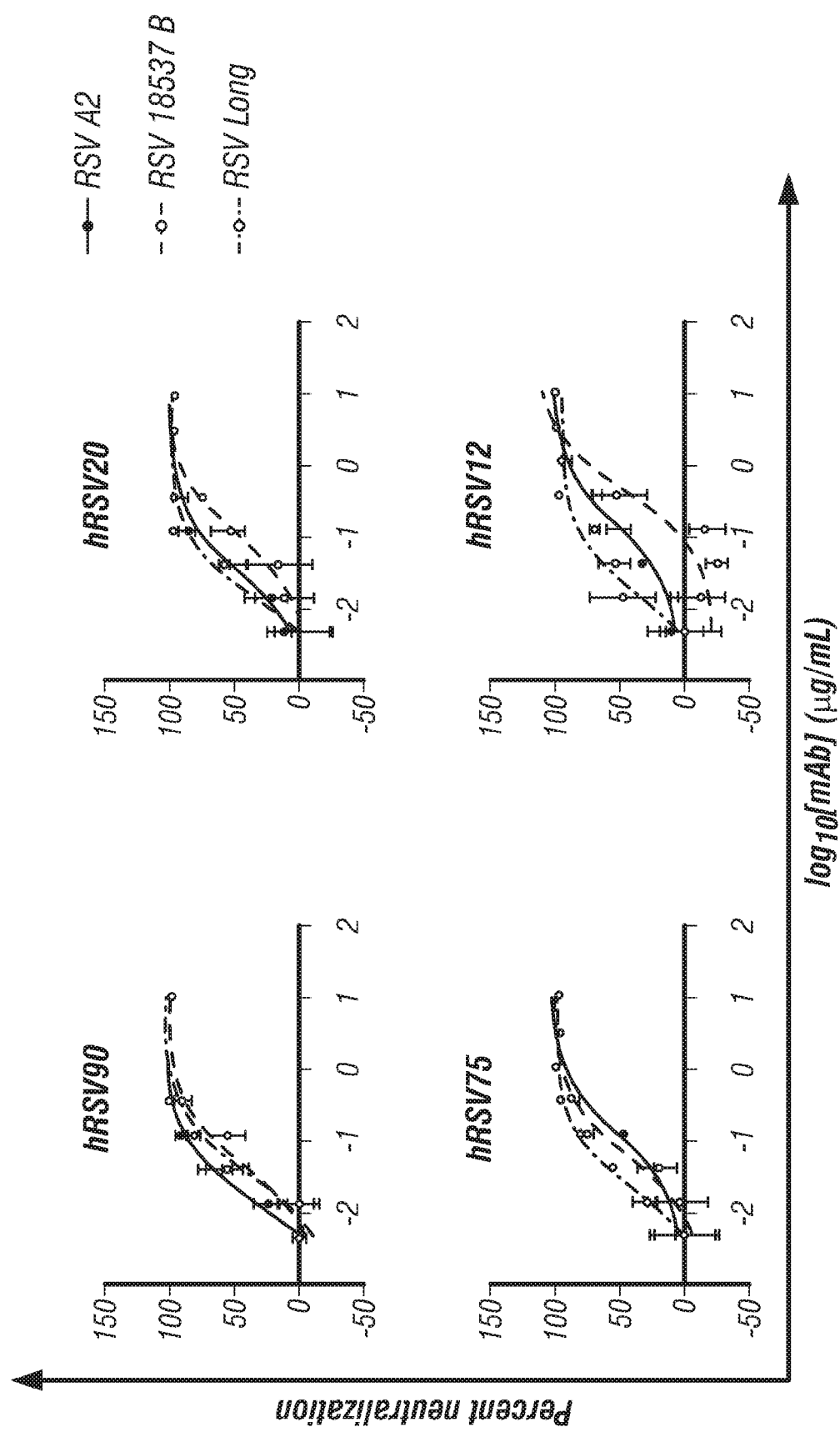
FIG. 4. Neutralization curves for the newly isolated RSV F-specific mAbs. $IC_{50}$ values are displayed in Table 1. Error bars represent the standard deviation, n=3. A non-neutralizing RSV F specific mAb, hRSV5, was used as a negative control. MAb D25 was used as a positive control.
Figure 4:
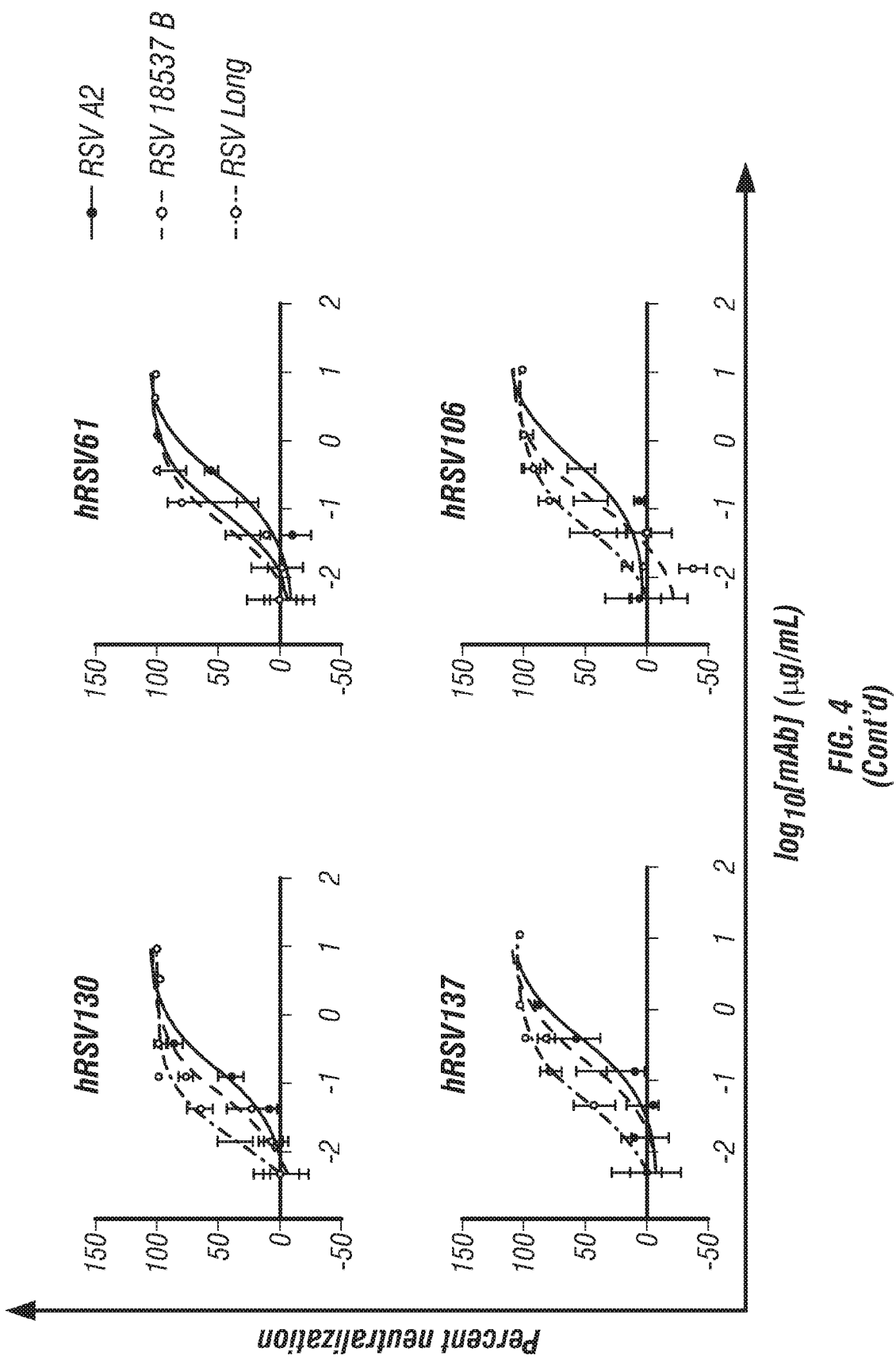
Figure 4:
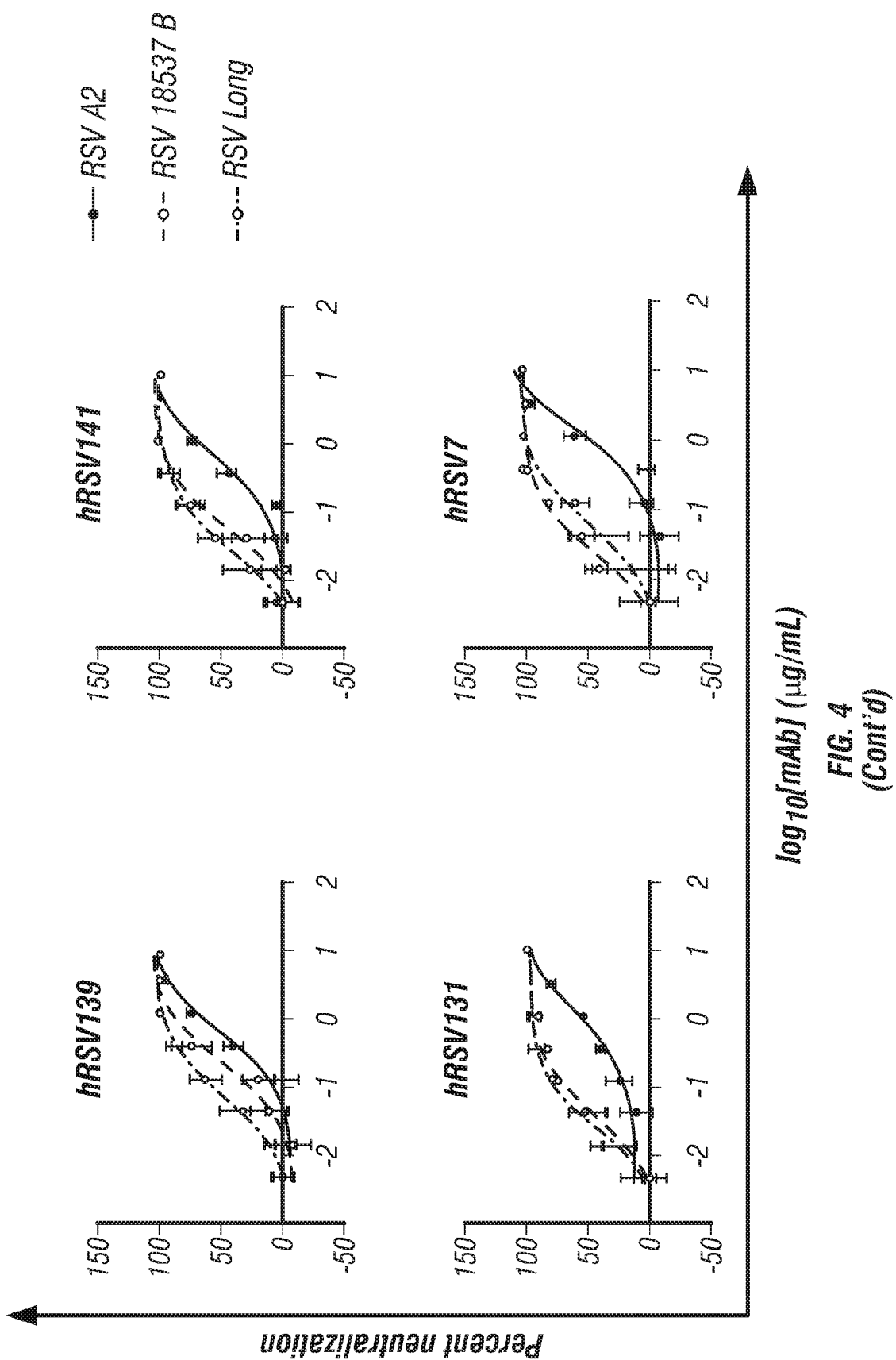
Figure 4:
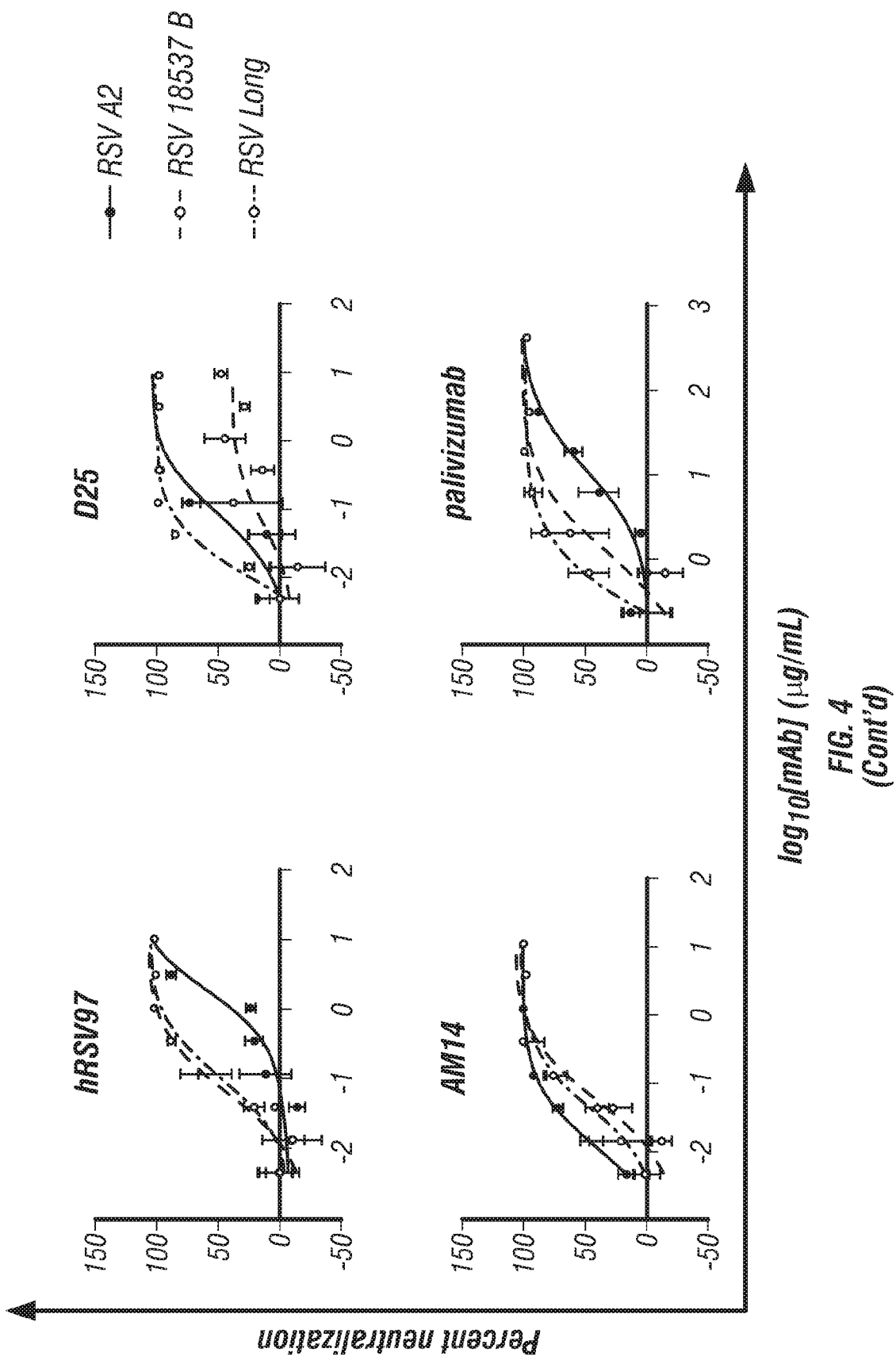
Figure 4:
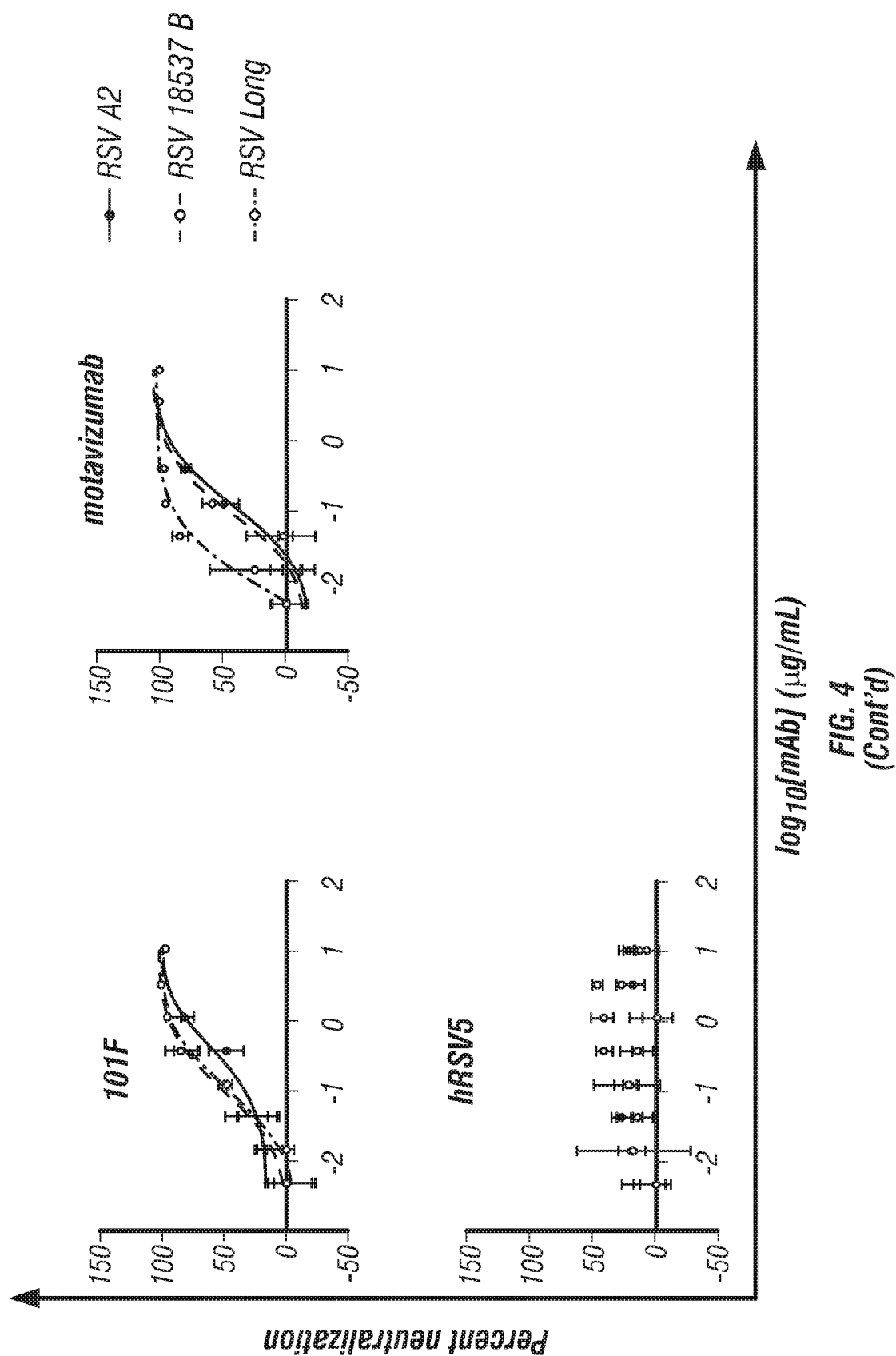
Figure 5:
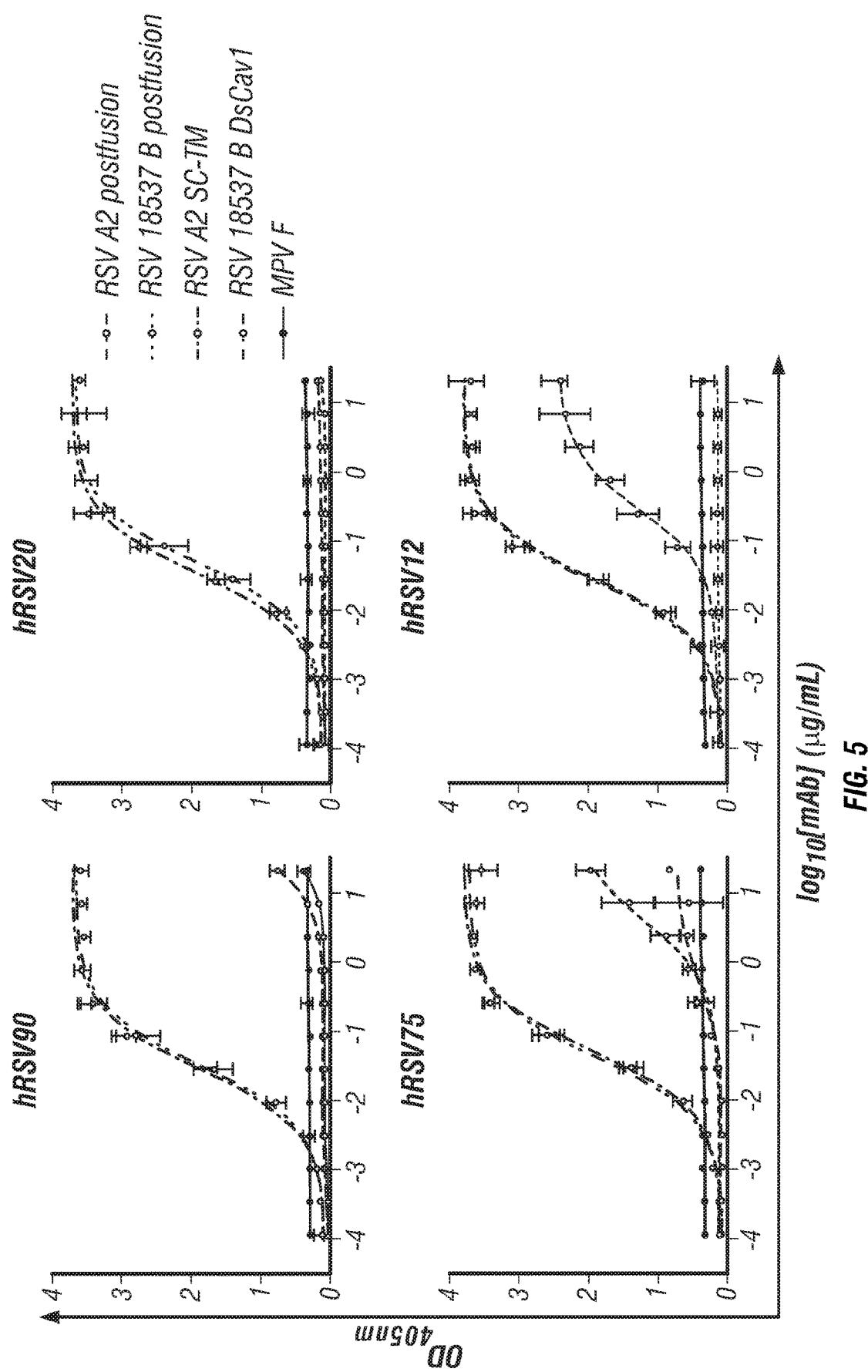
FIG. 5. ELISA binding curves for the newly isolated mAbs and positive controls to RSV F protein strain and construct variants. The metapneumovirus F protein was used as a negative binding control. An Ebola-virus specific mAb EBOV284 was used as a negative mAb control. Error bars indicate 95% confidence intervals, n=4. $EC_{50}$ values for these curves are displayed in Table 1.
Figure 5:
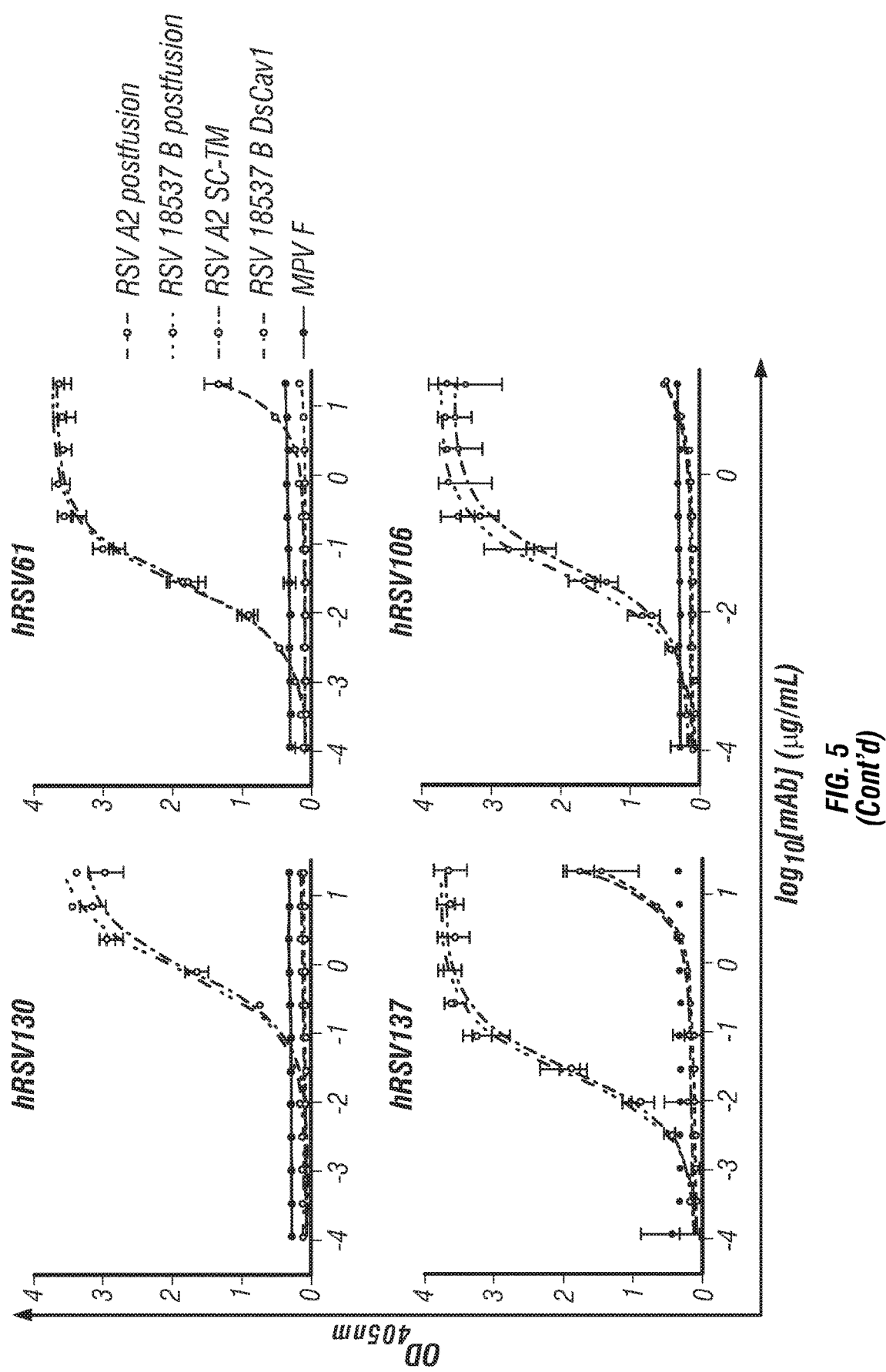
Figure 5:
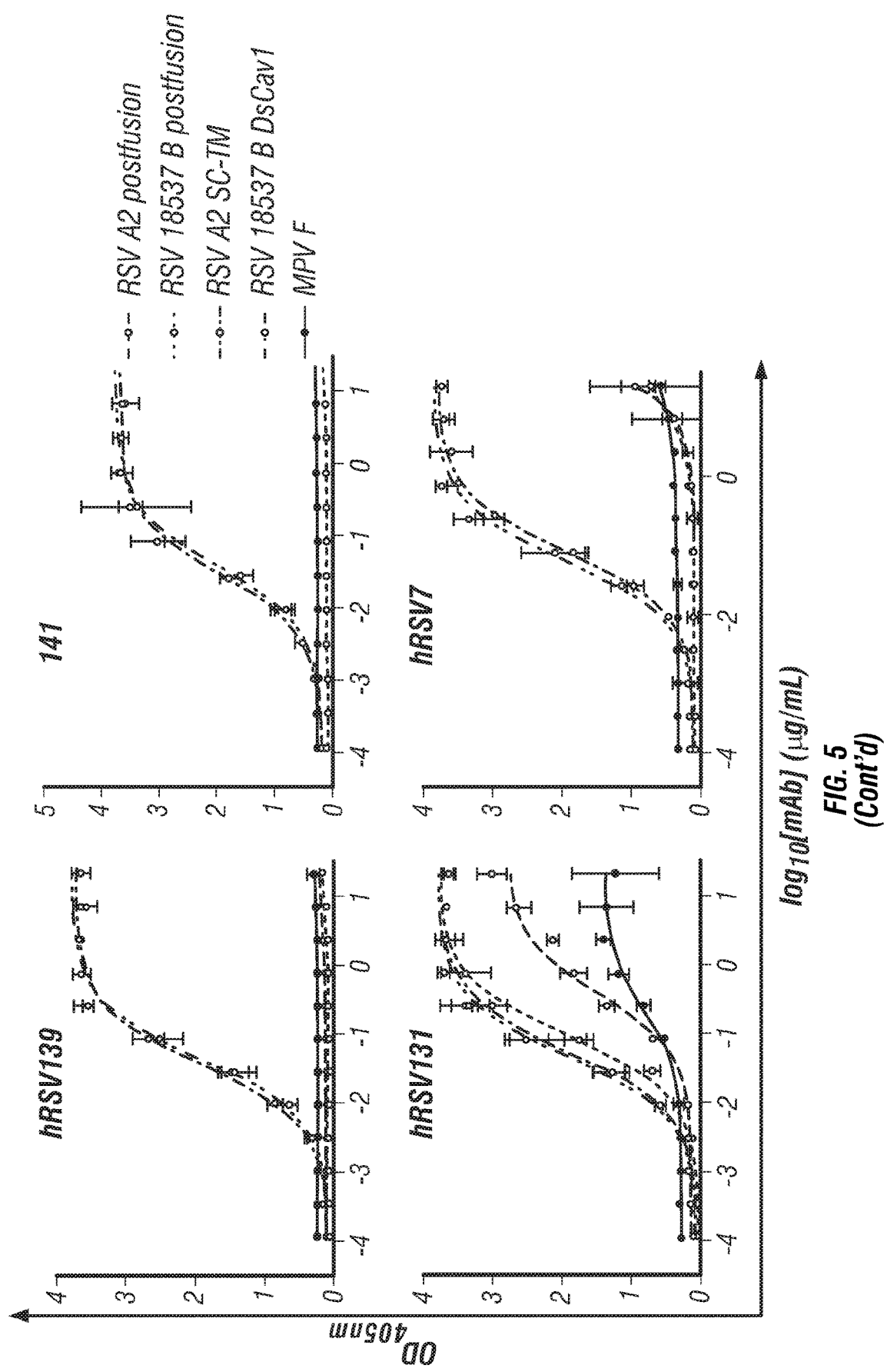
Figure 5:
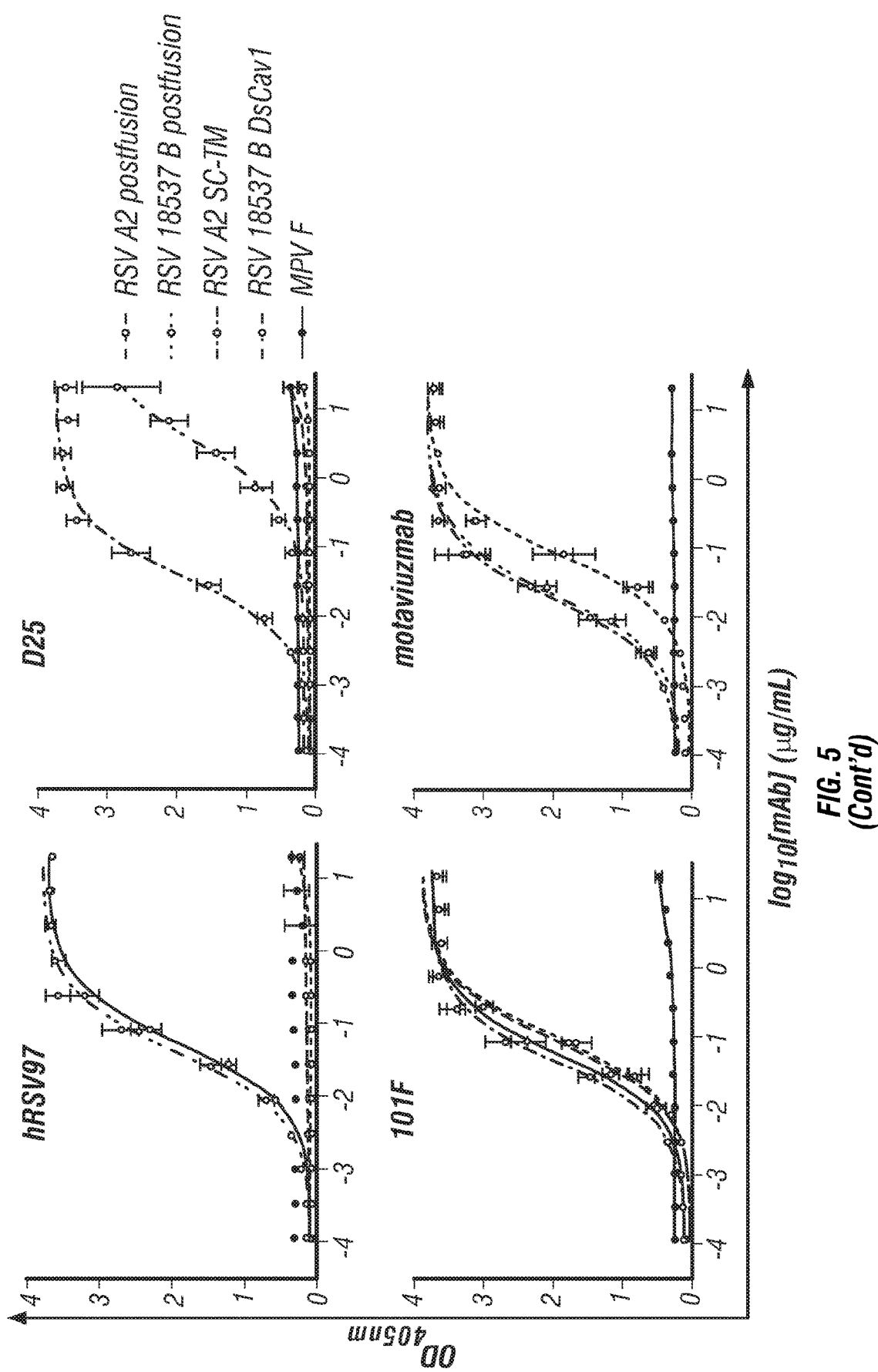
Figure 5:
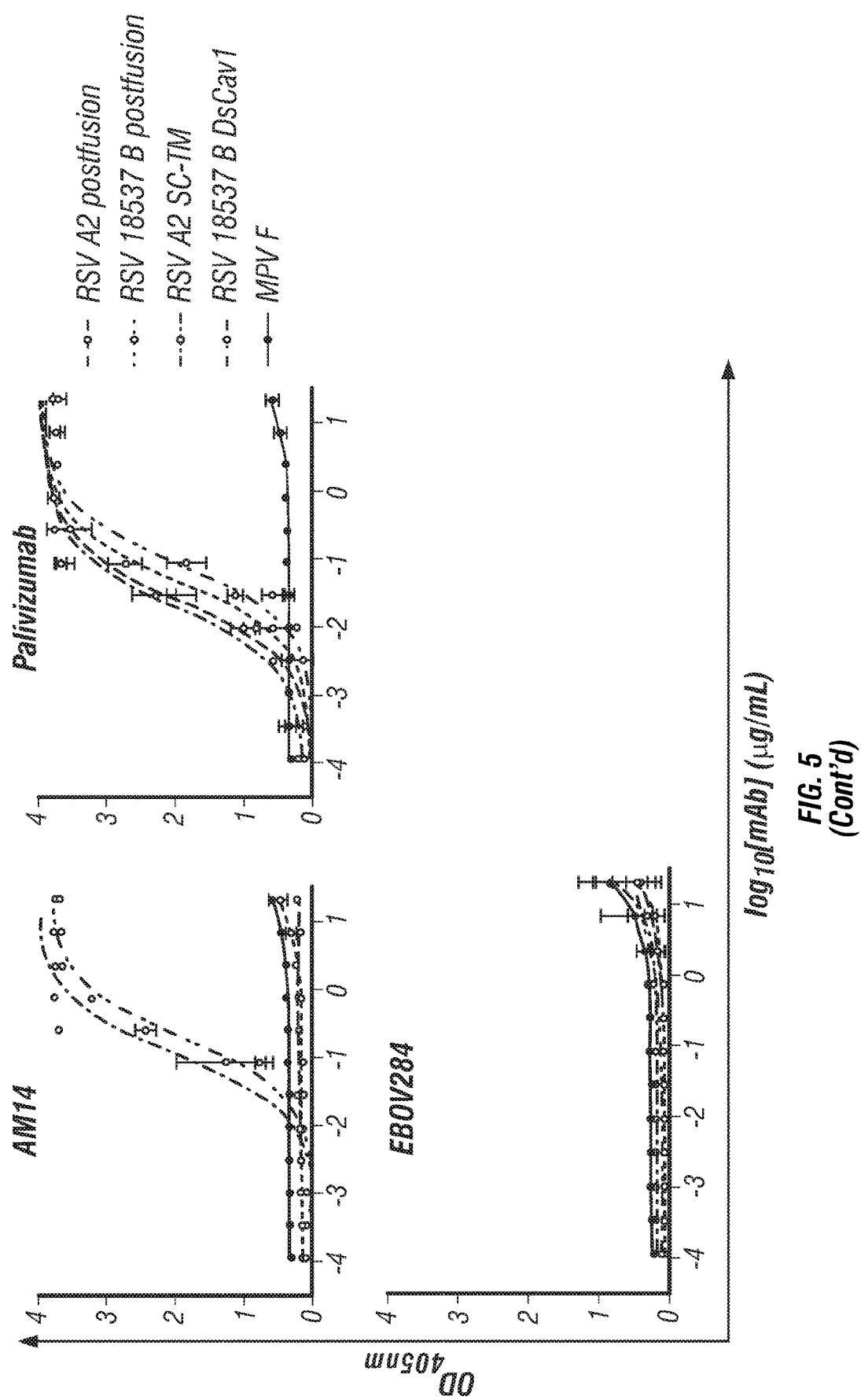
Figure 6A:
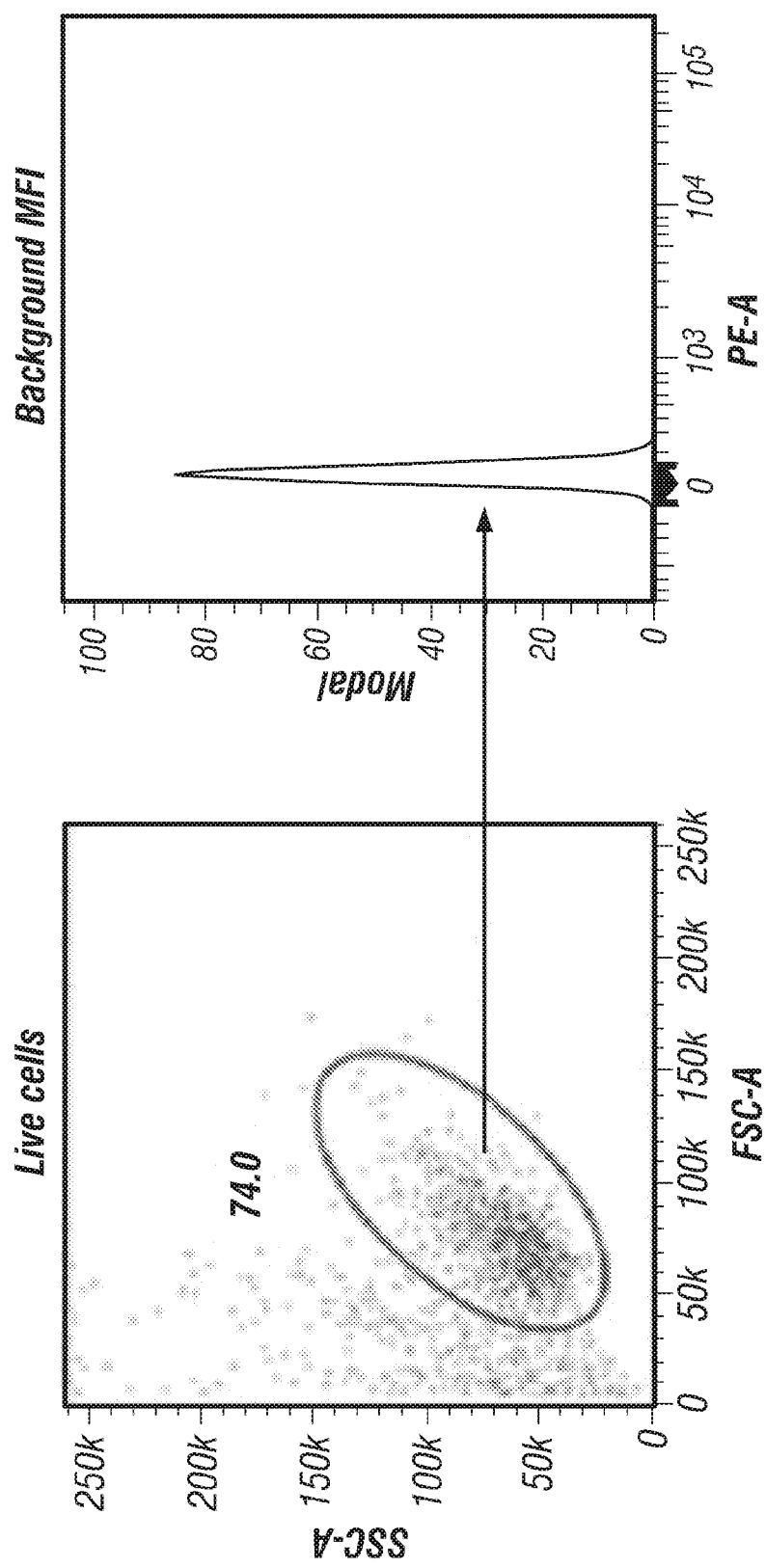
FIGS. 6A-C. Assessing self-reactivity of hRSV mAbs by flow cytometry. Jurkat cell line was stained with individual mAbs followed by incubation with secondary phycoerythrin (PE)-conjugated Ab and flow cytometric analysis.
Figure 6B:
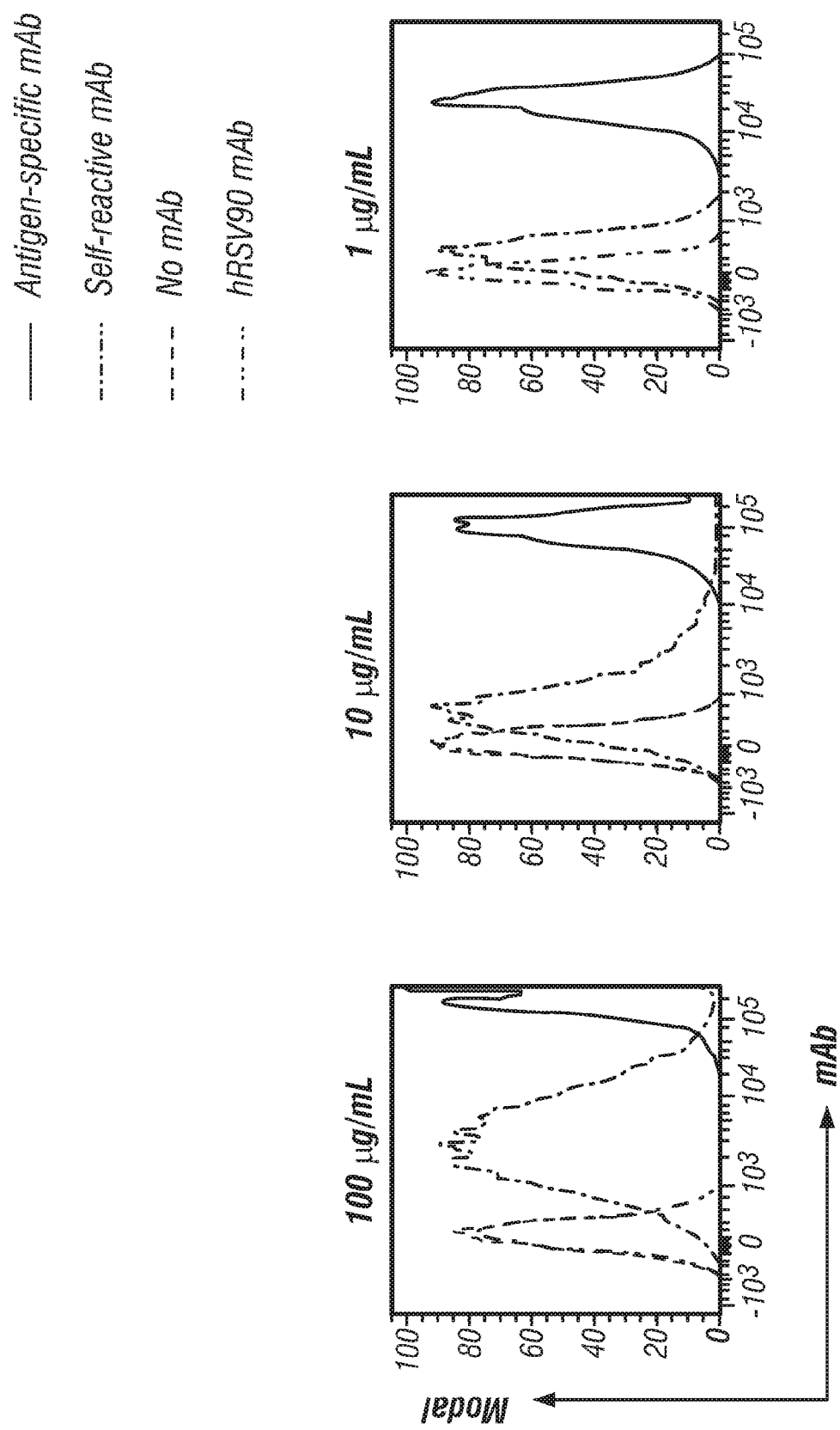
Figure 6C:
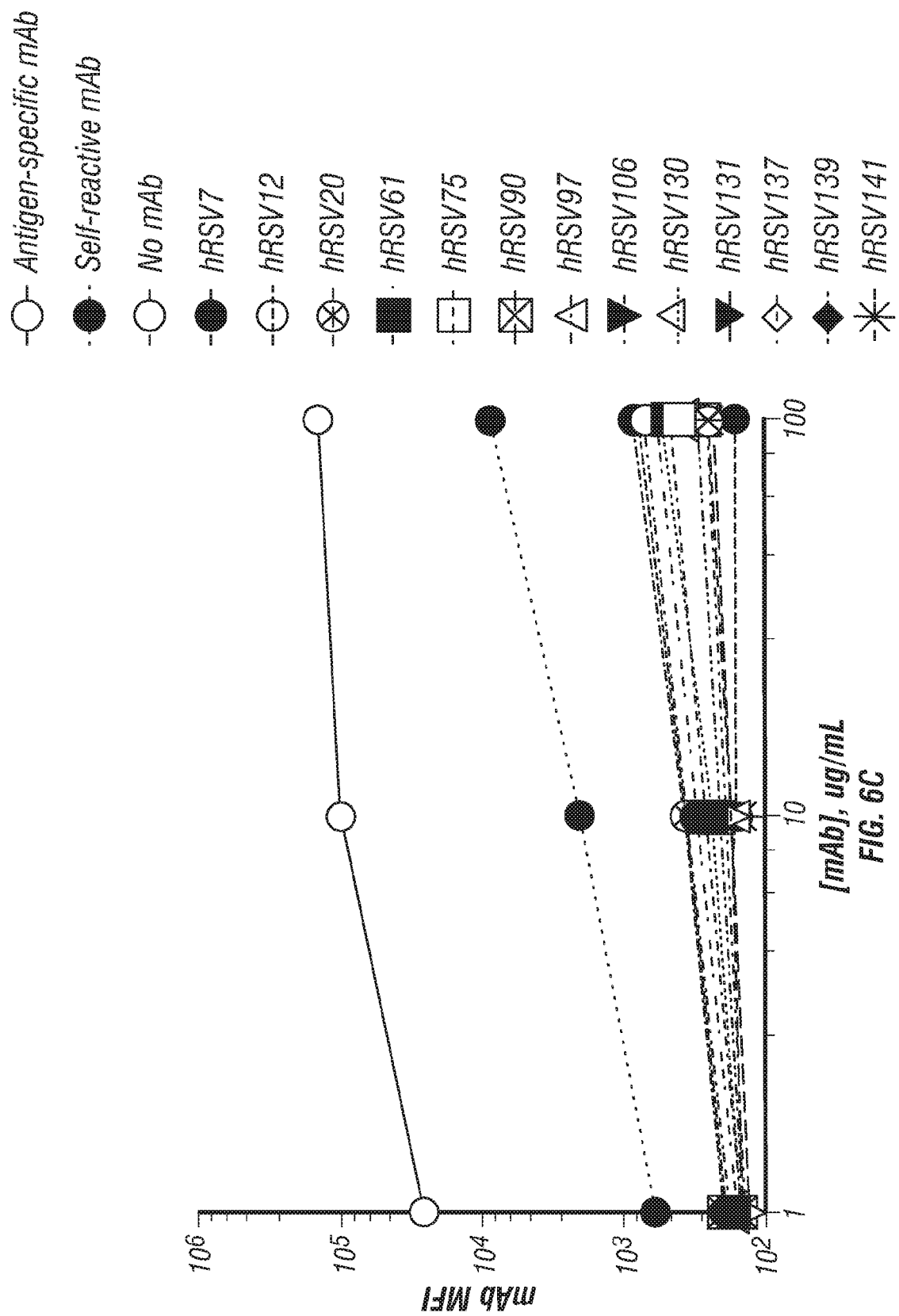

To determine neutralizing potency, the inventors tested the mAbs by plaque-reduction assay using RSV A2 (subgroup A virus), RSV 18537 B (subgroup B virus), and RSV Long (subgroup A virus). Eleven neutralizing mAbs had half-maximal inhibitory concentration ($IC_{50}$) values at or less than 1 μg/mL for RSV A2 (Table 5, FIG. 4). All mAbs also neutralized RSV 18537 B and RSV Long strains, indicating the mAbs have neutralizing breadth across RSV A and B subgroups. The inventors determined half-maximal effective concentration for binding ($EC_{50}$) values by enzyme-linked immunosorbent assay to test the F-protein strain specificity and preference for pre-fusion versus post-fusion F conformations. They used four different proteins in the binding experiments—RSV strain A2 pre-fusion F protein (SC-TM), RSV strain 18537 pre-fusion F (Ds-Cav1), RSV strain A2 post-fusion F, and RSV strain 18537 post-fusion F (Table 5, FIG. 5). Interestingly, all mAbs except hRSV131 and hRSV12 bound specifically to the pre-fusion conformation of F, as binding was not detected for either mAb to post-fusion F proteins from strain A2 or 18537. Furthermore, the mAbs all exhibited cross-reactive binding to F of both RSV subgroup A and B. Cross-reactive pre-fusion conformation-specific mAbs have been reported only in one case, that of the quaternary-epitope dependent mAb AM14 (Gilman et al., 2015). Other pre-fusion specific mAbs, such as D25, bind at antigenic site 0, yet these mAbs are specific for RSV subgroup A. The mAbs hRSV90 and hRSV20 were particularly potent in neutralizing RSV strain A2, with $IC_{50}$ values<40 ng/mL. Seven of the remaining mAbs had neutralizing $IC_{50}$ values less than 370 ng/mL, a level of activity that is similar to, or better than that of, the licensed mAb palivizumab (Group et al., 1998). Binding $EC_{50}$ values were similar for the majority of the neutralizing mAbs, suggesting the binding pose or fine epitope specificity, rather than the affinity, are the principal determinants of differential neutralizing potency. As the isolated mAbs have therapeutic potential for prophylactic treatment of RSV, the inventors tested the mAbs for self-reactivity using a human cell line (Jurkat). None of the mAbs exhibited significant self-reactivity as compared to a known IGHV4-34*01 self-reactive mAb, or to an antigen-specific mAb control (FIGS. 6A-C).

The transcribed antibody heavy and light chain variable genes from hybridoma cell lines were sequenced to determine if there were any common genetic features in transcripts encoding these mAbs. The inventors found remarkable genetic similarities among clones, suggesting common structural features deriving from the germline gene-encoded antibody structures. Two genetic clusters were observed among neutralizing mAbs (Table 6). Four neutralizing mAbs (hRSV90, hRSV20, hRSV130, and hRSV97) were encoded by $V_H3-9*01$. Of these, hRSV90, hRSV20, and hRSV130 used the same $J_H$ gene. Furthermore, hRSV90, hRSV20, and hRSV131 used similar light chain variable gene segments ($V_L13-15*01$ and $J_L4*01$), with all mAbs having nearly identical light chain junction regions. Although hRSV90 and hRSV20 shared nearly identical gene segment usage, the two mAbs likely are not clonal siblings due to a heavy chain complementarity determining region 3 (HCDR3) insertion in hRSV20.

Figure 1:
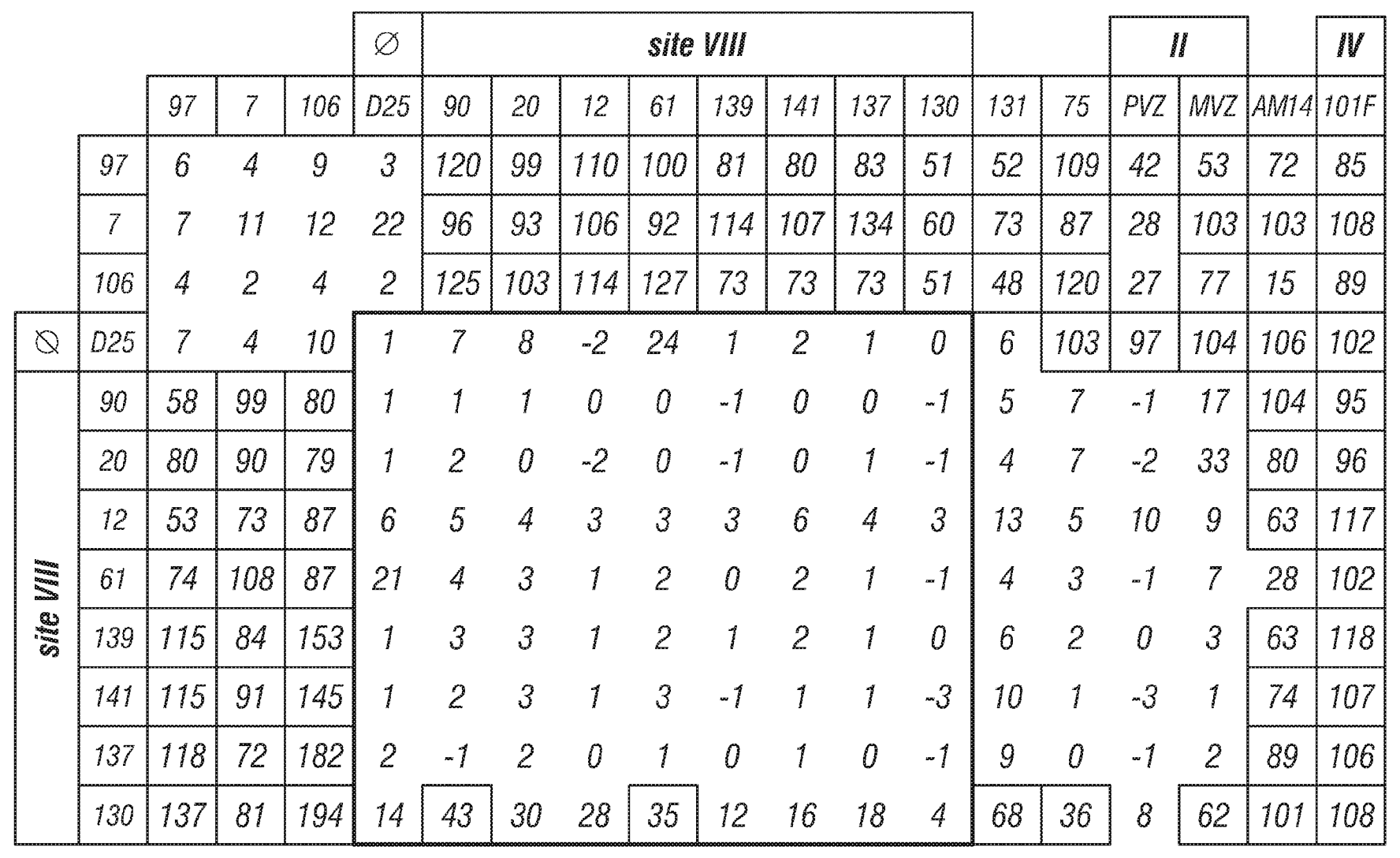

To determine the antigenic sites targeted by the mAbs, the inventors performed epitope binning using biolayer interferometry. RSV A2 F SC-TM protein was loaded onto anti-penta-HIS biosensor tips, and then one RSV mAb was loaded onto the F protein. Following this, a second RSV mAb was loaded, and competition was measured (FIG. 1). Recombinant forms of mAbs D25, palivizumab and motavizumab, and 101F were used as controls in mapping antigenic sites Ø, II, and IV, respectively. Additionally, the trimer-dependent mAb AM14 was used in the study. Interestingly, the inventors discovered a unique competition-binding pattern (and by inference a new antigenic site) for an antibody cluster that competed with both antigenic sites Ø and II, which they designated antigenic site VIII. Antigenic sites Ø and II are over 40 Å apart in the RSV F SC-TM structure (PDB: 5C6B), yet antigenic VIII site evidently possesses residues in or near both sites Ø and II, as strong competition was observed between site VIII-specific mAbs and palivizumab/motavizumab. Several of the new mAbs also competed with AM14, suggesting binding near the antigenic region for that mAb. It is worth noting that three of the new pre-fusion F-specific mAbs isolated (designated hRSV97, hRSV7, and hRSV106) showed competition for binding with palivizumab/motavizumab but did not compete with mAbs in the antigenic site VIII competition block. This finding suggests that the mAbs target an alternate antigenic site. The mAbs hRSV75, 131, and AM14 competed for binding with the antigenic site IV mAb 101F in addition to competing for mAbs at site VIII. As expected, hRSV90 and hRSV20 exhibited similar competition-binding patterns, consistent with the identical gene usage among these mAbs. $V_H1-18*01$ gene-encoded mAbs hRSV12, hRSV61, hRSV139, and hRSV131 also showed similar competition-binding patterns with $V_H3-9*01$ gene-encoded mAbs hRSV90 and hRSV20. Interestingly, mAbs hRSV131 and hRSV12 shared similar gene usage to hRSV61 and hRSV139, yet the former bind both pre- and post-fusion conformations of F protein, suggesting subtle changes caused by somatic mutations in the differing recombined genes incorporating $V_H1-18*01$ and/or differing light chain genes altered mAb specificity and created an antigenic site VIII mAb that has both pre- and post-fusion F binding capacity. It is worth noting that hRSV131 showed appreciable binding to the metapneumovirus fusion protein This unusual cross-reactive binding pattern, coupled with the epitope binning data, suggest the mAb may hind at a similar location to the previously described human mAb MPE8 (Corti et al., 2013).

Figure 7C:
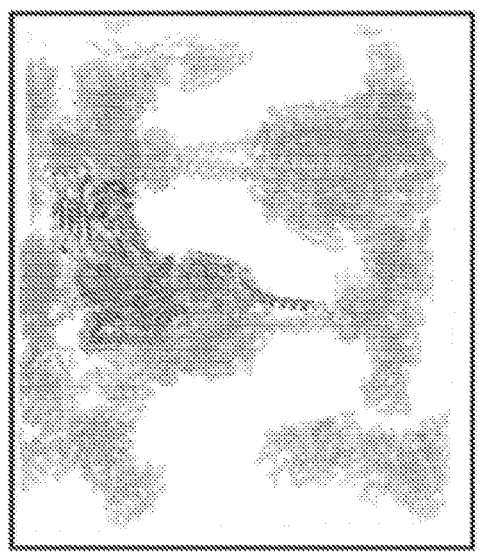
FIGS. 7A-C. Density maps for the hRSV90-RSV F A2 SC-TM interface.
Figure 7B:
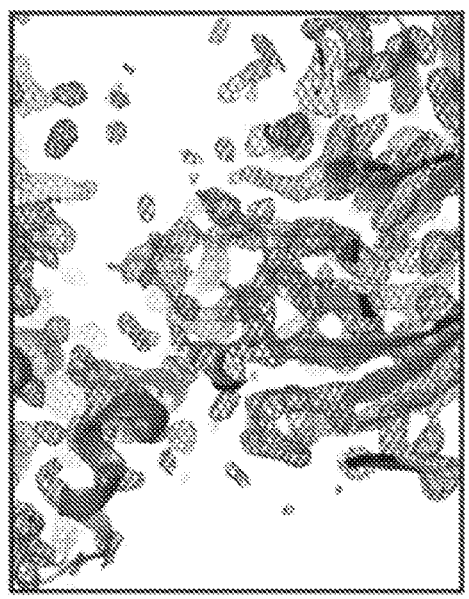
Figure 7A:
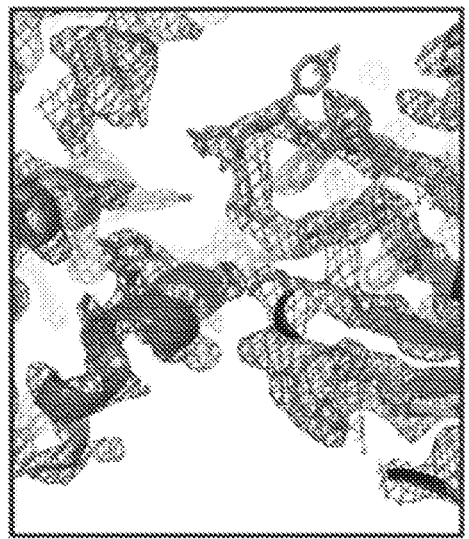

To characterize the newly identified antigenic site VIII further, the inventors determined the X-ray crystal structure of the most potently neutralizing mAb, hRSV90, in complex with pre-fusion RSV A2 F SC-TM protein. hRSV90 Fab was obtained by papain cleavage from the hybridoma-secreted IgG, complexed with pre-fusion F protein, and purified by size-exclusion chromatography. The Fab-F complex eluted in one band, and crystals formed in several conditions including: 1.5 M $LiSO_4.H_2O$/100 mM HEPES pH 7.5, and 20% PEG 550 MME/100 mM NaCl/100 mM BICINE pH 9.0. The largest and best diffracting crystals were obtained in 30% PEG 400/200 mM $MgCl_2.6H_2O$/100 mM HEPES pH 7.5. The diffraction was significantly anisotropic, so the processed data was submitted to the diffraction anisotropy server (Strong et al., 2006), which gave a=3.6, b=3.6, and c=3.1. The structure was solved to 3.1 Å ($R_{work}/R_{free}$=22/26%) using molecular replacement with the RSV A2 F SC-TM structure (PDB: 5C6B) and an alanine truncated Fab structure (PDB: 4Q9Q) as search models (Table S1). Density for the Fab was observed at the interface between antigenic sites Ø and II, consistent with the competition-binding data, and identified a novel antigenic site that is the target of potently neutralizing antibodies (FIGS. 7A-C).

Figure 2B:
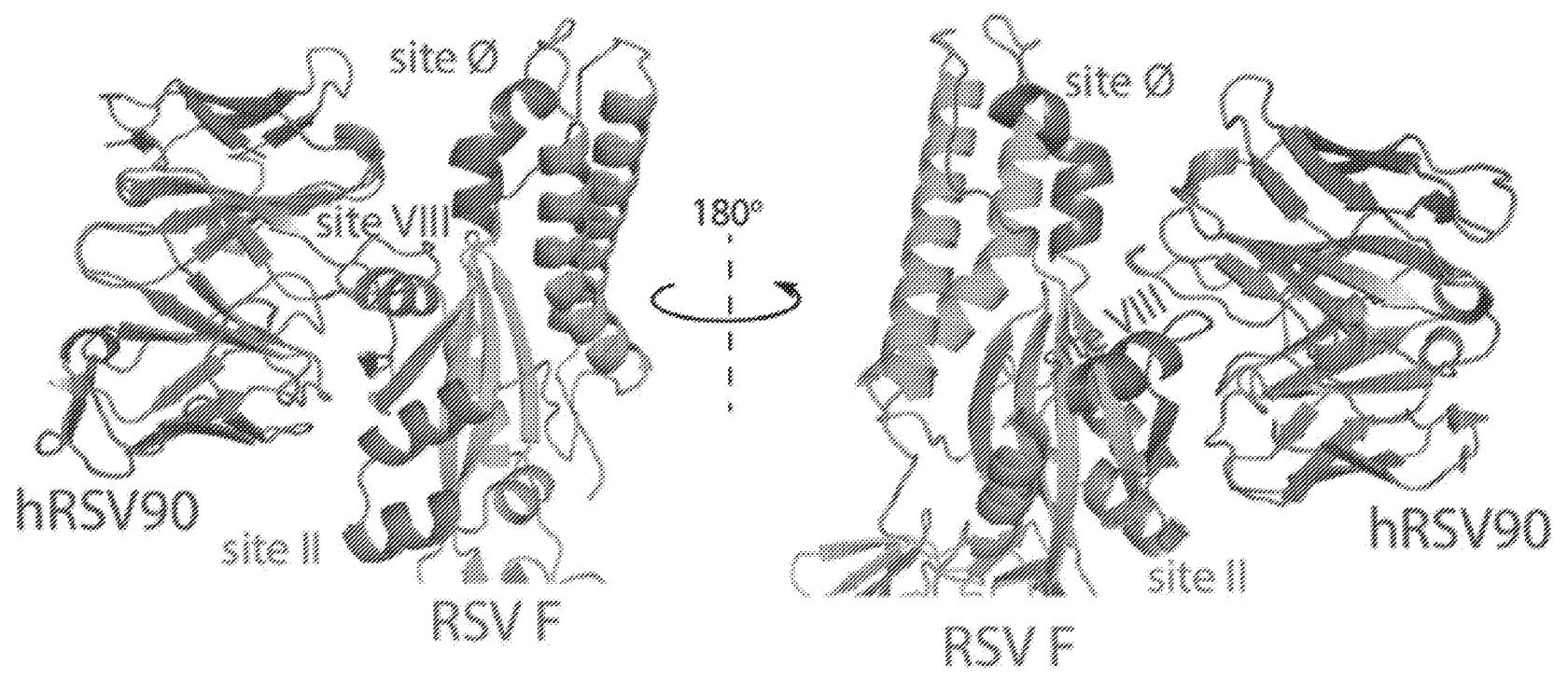
Figure 3A:
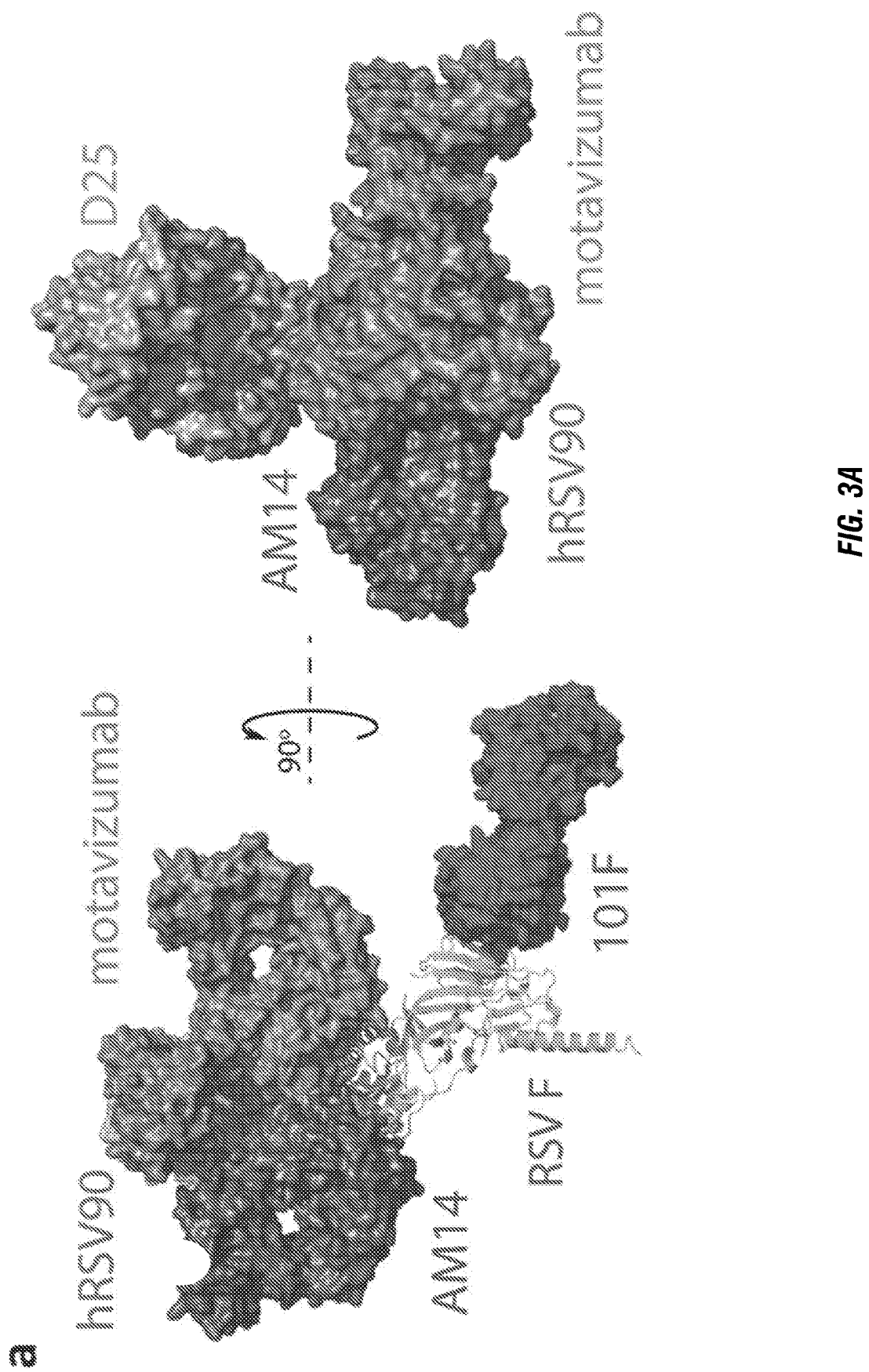
FIGS. 3A-C. Comparison between hrSV90 and known antigenic sites and interactions between hrSV90 and prefusion RSV F.
Figure 3B:
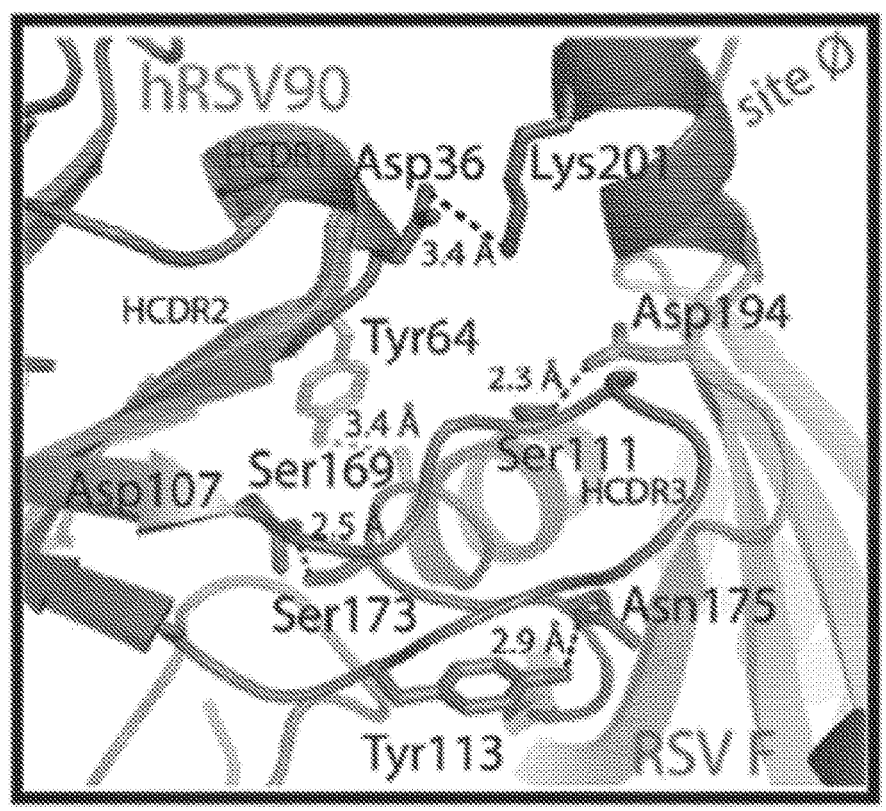
Figure 3C:
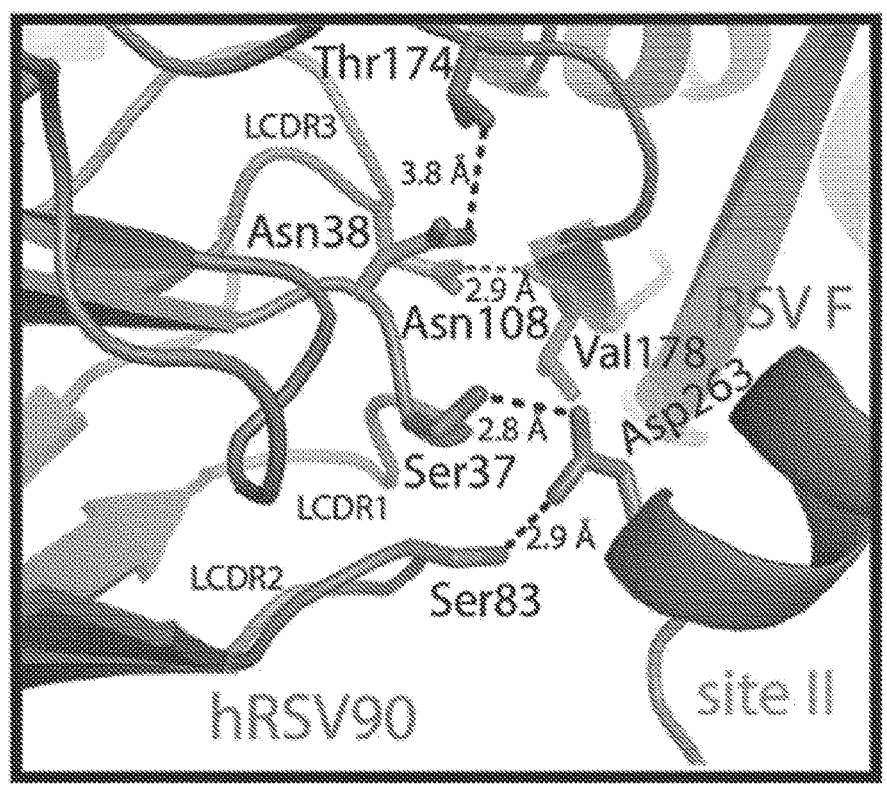
Figure 8A:
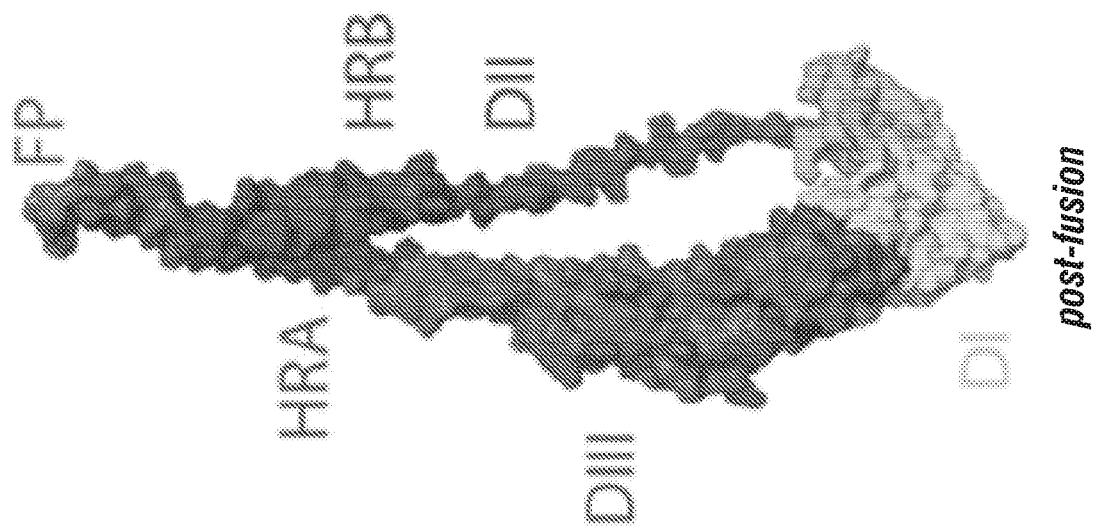
FIGS. 8A-B. Structural and antigenic regions of the RSV F protein.
Figure 8A:
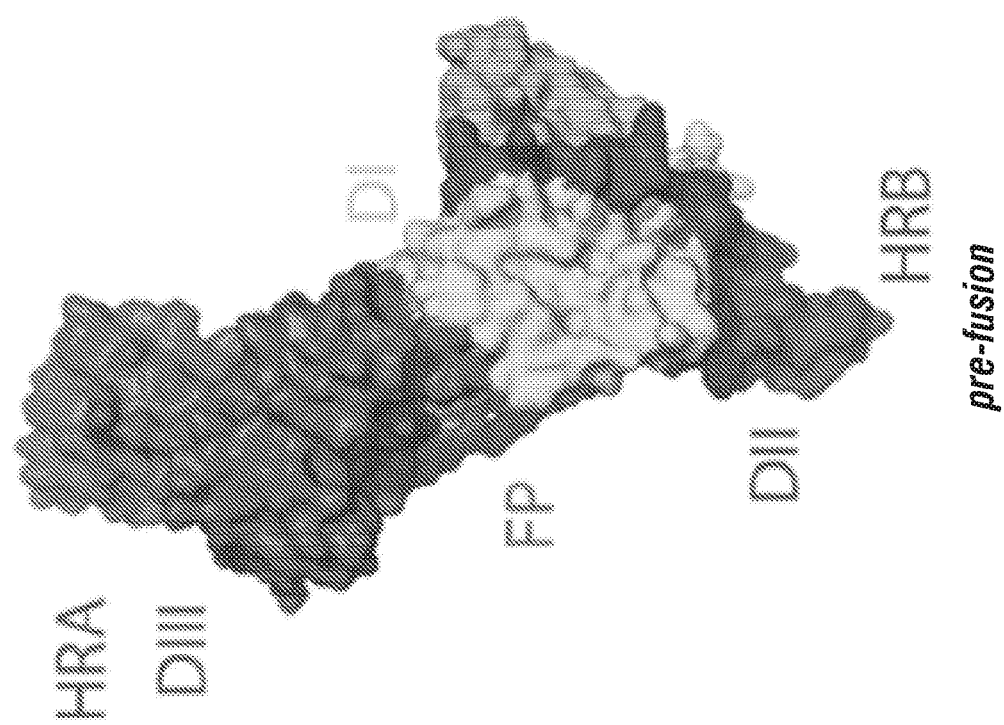
Figure 8B:
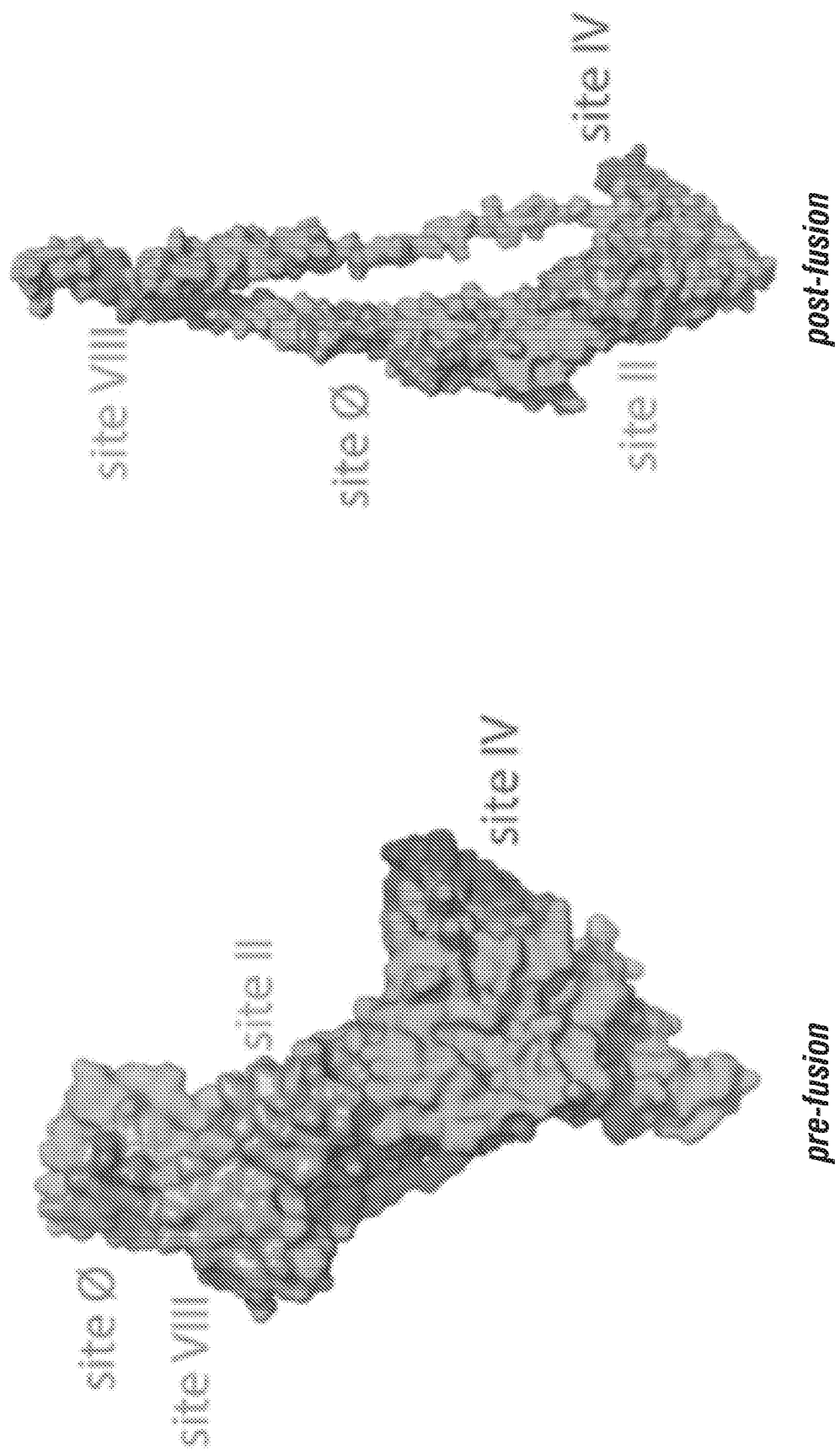

The asymmetric unit contained one RSV F protomer and one hRSV90 Fab molecule, and the complex crystallized in a trimer based on the position of symmetry related partners (FIG. 2A). The trimerization domain of the recombinant F protein was clearly visible in the electron density (FIGS. 7A-C). The three hRSV90 Fabs in the trimer structure are distant from each other, and each Fab interacts only with one protomer of F, suggesting hRSV90 is not trimer-specific. hRSV90 is positioned approximately 30° upward from the horizontal F axis, engaging only the top 37 Å of the F protein. When viewed from the top-face, the three Fabs radiate outward from the RSV F trimer, engaging a 35 Å surface (FIG. 2A). hRSV90 binds to RSV F primarily through the "helix-loop-sheet" motif at residues 163-181 (FIG. 3B). The Fab uses an eighteen residue HCDR3 that is bulged at the torso and that inserts itself between antigenic sites Ø and II at the helix-loop-sheet motif. The hRSV90 heavy chain interacts with residues 163-181 and site Ø, while the light chain interacts with 163-181 and site II. hRSV90 interacts only with the DIII domain of RSV F (FIG. 8A). The helix-loop-sheet residues are rearranged in the post-fusion conformation, forming part of the extended helix of the heptad repeat A portion (FIG. 8B). This rearrangement explains the pre-fusion specificity of hRSV90 and similar mAbs described here, as the primary antigenic region is absent in the post-fusion conformation. This property is similar for mAb D25, as the site Ø antigenic region is rearranged in post-fusion RSV F.

Figure 9A:
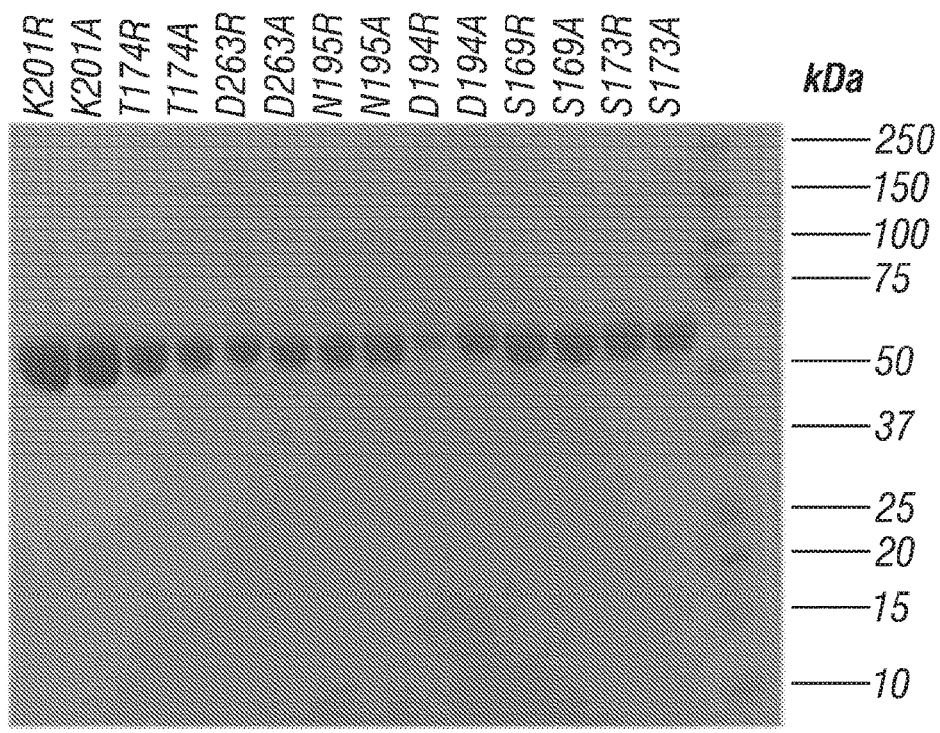
FIGS. 9A-B. RSV F SC-TM mutants.
Figure 9B:
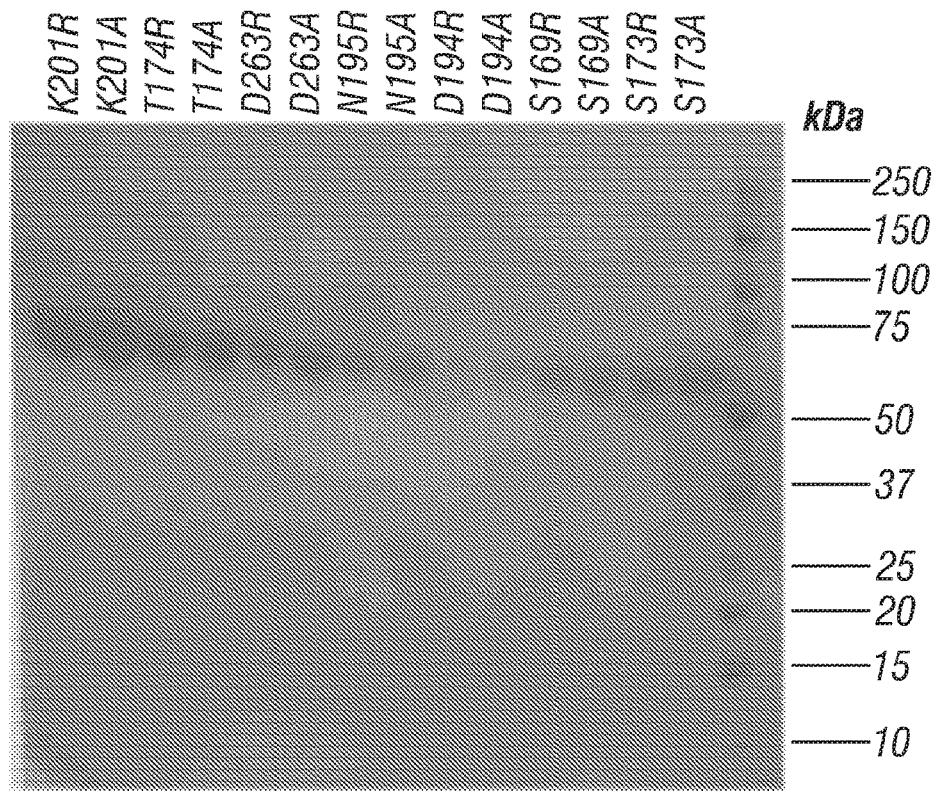
Figure 10:
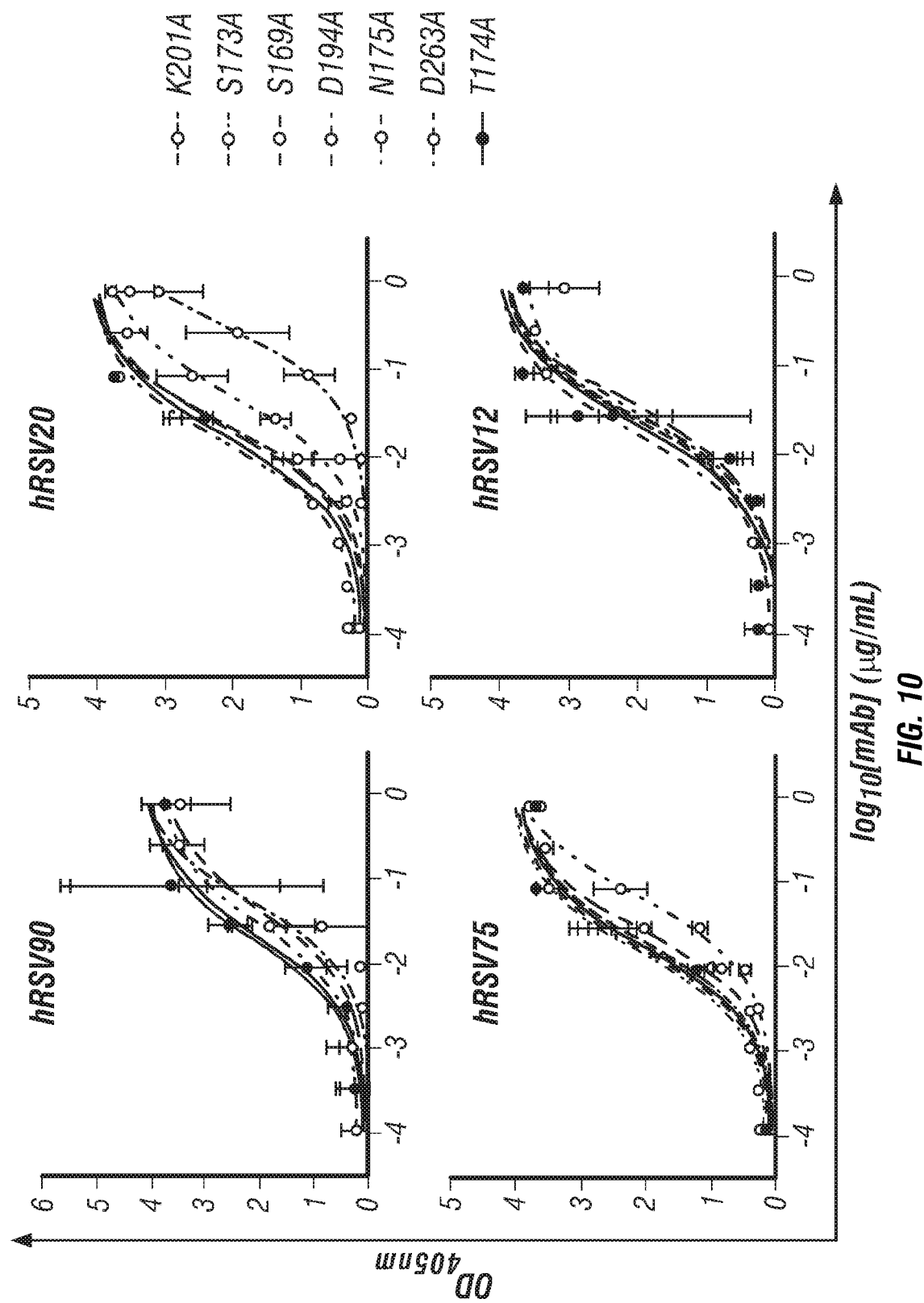
FIG. 10. ELISA binding curves for RSV F SC-TM alanine mutations at the hRSV90 binding site. Error bars indicate 95% confidence intervals, n=4.
Figure 10:
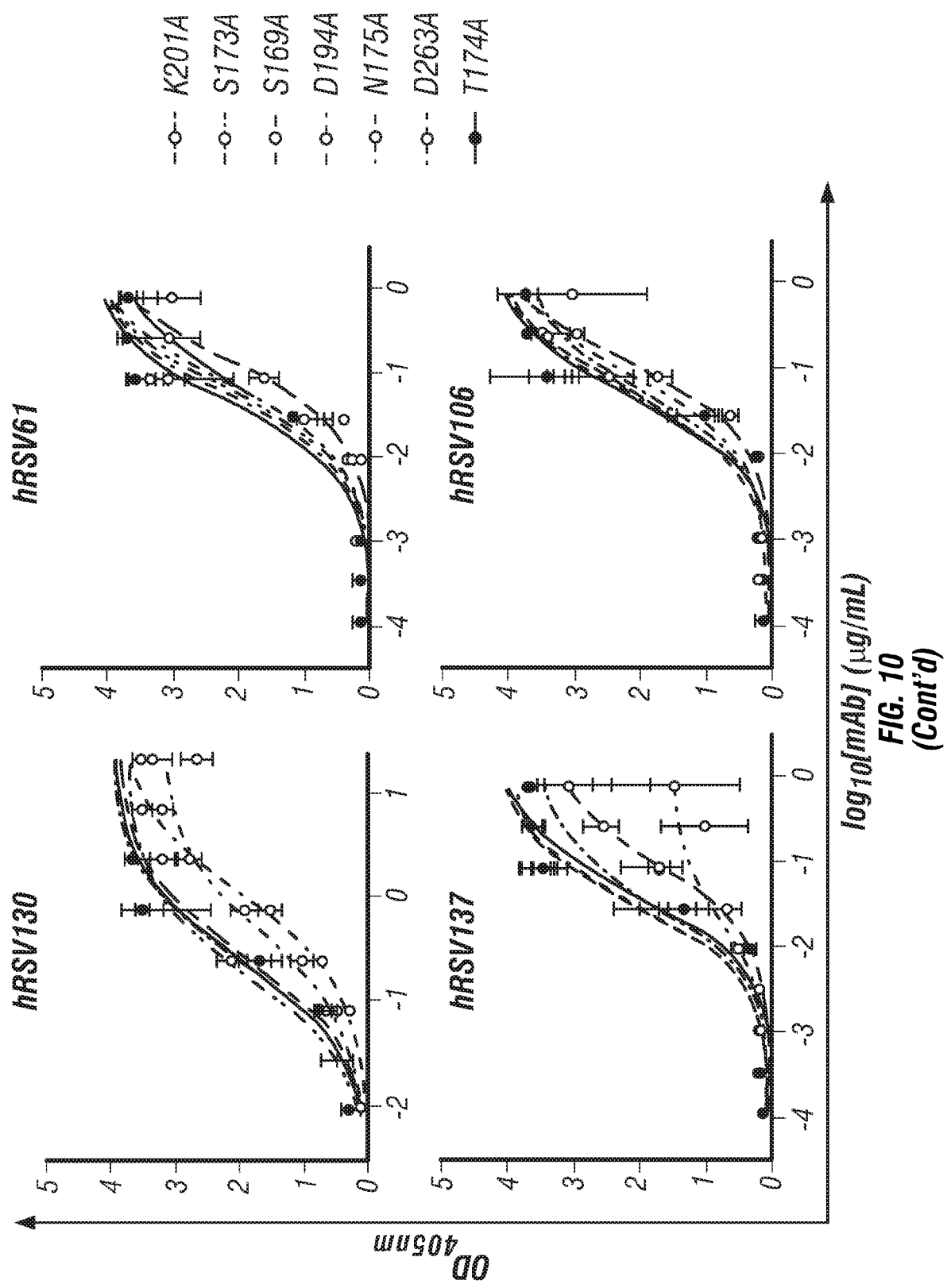
Figure 10:
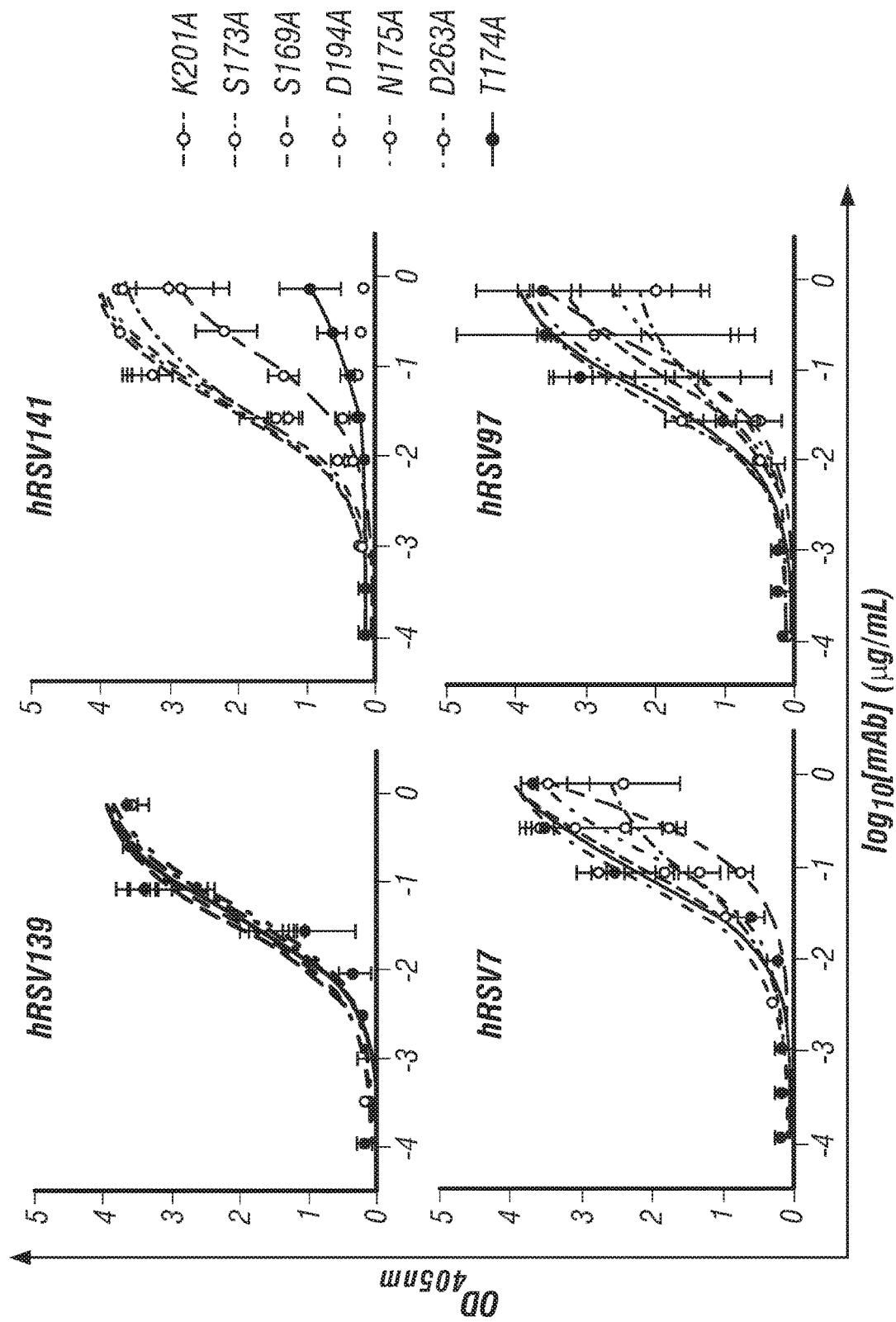
Figure 10:
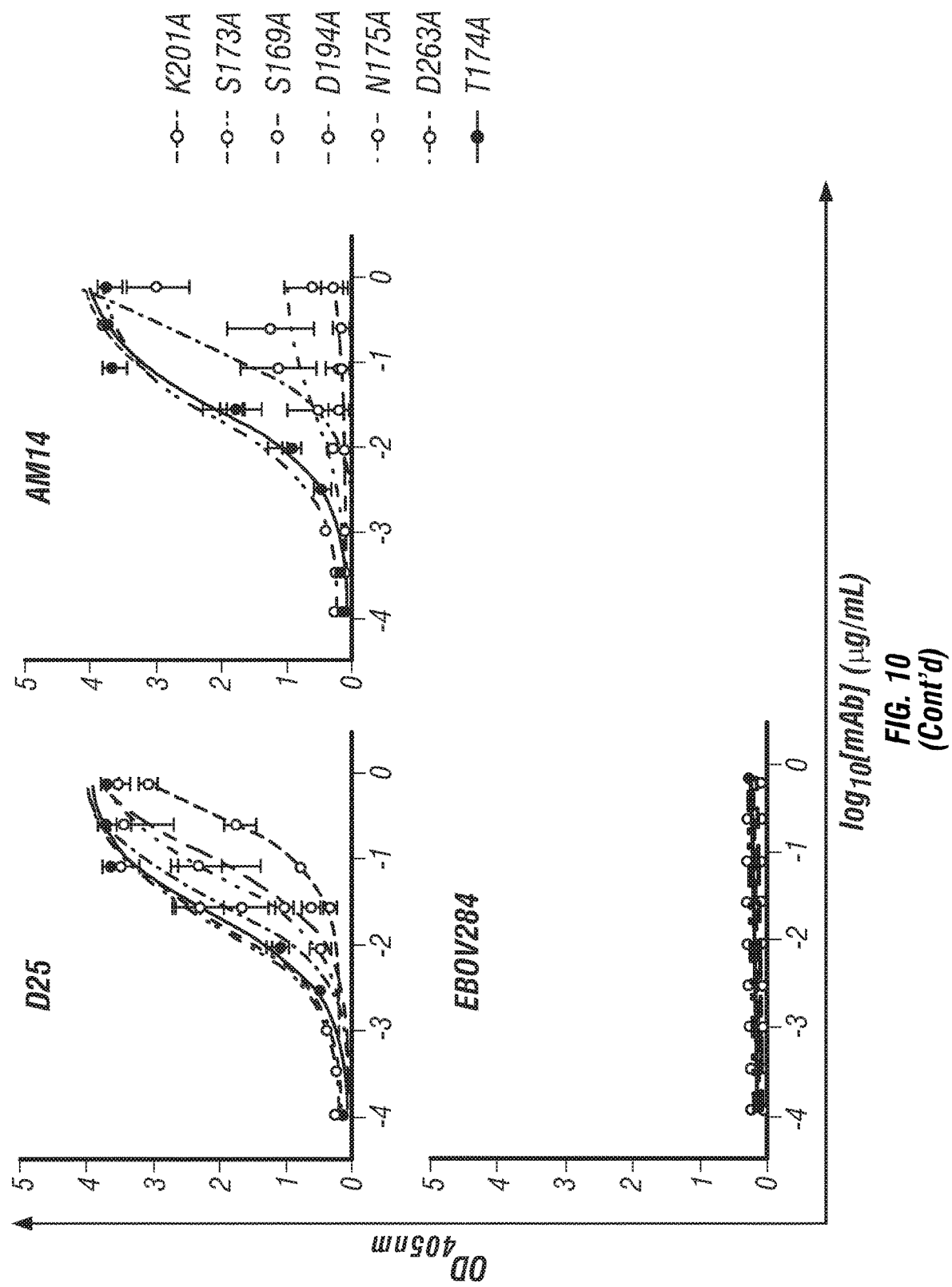
Figure 11:
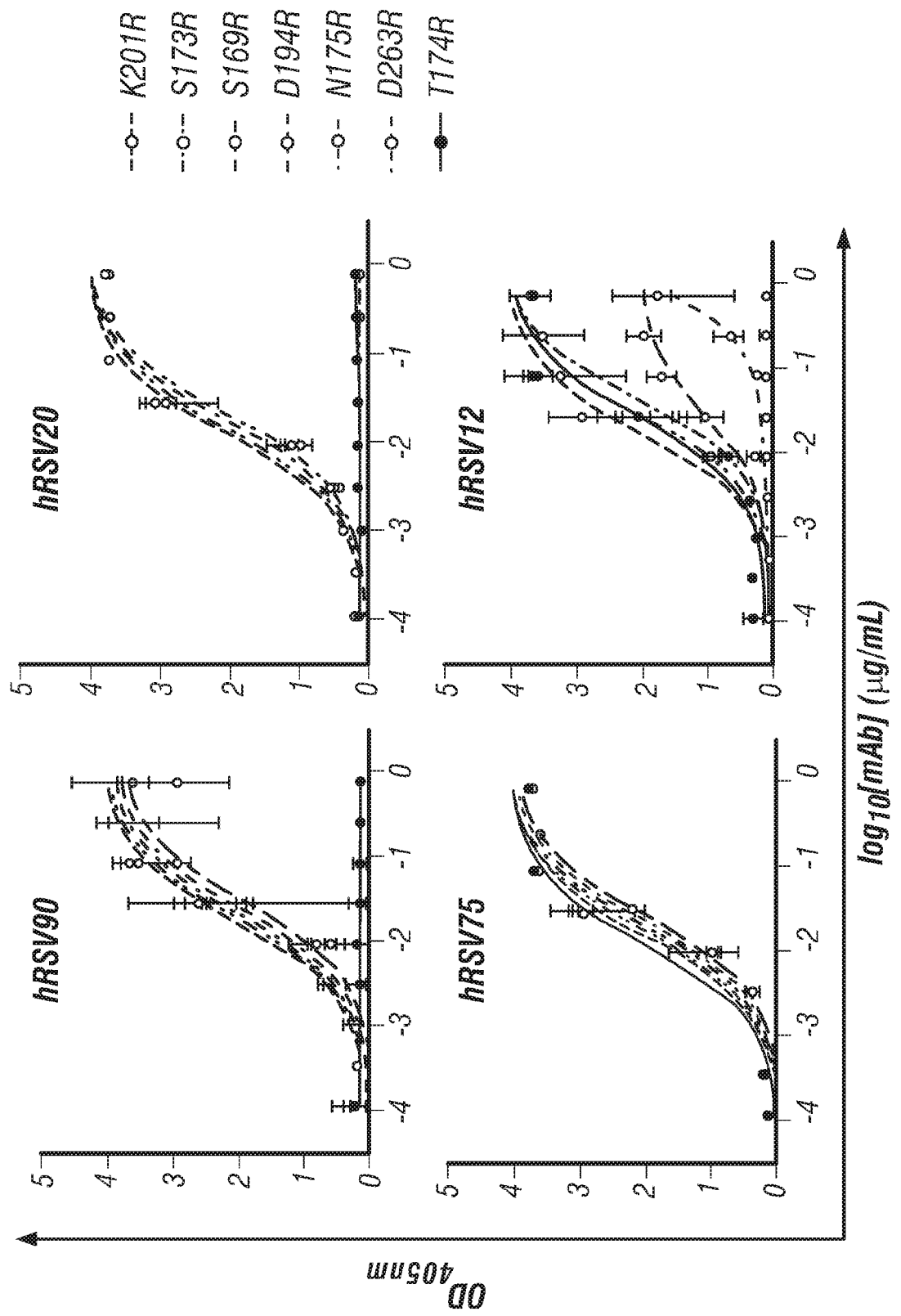
FIG. 11. ELISA binding curves for RSV F SC-TM arginine mutations at the hRSV90 binding site. Error bars indicate 95% confidence intervals, n=4.
Figure 11:
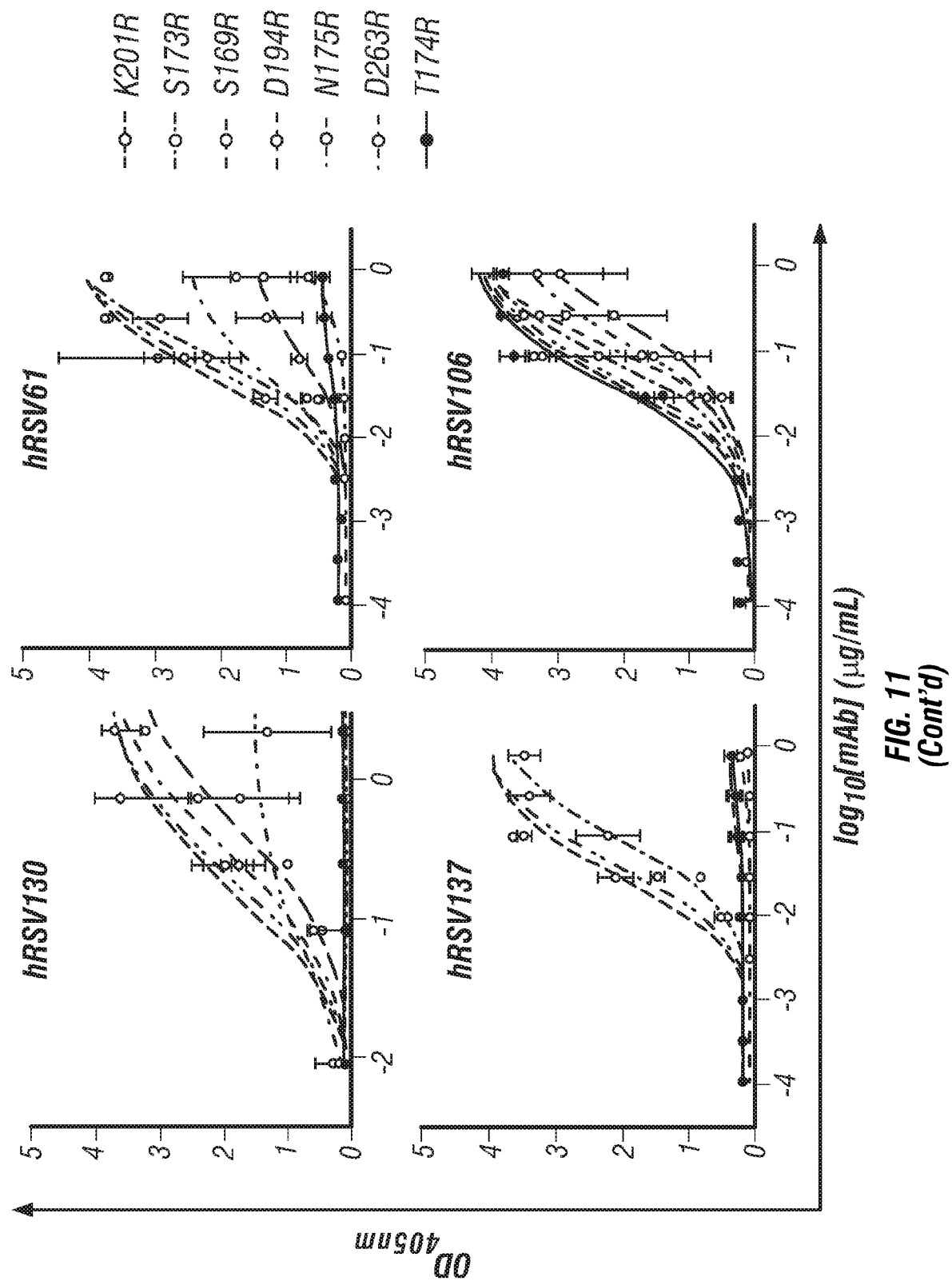
Figure 11:
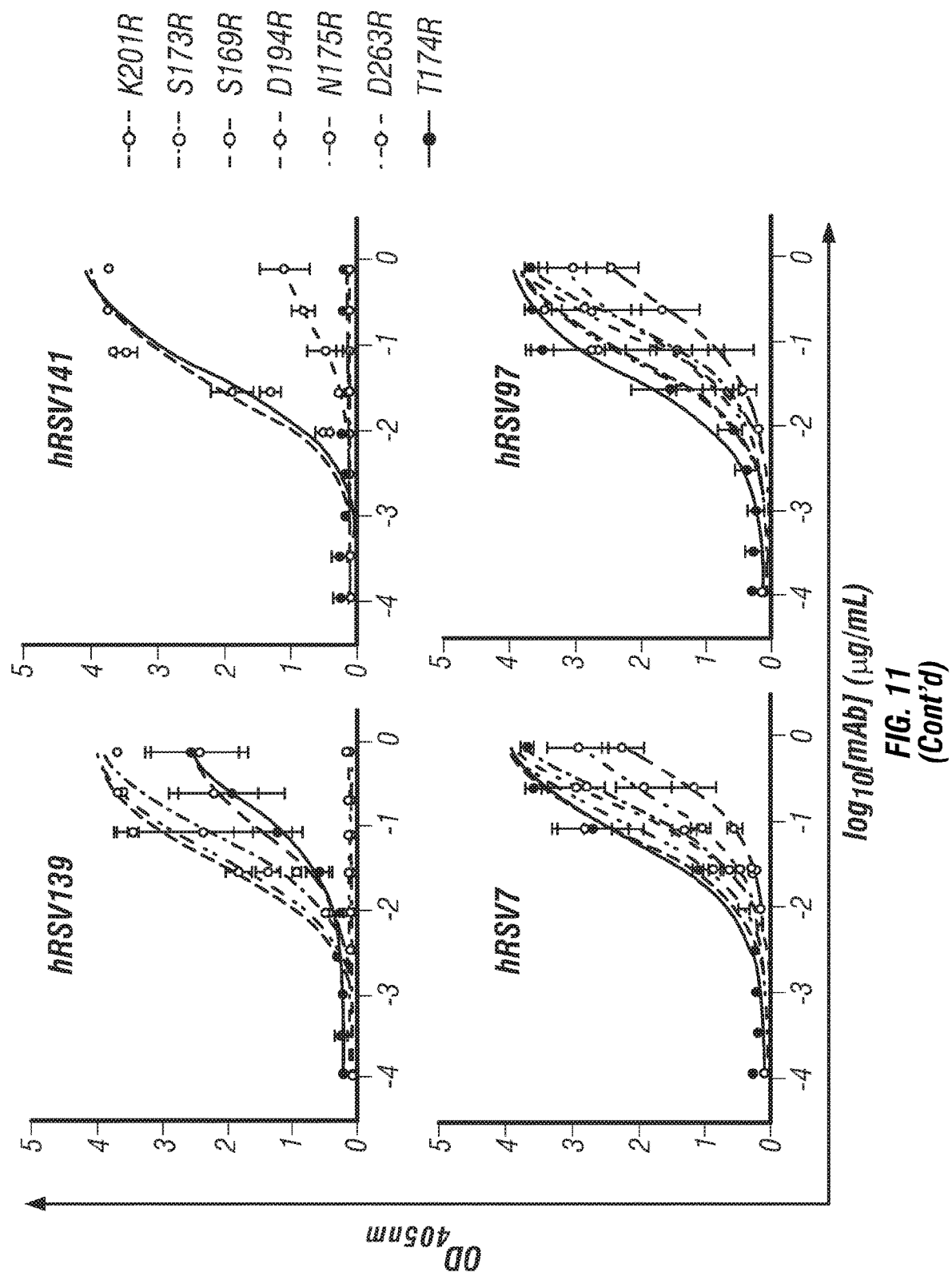
Figure 11:
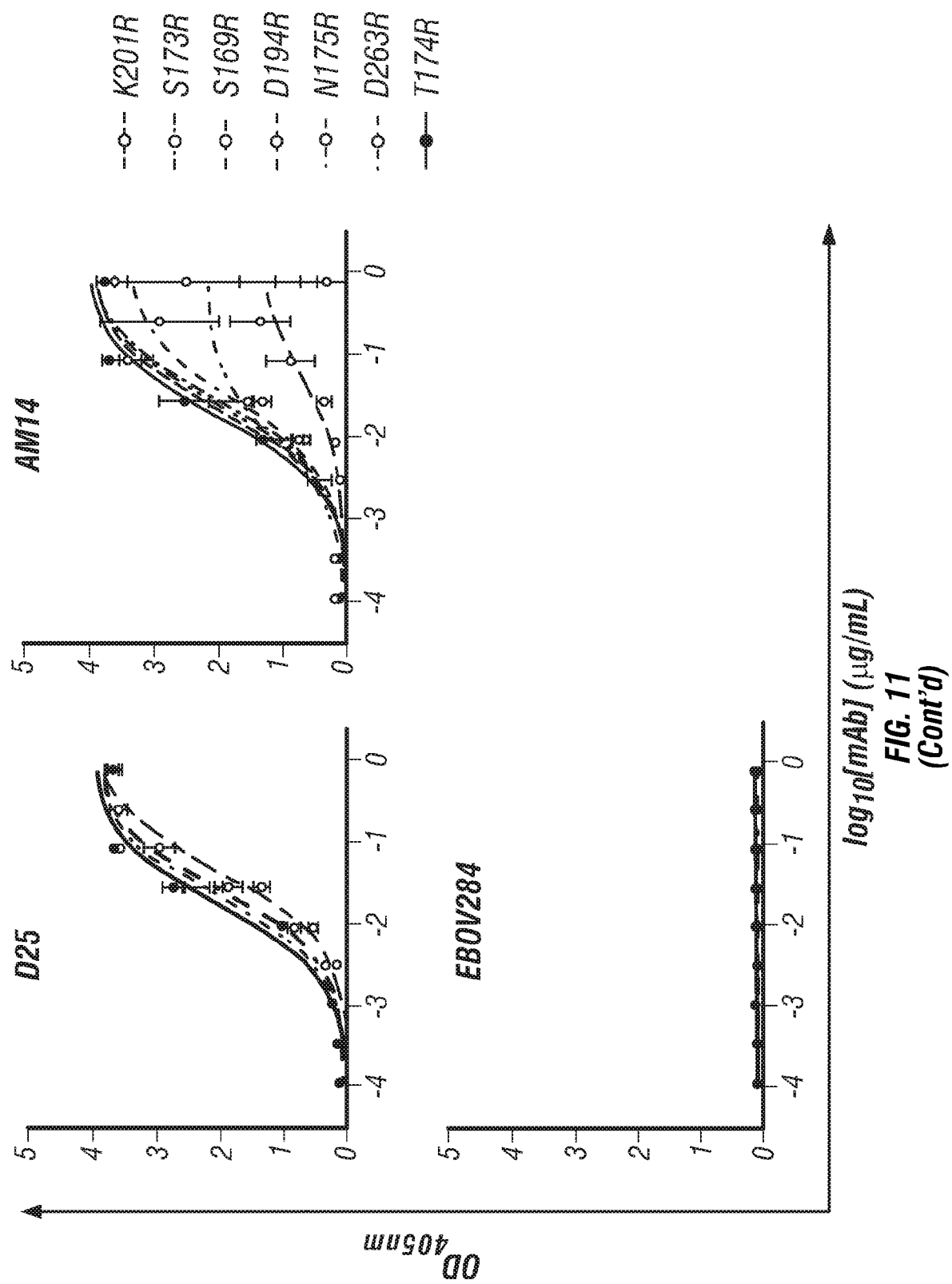

When comparing previously described antigenic sites to site VIII, hRSV90 is nestled between sites II and Ø, and also in close proximity to the trimer-dependent mAb AM14 site, while being distant from 101F at antigenic site IV. While AM14 and motavizumab bind at opposite interfaces of the RSV F protein in an orientation that is approximately parallel, hRSV90 is turned nearly 90°, engaging with RSV F at a perpendicular orientation. When observing the antigenic overlay from the apex, bound hRSV90 sits in between bound AM14 and motavizumab on F, while being shifted 80° downward from D25 (FIG. 9A). hRSV90 uses the heavy chain to interact with antigenic sites VIII and Ø, binding at the interface between the two sites. The HCDR3 sits perpendicular to the long-axis of the RSV F protein, on top of site VIII. The torso of the HCDR3 interacts with site VIII through Asp107, hydrogen bonding to the loop residue Ser173 (FIG. 9B). The HCDR3 contains multiple Tyr residues, however, only Tyr113 is involved in hydrogen bonding, interacting with Asn175, also on the loop portion of antigenic site VIII. Tyr109 and Tyr112.1 are pointed directly toward the RSV F protein, but they do not interact directly with the protein. Possibly these Tyr residues are involved in indirect bonding through water molecules, but this mode of interaction is unclear in the 3.1 Å resolution structure. The inventors considered whether the Tyr residues were post-translationally modified by sulfation, but they did not observe density for sulfate at the tyrosine residues. HCDR3 Ser111 hydrogen bonds to Asp194 just below site Ø. Additional interactions are present with RSV F through the HCDR2 and HCDR1. The HCDR2 interacts with the helix of site VIII by hydrogen bonding to Ser169 through Tyr64.

A single distant interaction with site Ø is mediated by the CDR1 residue Asp36 to RSV F Lys201. While the heavy chain interacts with site VIII and site Ø, the light chain interaction provides the basis for hRSV90 competition with antibodies that recognize antigenic site II (FIG. 9C). Both the light chain CDR2 (LCDR2) and LCDR1 are in sufficiently close proximity to hydrogen bond with site II residue Asp263 via interactions with Ser83 and Ser37, respectively. A further hydrogen bond from LCDR1 Asn38 allows interaction with the site VIII loop residue Thr174. Furthermore, the single site VIII sheet direct hydrogen bond is provided by LCDR3 Asn108 interacting with the backbone carbonyl of Val178.

In order to confirm the X-ray structure and determine critical residues responsible for hRSV90 binding to RSV F, the inventors mutated each of the contact residues observed in the X-ray structure (Table 7, FIGS. 9A-12). Surprisingly, mutating individual residues to alanine showed no significant effect on hRSV90 binding. To probe the interactions further, the inventors mutated each residue to arginine to test for steric effects. All site VIII mAbs identified from epitope binning showed loss of binding for one or more mutants, confirming the site of binding region for these mAbs. Mutant Ser173Arg (interacting with hRSV90 HCDR3) resulted in loss of binding for hRSV90, hRSV20, and hRSV130. Mutant Thr174Arg (interacting with hRSV90 LCDR3) caused loss of binding for mAbs hRSV90, hRSV20, hRSV130, hRSV61, hRSV137, and hRSV141. MAbs clustered outside site VIII from epitope binding experiments (hRSV97, hRSV7, hRSV106, hRSV131, and hRSV75) retained binding in all tested mutants, also confirming the uniqueness of antigenic site VIII. The inventors did observe significant loss of binding for mAb D25 when mutating the site Ø residue Lys201Ala, and this binding was rescued in the Lys201Arg mutation. The epitope for AM14 was previously determined using MARM generation, which showed Leu160Ser and Asn183Lys mutations, among others. Asn183 is positioned at the end of the loop of the site VIII epitope, and does not interact with hRSV90.

The protein sequence in the site VIII epitope is highly conserved in field isolates between RSV A and B subgroups (FIG. 12), similar to antigenic sites II and IV. The X-ray structure of hRSV90 with RSV F defines the structural basis for the newly discovered antigenic site VIII. The most potently neutralizing RSV mAbs previously described include those at antigenic site Ø, a pre-fusion specific epitope. The inventors provide new insight into a novel pre-fusion conformation-specific major antigenic site residing between antigenic sites Ø and II. The isolated mAbs are comparable to the best-in-class RSV antibodies described to date in terms of binding and neutralization. This new antigenic site likely has been unrecognized previously due to the majority of human antibody experiments using polyclonal serum. Indeed, when measuring serum antibody competition-binding to site Ø or site II, the activity of antibodies binding to antigenic site VIII may have been grouped into one or the other sites. However, site VIII contains unique epitopes for potently neutralizing antibodies. Further experimentation likely will identify additional mAbs targeting the site VIII epitope. Site VIII also induces broadly cross-reactive F protein antibodies that recognize both subgroups of RSV. The previously discovered cross-reactive mAb AM14 provides the same cross-reactive response, however, site VIII resides on one protomer. This characteristic of site VIII may prove useful for future structure-based vaccine designs, since highly quaternary sites comprising domains from multiple protomers are difficult to recapitulate with synthetic antigens.

TABLE 1

NUCLEOTIDE SEQUENCES FOR ANTIBODY VARIABLE REGIONS

| Clone | Variable Sequence Region | SEQ ID NO: |
|---|---|---|
| 90 heavy | GAAGTGCAGCTGGTGGAGTCTGGGGGAGGCTTGGTACAGCCTCGCAGGTCCCTGAGAC<br>TCTCCTGTGCAGCCTCTGGATTCACCTTTGATGATTATACCATACACTGGGTCCGCCA<br>AGCTCCAGGGAAGGGCCTGGAGTGGGTCTCAGGTATTACTTGGAATAGTGGTTACATT<br>GGCTATGCGGACTCTGTGAAGGGCCGATTCACCATCTCCAGAGACAACGCCAGGAACT<br>CCCTGTATCTGCAAATGAACAGTCTGAGAGCTGAGGACACGGCCTTGTATTACTGTGT<br>AAGAGATGCCTATGTTTCGGGGAGTGATTACTACTACTACGGTTTGGACGTCTGGGGC<br>CGAGGGACCCTGGTCACCGTCTCCTCA | 1 |
| 90 light | GAAATAGTGATGACGTCGTCTCCAGCCACCCTGTCTGTGTCTCCAGGGGAAAGAGCCA<br>CCCTCTTTTGCAGGGCCAGTCAGAGTGTGATCAGCAACTTAGCCTGGTACCAGCAGAA<br>ATCTGGCCAGGCTCCCAGGCTCCTCATCTATGGTGCATCCACCAGGGCCACTGGTATC<br>CCAGCCAGGTTCAGTGGCAGTGGGTCTGGGACAGAGTTCACTCTCACCATCAGCAGCC<br>TACAGTCTGAAGATTTTGCAGTTTATTTTTGTCAGCAGTATAATAACTGGCCTCTCAC<br>TTTCGGCGGAGGGACCCAGGTGAACGTCCAAA | 2 |
| 20 heavy | CAAGTGCAGCTGGTGGAGTCTGGGGGAGGCTTGGTACAGCCTGGCAGGTCCCTGAGAC<br>TCTCCTGTGCAGCCTCTGGATTCACCTTTGATGATTATGCCATGCACTGGGTCCGGCA<br>AGCTCCAGGGAGGGCCTGGAGTGGGTCTCAGGTATTAGTTGGAATAGTGGTATCGCA<br>GTCTATGCGGACTCTGTGAAGGGCCGATTCACCATCTCCAGAGACAACGCCAAGAAT<br>CCCTGTATCTGCAAATCAACAGTCTGAGAGCTGAGGACACGGCCTTGTATTACTGTGT<br>AAAAGATAACTATGCTTCGGGGAGTTATTCTTCTTACTACTACTACGGTCTGGAC<br>CTCTGGGGCCAAGGGACCCTGGTCACCGTCTCCTCA | 3 |
| 20 light | GAAATTGTGATGACTCAGTCTCCAGCCACCCTGTCTGTGTCTCCAGGGGAAAGAGCCA<br>CCCTCTCCTGCAGGGCCAGTCAGAGTATTATCAGCAACTTAGCCTGGTACCAGCAAAA<br>ACCTGGCCAGGCTCCCAGGCTCCTCATTTATGGTGTATCCACCAGGGCCACTGGTATC<br>CCAGCCAGGTTCAGTGGCAGTGGGTCTGACACAGAGTTCACTCTCTCCATCAGCAGCC<br>TGCAGTCTGAAGATTTTGCAGTTTATTACTGTCAGCAGTATAATAACTGGCCGATCAC<br>CTTCGGCCAAGGGACACGACTGGAGATTAAAC | 4 |
| 130 heavy | NNNGTGCAGCTGGTGCAGTCTGGGGGAGGCCTGGTACAGCCTGGCAGGTCCCTGAGAC<br>TCTCCTGTAGAGCCTCTGGATTTAGATTTGATGATTACGCCATGCACTGGGTCCGGCA<br>AGTTCCAGGGAAGGGCCTGGAGTGGGTCTCAGGTATCAGTTGGCACAGTGGTCATAGA<br>GACTATGCGGACTCTGTGAAGGGCCGATTCACCATCTCCAGAGACAACGCCAAGAATT<br>CCCTGTATCTAGAAATGAACAGTTTGAGAGCTGAGGACACGGCCTTGTATTATTGTGT<br>AAAAGACAGTCACTATTTTGATAATAGTGGTTCTTATACCTATGGTTTGGATGTCTGG<br>GGCCAAGGGACCCTGGTCACCGTCTCCTCA | 5 |
| 130 light | CAGNTTGTGATGACTCAGTCTCCAGCCACATTGTCTGTGTCTCCAGGGGAAAGAGCCA<br>CCCTCTCCTGCAGGGCCAGTCAGAGTGTTCTCAGCAACTTAGCCTGGTACCAGCAGAA<br>ACCTAGCCAGGCTCCCAGGCTCCTCATCTATGGAGCATCTGCCAGGGCCACTGGTATC<br>CCAGCCAGGTTCAGTGGCAGTGGGTCTGGGACAGACTTCACTCTCACCATCAGCAGCC<br>TGCAGTCTGAAGATTTTGCAGTCTATTACTGTCAGCAGTATAATAATTGGCCTCTCAC<br>TTTCGGCGGAGGGACCAAGGTGGAGATCAAG | 6 |
| 61 heavy | CAGGTGCAGCTGGTGCAGTCTGGAGCTGAGCTGAAGAAGCCTGGGGCCTCAGTGAAGG<br>TCTCGTGCAAGGCTTCCGGTTACACCTTTACCAATCATGGTATCACCTGGGTGCGACA<br>GGCCCCTGGACAAGGGCTTGAGTGGATGTCATGGATCAGCGGTTACAATGGTAACACA<br>CAGTATGCACAGAAGTTCCAGGGCAGAGTCACCATGACCACAGACACATCCACGAGGA<br>CGGCCTACATGGAGTTGAGGAGCCTGACATCTGACGACACGGCCGTCTATTATTGTGC<br>GAGAGACAATGGAGTCGTAGTGGGACCTCCCGACTACTGGGGCCAGGGAACCCTGGTC<br>ACCGTCTCCTCAG | 7 |
| 61 light | GACATCCAGATGACCCAGTCTCCTTCCACCCTGTCTGCATCCGTAGGAGACAGAGTCA<br>CCATATCTTGCCGGGCCAGTCAGAGTATTAGTAGCTGGTTGGCCTGGTATCAGCAGAA<br>ACCAGGGAAACCCCCTAAACTCCTGATCTATAAGGCGTCCGGTTTACAAACTGGGGTC<br>CCATCAAGGTTCAGCGGCAGTGGATCTGGGACAGAATTCACTCTCACCATCAGCAGCC<br>TGCAGCCTGATGATTTTGCAACTTATTACTGCCAATATTATCATAGTCTTTCGGCTTT<br>CGGCCAAGGGACCAAGGTGGAAATCAAAC | 8 |
| 7 heavy | GAGGTGCAGCTGGTGGAGTCTGGGGGAGGCTTGGTACAGCCCGGGGGGTCCCTGAGAC<br>TGTCCTGTGCAGCCTCTGGATTCACTTTTAGGAACTACGCCATGAGCTGGGTCCGCCA<br>GGCTCCAGGGAAGGGGCTGGAGTGGGTCTCAGATATCAGTAGTGGTGGTGATACCACA<br>TACTACGCAGAGTCCCTGAAGGGCCGGATCACCATCTCCAGAGACAATTCCAAGAACA<br>CGCTGTATCTGCAAATGAACAGCCTGAGAGCCGAGGACGCGGCCATTTATTTCTGTGC<br>GAAACATTTACTATCCCCTATGTACGTTAATACCGATGTGTTTCCGGACTGGTACTTC<br>GAAATCTGGGGCCGTGGCACCCTGGTCACCGTCTCCTCAG | 9 |
| 7 light | TCCTATGAGCTGACACAGCCACCCTCGGTGTCAGTGTCCCCAGGACAGACGGCCAGGA<br>TCACCTGCTCTGGAGATGGATTGCCAAAAAAATATGCTTATTGGTACCAGCAGAAGTC<br>AGGCCAGGCCCCTGTCTTGGTCATCTATGATGACAGTAAGCGACCCTCCGGGATCCCT<br>GAGAGATTCTCTGGCACCAGCTCAGGGACAATGGCCACCTTGATTATCAGTGGGGCCC<br>AGGTGGAGGATGAGGCTGACTACTACTGTTACTCAAGACACAACAGTGCTTATCAAAG<br>GGTGTTCGGCGCAGGGACCCAGCTGACCGTCCTA | 10 |

TABLE 1-continued

NUCLEOTIDE SEQUENCES FOR ANTIBODY VARIABLE REGIONS

| Clone | Variable Sequence Region | SEQ ID NO: |
|---|---|---|
| 131 heavy | CAAGTGCAGCTGGTGCAGTCTGGAACTGAGGTGAAGAAGCCTGGGACCTCAGTGAAGG<br>TCTCCTGCAAGGCTTCTGGTTACATTTTTAGCAACTATGGAATCAGTTGGGTGCGACA<br>GGCCCCTGGACAAGGGCTTGAGTGGATGGGGTGGATCAGCGTTTACAATGGTAACACA<br>AACTATGCACAGAAGTTCCAGGGCAGAGTCACCTTGACCACAGACACATCCACGAACA<br>CTGCCTACATGGAGGTGAGGAGTCTGAGCTCTGACGACACGGCCGTATATTACTGTGC<br>GAGAGAACCCCCGAGTCTTACAGCAGCTGGGCTTCTTGACTACTGGGGCCAGGGAACC<br>CTGGTCACCGTCTCCTCA | 11 |
| 131 light | CAGGCTGTGGTGACTCAGTCTCCACTCTCCCTGCCCGTCACCCTTGGACAGCCGGCCT<br>CCATCTCCTGCAGGTCTAGTCAAAGCCCCGTATACAGTGATGGAAACACCTACTTGAG<br>TTGGTTTCAGCAGAGGCCAGGCCAATCTCCAAGGCGCCTCATCTATGGAGCATCTGCC<br>AGGGCCACTGGTATCCCAGCCAGGTTCAGTGGCAGTGGGTCTGGGACAGACTTCACTC<br>TCACCATCAGCAGCCTGCAGTCTGAAAATTTTGCATTCTATTACTGTCAGCAGTATAA<br>TAATTGGCCTCTCACTTTCGGCGGAGGGACCAAGGTGGAGATCAAG | 12 |
| 75 heavy | GAGGTGCAGCTGGTGGAGTCTGGGGGAGGCCTGGTCAAGCCTGGGGGGTCCCTGAGGC<br>TCTCCTGTGCAGCCTCTGGATTCACCTTCCGTAGTTATAGCATGAACTGGGTCCGCCA<br>GGCTCCAGGGAAGGGGCTGGAGTGGGTCTCATCCATTACTAGTAGCAGTAGTTACATA<br>GACTACGCAGACTCAGTGAAGGGCCGATTCACCATCTCCAGAGACAACGCCAAGAACT<br>CACTGTATCTTCAAATGAACAGCCTGAGAGCCGAGGACACGGCTGTGTATTACTGCGC<br>GAGAGCATATTGTGGTGGTGACTGCTCGGTTGACCACTTCCAGCACTGGGGCCAGGGC<br>ACCCTGGTCACCGTCTCCTCAG | 13 |
| 75 light | CAGTCTGTGCTGACTCAGCCGCCCTCAGTGTCTGGGGCCCCAGGGCAGAGGGTCACCA<br>TCTCCTGCACTGGGAGCAGCTCCAACATCGGGGCAGGTTATGATGTACACTGGTACCA<br>GCACCTTCCAGGAACAGCCCCCAAACTCCTCATCTATGTTAACAGCAATCGGCCCTCA<br>GGGGTCCCTGACCGCTTCTCTGCCTCCAAGTCTGGCACCTCAGCCTCCTGGCCATCA<br>CTGGGCTCCAGGCTGAGGACGAGGCTGATTATTACTGCCAGTCCTATGACAAAGCCT<br>GAGTGGTTTTTATGTCTTCGGAACTGGGACCAAGGTCACCGTCCTAG | 14 |
| 12 heavy | CAGGTTCAGCTGGTGCAGTCTGGAGCTGAGGTTAAGAAGCCTGGGACCTCAGTGAGGG<br>TCTCCTGCAAGACTTCTGGTTATAACTTTATGAACTATGGTATCTACTGGGTGCGGCA<br>GGCCCCTGGACAGGGACTTGAGTGGGTGGGATGGATCAGCGCCTACAATGGTCAAACA<br>GACCGTGCACAGAAGTTCCAGGGCAGAGTCACCATGACCACAGACATATCCACGAACA<br>CAGGTTACATGGACCTGAGGAGTCTCAGATCTGACGACACGGCCGTGTATTTTTGTGC<br>GAGAGGGCCCCCTGTTATAGCAGCAGTGTCCTTAGAATATTGGGGCCGGGGAACCCTG<br>GTCACCGTCTCCTCAG | 15 |
| 12 light | GAGGTTGTGATGACTCAGTCTCCACTCTCCCTGCCCGTCACCCTTGGGCAGCCGGCCT<br>CCATCTCCTGCAAGTCTAGTCAAAGTCTCGTACACAGTAATGGAGACACCTACCTGAA<br>TTGGTTTCAGCAGAGGCCAGGCCAATCTCCAAGGCGCCTAATTTATAAGGTTTCTAAC<br>CGGGACTCTGGGGTCCCAGATAGATTCAGCGGCAGCGGGTCAGGCACTGATTTCACAC<br>TGAAAATCAGTAGGGTGGAGACTGAGGATGTTGGGGTTTATTACTGCATGCAAGCTAC<br>ACACTGGCCAGGCAGTTTTGGCCAGGGGACCAAGCTGGAGATCAAAC | 16 |
| 141 heavy | CAAGTGCAGCTGGTGCAGTCTGGGGCTGAGGTGAAGAAGCCTGGGGCCTCAGTGAAGG<br>TCTCCTGCAAGGCTTCTGGATACACCTTCACCAACTACTATATGCACTGGGTGCGACA<br>GGCCCCTGGACAAGGGCTTGAGTGGATGGGATGGATCAACCCTAACAGAGGTGGCACA<br>AACTATGCACAGAAGTTTCAGGGCAGGGTCACCATGACCCTGGACACGTCCATCAGTA<br>CAGCCTACATAGAGCTGAGCAGGCTGAGATCTGACGACACGGCCGTGTATTACTGTGC<br>GAGAGATCTGACCTTGGGGACGGACTACTGGGGCCAGGGAACCCTGGTCACCGTCTCC<br>TCA | 17 |
| 141 light | CAGGCTGTGGTGACTCAGCCTGCCTCCGTGTTTGGGTTTCCTGGACAGTCGATCACCA<br>TTTCCTGCACTGGAACCAGCAGTGACGTTGGTGGTTATAAATATGTTTCCTGGTACCA<br>ACAGCGCCCAGGCAAAGCCCCCAAAATCATGATTTATGAGGTCAGTAATCGGCCCTCA<br>GGGGTTTCTAATCGCTTCTCTGGCTCCAAGTCTGGCAACACGGCCTCCTGACCATCT<br>CTGGGCTCCAGGCTGAGGACGAGGCTGATTATTACTGCAACTCATATACAAGCAGCAA<br>CTCTTATGTCTTCGGAACTGGGACCAAGGTCACCGTC | 18 |
| 137 heavy | CAGGTTCAGCTGGTGCAGTCTGGAGCTGAGGTGAAGAAGCCTGGGGCCTCACTGAAGG<br>TCTCCTGCAAGGCTTCTGGTTACACTTTTTCCAACTATGGTCTTAGTTGGGTGCGACA<br>GGCCCCTGGACAAGGGCTTGAGTGGATGGGATGGATCAGCGATTACAATGGTAACACA<br>GAGTATGCACAGAAGTTCCAGGGCAGAGTCACCATGACCACAGACAGATCCACGAGCA<br>CTGCCTACATGGAACTAAAGAGCCTGAGATCTGACGACACGGCCGTGTATTACTGTGC<br>GAGAGACCCCCCTGCAGCAGCAGCTGCCACTTATGACTACTGGGGCCAGGGAACCCTG<br>GTCACCGTCTCCTCAG | 19 |
| 137 light | CAGACTGTGATGACTCAGTCTCCACCCTCCCTGTCTGCATCTATAGGAGACAGAGTCA<br>CCATCACTTGCCGGGTGAGTCAGGGCATTGCCAGTTACTTAAATTGGAATCGGCAGAA<br>ACCAGGGAACTTTCCTAAGGTCCTGATGCAGAGTATATCCAATTTGCAATCTGGAGTC<br>CCATCTCGCTTCAGCGGCAGTGGGTCTGGGACAGATTTCACTCGCACCATCAGCAGCC<br>TGCAGCCTGAAGATGTTGCGACTTATTACGGTCGACGGACTTACAATGCCCCTCTTGC<br>ACTTTTGGCCAGGGGACCAACCTGCAGATCAAAC | 20 |

TABLE 1-continued

NUCLEOTIDE SEQUENCES FOR ANTIBODY VARIABLE REGIONS

| Clone | Variable Sequence Region | SEQ ID NO: |
|---|---|---|
| 106 heavy | CAGATCACCTTGAAGGAGTCTGGTCCTACGCTGGTGAAGCCCACACAGACCCTCACGC<br>TGACTTGTACCTTCTCTGGTTTCTCACTCACCACTCGTGGAGTGGGTGTGGCCTGGAT<br>CCGTCAGCCCCCAGGCAAGGCCCTGGAGTGGCTTGCACTCATTTATTGGGATGATGAT<br>AAGCGCTACAGGTCATCTCCAAAGGGCAGACTCACCATCACCAAGGACAACTCCAAAA<br>ACCAGGTGGTCCTTATAATGACCAACATGGACCCTGTGGACACAGCCACATATTACTG<br>TGCCCACGCCATGGATGATTCGGGGAGTTATTATGTCGGATTGTCAAAGGACCCCCAC<br>TTTGACTCCTGGGGCCACGGAACCCTGGTCACCGTCTCCTCAG | 21 |
| 106 light | TCCTATGAGCTGACTCAGCCACCCTCAGTGTCCGTGTCCCCAGGACAGACAGCCAGCA<br>TTACCTGCTCTGGTGATGTATTGTTTAATAAATTTGCTTCCTGGTATCAGCAGAAGCC<br>AGGCCAGTCTCCTGTGCTGGTCATCTATCAGGATAGTAAGCGGCCCTCAGGGATCCCT<br>GAACGATTCTCTGGCTCCAACTCTGGGAACACAGCCACTCTGACCATCAGGGGGACCC<br>AGGCTATGGATGAGGCCGACTATTACTGTCAGGCGCGGGGCAGCACCGCTGCACATGT<br>GATTTTCGGCGGGGGGACCAAGGTGACCGTCCTAG | 22 |
| 139 heavy | CAGGTGCAGCTGGTGCAGTCTGGAGCTGAGGTGAAGAAGCCTGGGGCCTCAGTAAAGG<br>TCTCCTGTAAGGCCTCTGGTTACGTCTTTAGCAATTATGGTATCAGTTGGGTGCGACA<br>GGCCCCTGGACAGGGGCTTGAGTGGATGGGATGGATCAGCGCTTATAATGGCAACACA<br>GAGTTTGCACAGAAGTTCCAGGGCAGAATCACCATGACCACAGACACATCCACGAACA<br>CAGCCTACCTGGAGGTGAGGGCCTGAGATCTGACGACACGGCCGTCTATTATTGTTC<br>ACGACAATCAGGTGTTTCAGGAGTTCCAGAGTTTCAGGACTGGGGCCAGGGAACCCTG<br>GTCACCGTCTCCTCA | 23 |
| 139 light | CAGGCTGTGGTGACTCAGTCTCCGCTCTCCCTGCCCGTCACCCTTGGACAGCCGGCCT<br>CCATCTCCTGCAGGTCTAGTCAAAGCCTCGTGTACAGTAATGGAGACACCTACTTGAG<br>TTGGTTTCAGCAGAGGCCAGGCCAGTCTCCAAGGCGCCTAATCTATAAGGTTTCTAAC<br>CGGGACTCTGGGGTCCCAGACAGATTCAGCGCCAGTGGGTCAGGCACTGATTTCACAC<br>TGAAAATCAGCAGGGTGGAGGCTGAGGATGTTGGGGTTTATTACTGCATGCAGGGTAC<br>ACACTGGCCTCCGCCCACCTTCGGCCAAGGGACACGACTGGAGATTAAA | 24 |
| 97 heavy | GAAGTGCAGCTGGTGGAGTCTGGGGGAACCTTGGTGCAGCCTGGCAGGTCCCTGAGAC<br>TCTCCTGTGCCGCCTCTGGATTCAATTTTGAAGAATATGCCATGCACTGGGTCAGGCA<br>AGTTCCAGGGAAGGGCCTGGAGTGGGTCGCACGAATTAATTGGAATGGCGGTATCATA<br>GGCTATGCGGACTCTGTGAAGGGCCGATTTACGATCTCCAGAGACAACGCCAAGAAGT<br>CCTTGTATCTGCAAATGAACAGTCTGAGAACTGACGATTCGGCCTTGTATTACTGTGG<br>AAAAGATGTGTTTTGGGCAGTGGCTGGTACGGGGGGGCCTATTGACTCCTGGGGCCAG<br>GGAACCCTGGTCACCGTCTCCTCAG | 25 |
| 97 light | GACATCGTGATGACCCAGTCTCCATCCTCCCTGTCTGCATCTATAGGAGACAGAGTCA<br>CCATCTCTTGCCGGGCGAGTCGGGACATTAGTAATTATTTAGCCTGGTATCAGCAGAA<br>ATCAGGGAAAGTCCCTAAACTCCTGATATATGCTGCATCCACTTTGGAATCAGGGGTC<br>CCGTCTCGCTTCAGTGGCAGTGGATCTGGGACAGATTTCACTCTCACCATCAGCAGCC<br>TGCAGCCTGAAGATGTTGCAACTTATTACTGTCAAAACTATAACAGTGCCCAGATGTG<br>CAGTTTTGGCCAGGGACCAAGCTTGGAGATCAAA | 26 |

TABLE 2

PROTEIN SEQUENCES FOR ANTIBODY VARIABLE REGIONS

| Clone | Variable Sequence | SEQ ID NO: |
|---|---|---|
| 90 heavy | EVQLVESGGGLVQPRRSLRLSCAASGFTFDDYTIHWVRQAPGKGLEWVSGITWNSGYIG<br>YADSVKGRFTISRDNARNSLYLQMNSLRAEDTALYYCVRDAYVSGSDYYYYGLDVWGRG<br>TLVTVSS | 27 |
| 90 light | EIVMTSSPATLSVSPGERATLFCRASQSVISNLAWYQQKSGQAPRLLIYGASTRATGIP<br>ARFSGSGSGTEFTLTISSLQSEDFAVYFCQQYNNWPLTFGGGTQVNVQ | 28 |
| 20 heavy | QVQLVESGGGLVQPGRSLRLSCAASGFTFDDYAMHWVRQAPGRGLEWVSGISWNSGIAV<br>YADSVKGRFTISRDNAKKSLYLQINSLRAEDTALYYCVKDNYASGSYSSYYYYGLDLW<br>GQGTLVTVSS | 29 |
| 20 light | EIVMTQSPATLSVSPGERATLSCRASQSIISNLAWYQQKPGQAPRLLIYGVSTRATGIP<br>ARFSGSGSDTEFTLSISSLQSEDFAVYYCQQYNNWPITFGQGTRLEIK | 30 |
| 130 heavy | XVQLVQSGGGLVQPGRSLRLSCRASGFRFDDYAMHWVRQVPGKGLEWVSGISWHSGHRD<br>YADSVKGRFTISRDNAKNSLYLEMNSLRAEDTALYYCVKDSHYFDNSGSYTYGLDVWGQ<br>GTLVTVSS | 31 |
| 130 light | QXVMTQSPATLSVSPGERATLSCRASQSVLSNLAWYQQKPSQAPRLLIYGASARATGIP<br>ARFSGSGSGTDFTLTISSLQSEDFAVYYCQQYNNWPLTFGGGTKVEIK | 32 |

TABLE 2-continued

PROTEIN SEQUENCES FOR ANTIBODY VARIABLE REGIONS

| Clone | Variable Sequence | SEQ ID NO: |
|---|---|---|
| 61 heavy | QVQLVQSGAELKKPGASVKVSCKASGYTFTNHGITWVRQAPGQGLEWMSWISGYNGNTQ YAQKFQGRVTMTTDTSTRTAYMELRSLTSDDTAVYYCARDNGVVVGPPDYWGQGTLVTV SS | 33 |
| 61 light | DIQMTQSPSTLSASVGDRVTISCRASQSISSWLAWYQQKPGKPPKLLIYKASGLQTGVP SRFSGSGSGTEFTLTISSLQPDDFATYYCQYYHSLSAFGQGTKVEIK | 34 |
| 7 heavy | EVQLVESGGGLVQPGGSLRLSCAASGFTFRNYAMSWVRQAPGKGLEWVSDISSGGDTTY YAESLKGRITISRDNSKNTLYLQMNSLRAEDAAIYFCAKHLLSPMYVNTDVFPDWYFEI WGRGTLVTVSS | 35 |
| 7 light | SYELTQPPSVSVSPGQTARITCSGDGLPKKYAYWYQQKSGQAPVLVIYDDSKRPSGIPE RFSGTSSGTMATLIISGAQVEDEADYYCYSRHNSAYQRVFGAGTQLTVL | 36 |
| 131 heavy | QVQLVQSGTEVKKPGTSVKVSCKASGYIFSNYGISWVRQAPGQGLEWMGWISVYNGNTN YAQKFQGRVTLTTDTSTNTAYMEVRSLSSDDTAVYYCAREPPSLTAAGLLDYWGQGTLV TVSS | 37 |
| 131 light | QAVVTQSPLSLPVTLGQPASISCRSSQSPVYSDGNTYLSWFQQRPGQSPRRLIYKISNR DSGVPDRFSGSGSGTDFTLKISRVEAEDVGVYYCMQGTHWPRTFGQGTKVEIK | 38 |
| 75 heavy | EVQLVESGGGLVKPGGSLRLSCAASGFTFRSYSMNWVRQAPGKGLEWVSSITSSSSYID YADSVKGRFTISRDNAKNSLYLQMNSLRAEDTAVYYCARAYCGGDCSVDHFQHWGQGTL VTVSS | 39 |
| 75 light | QSVLTQPPSVSGAPGQRVTISCTGSSSNIGAGYDVHWYQHLPGTAPKLLIYVNSNRPSG VPDRFSASKSGTSASLAITGLQAEDEADYYCQSYDKSLSGFYVFGTGTKVTVL | 40 |
| 12 heavy | QVQLVQSGAEVKKPGTSVRVSCKTSGYNFMNYGIYWVRQAPGQGLEWVGWISAYNGQTD RAQKFQGRVTMTTDISTNTGYMDLRSLRSDDTAVYFCARGPPVIAAVSLEYWGRGTLVT VSS | 41 |
| 12 light | EVVMTQSPLSLPVTLGQPASISCKSSQSLVHSNGDTYLNWFQQRPGQSPRRLIYKVSNR DSGVPDRFSGSGSGTDFTLKISRVETEDVGVYYCMQATHWPGSFGQGTKLEIK | 42 |
| 141 heavy | QVQLVQSGAEVKKPGASVKVSCKASGYTFTNYYMHWVRQAPGQGLEWMGWINPNRGGTN YAQKFQGRVTMTLDTSISTAYIELSRLRSDDTAVYYCARDLTGTDYWGQGTLVTVSSA S | 43 |
| 141 light | QAVVTQPASVFGFPGQSITISCTGTSSDVGGYNYVSWYQQRPGKAPKLMIYEVSNRPSG VSNRFSGSKSGNTASLTISGLQAEDEADYYCNSYTSSNSYVFGTGTKVTVL | 44 |
| 137 heavy | QVQLVQSGAEVKKPGASLKVSCKASGYTFSNYGLSWVRQAPGQGLEWMGWISDYNGNTE YAQKFQGRVTMTTDRSTSTAYMELKSLRSDDTAVYYCARDPPAAAAATYDYWGQGTLVT VSS | 45 |
| 137 light | QTVMTQSPPSLSASIGDRVTITCRVSQGIASYLNWNRQKPGNFPKVLMQSISNLQSGVP SRFSGSGSGTDFTRTISSLQPEDVATYYGRRTYNAPLALLARGPTCRSN | 46 |
| 106 heavy | QITLKESGPTLVKPTQTLTLTCTFSGFSLTTRGVGVAWIRQPPGKALEWLALIYWDDDK RYRSSPKGRLTITKDNSKNQVVLIMTNMDPVDTATYYCAHAMDDSGSYYVGLSKDPHFD SWGHGTLVTVSS | 47 |
| 106 light | SYELTQPPSVSVSPGQTASITCSGDVLFNKFASWYQQKPGQSPVLVIYQDSKRPSGIPE RFSGSNSGNTATLTIRGTQAMDEADYYCQARGSTAAHVIFGGGTKVTVL | 48 |
| 139 heavy | QVQLVQSGAEVKKPGASVKVSCKASGYVFSNYGISWVRQAPGQGLEWMGWISAYNGNTE FAQKFQGRITMTTDTSTNTAYLEVRGLRSDDTAVYYCSRQSGVSGVPEFQDWGQGTLVT VSS | 49 |
| 139 light | QAVVTQSPLSLPVTLGQPASISCRSSQSLVYSNGDTYLSWFQQRPGQSPRRLIYKVSNR DSGVPDRFSASGSGTDFTLKISRVEAEDVGVYYCMQGTHWPPPTFGQGTRLEIK | 50 |
| 97 heavy | EVQLVESGGTLVQPGRSLRLSCAASGFNFEEYAMHWVRQVPGKGLEWVARINWNGGIIG YADSVKGRFTISRDNAKKSLYLQMNSLRTDDSALYYCGKDVFWAVAGTGGPIDSWGQGT LVTVSS | 51 |
| 97 light | DIVMTQSPSSLSASIGDRVTISCRASRDISNYLAWYQQKSGKVPKLLIYAASTLESGVP SRFSGSGSGTDFTLTISSLQPEDVATYYCQNYNSAQMCSFGQGPSLEIK | 52 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 90 | GFTFDDYT (53) | ITWNSGYI (54) | VRDAYVSGSDYYYYGLDV (55) |
| 20 | GFTFDDYA (56) | ISWNSGIA (57) | VKDNYASGSYSSYYYYYGLDL (58) |
| 130 | GFRFDDYA (59) | ISWHSGHR (60) | VKDSHYFDNSGSYTYGLDV (61) |
| 61 | GYTFTNHG (62) | ISGYNGNT (63) | ARDNGVVVGPPDY (64) |
| 7 | GFTFRNYA (65) | ISSGGDTT (66) | AKHLLSPMYVNTDVFPDWYFEI (67) |
| 131 | GYIFSNYG (68) | ISVYNGNT (69) | AREPPSLTAAGLLDY (70) |
| 75 | GFTFRSYS (71) | ITSSSSYI (72) | ARAYCGGDCSVDHFQH (73) |
| 12 | GYNFMNYG (74) | ISAYNGQT (75) | ARGPPVIAAVSLEY (76) |
| 141 | GYTFTNYY (77) | INPNRGGT (78) | ARDLTLGTDY (79) |
| 137 | GYTFSNYG (80) | ISDYNGNT (81) | ARDPPAAAAATYDY (82) |
| 106 | GFSLTTRGVG (83) | IYWDDDK (84) | AHAMDDSGSYYVGLSKDPHFDS (85) |
| 109 | GYVFSNYG (86) | ISAYNGNT (87) | SRQSGVSGVPEFQD (88) |
| 97 | GFNFEEYA (89) | INWNGGII (90) | GKDVFWAVAGTGGPIDS (91) |

TABLE 4

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| 90 | QSVISN (92) | GAS (93) | QQYNNWPLT (94) |
| 20 | QSIISN (95) | GVS (96) | QQYNNWPIT (97) |
| 130 | QSVLSN (98) | GAS (99) | QQYNNWPLT (100) |
| 61 | QSISSW (101) | KAS (102) | QYYHSLSA (103) |
| 7 | (104) | (105) | (106) |
| 131 | QSPVYSDGNTY (107) | GAS (108) | QQYNNWPLT (109) |
| 75 | SSNIGAGYD (110) | VNS (111) | QSYDKSLSGFYV (112) |
| 12 | QSLVHSNGDTY (113) | KVS (114) | MQATHWPGS (115) |
| 141 | SSDVGGYKY (116) | EVS (117) | NSYTSSNSYV (118) |
| 137 | QGIASY (119) | SIS (120) | RRTYNAPLA (121) |
| 106 | VLFNKF (122) | QDS (123) | QARGSTAAHVI (124) |
| 109 | QSLVYSNGDTY (125) | KVS (126) | MQGTHWPPPT (127) |
| 97 | RDISNY (128) | AAS (129) | QNYNSAQMCS (130) |

TABLE 5

Expression, isotype, binding, and neutralization data for generated hRSV mAbs with controls

| hRSV mAb | Average expression level (mg/L) | IgG subclass | Light chain | Neutralization for indicated strain (IC$_{50}$ [ng/mL]) | | | F protein binding for indicated strain (EC$_{50}$ [ng/mL]) | | | |
|---|---|---|---|---|---|---|---|---|---|---|
| | | | | A2 | 18537 B | Long | RSV A2 SC-TM (pre) | RSV A2 (post) | RSV B 18537 DsCav1 (pre) | RSV B 18537 (post) |
| 90 | 26 | 1 | κ | 15 | 45 | 35 | 28 | > | 31 | > |
| 20 | 1.5 | 1 | κ | 34 | 114 | 14 | 33 | > | 45 | > |
| 75 | 30 | 1 | λ | 129 | 62 | 19 | 44 | > | 40 | > |
| 12 | 23 | 1 | κ | 141 | 443 | 16 | 28 | 285 | 27 | > |
| 130 | 6.7 | 2 | κ | 150 | 58 | 12 | 710 | > | 820 | > |
| 61 | 7 | 1 | κ | 276 | 90 | 54 | 27 | > | 26 | > |
| 137 | 14 | 1 | κ | 363 | 185 | 43 | 27 | > | 22 | > |
| 106 | 5.5 | 1 | λ | 451 | 114 | 43 | 46 | > | 33 | > |
| 139 | 5.1 | 1 | κ | 621 | 216 | 70 | 40 | > | 41 | > |
| 141 | 1.9 | 1 | κ | 626 | 53 | 28 | 29 | > | 36 | > |
| 131 | 3.3 | 1 | κ | 1,180 | 39 | 23 | 53 | 370 | 46 | 92 |
| 7 | 11 | 1 | λ | 1,330 | 22 | 62 | 82 | > | 64 | > |
| 97 | 4.7 | 1 | κ | 2,230 | 65 | 106 | 53 | > | 40 | > |
| Control mAbs | | | | | | | | | | |
| D25 | — | 1 | κ | 21 | > | 9 | 95 | > | > | > |
| 101F | — | 1 | κ | 402 | 109 | 92 | 40 | 85 | 54 | 96 |

TABLE 5-continued

Expression, isotype, binding, and neutralization data for generated hRSV mAbs with controls

| hRSV mAb | Average expression level (mg/L) | IgG subclass | Light chain | Neutralization for indicated strain (IC$_{50}$ [ng/mL]) A2 | 18537 B | Long | F protein binding for indicated strain (EC$_{50}$ [ng/mL]) RSV A2 SC-TM (pre) | RSV A2 (post) | RSV B 18537 DsCav1 (pre) | RSV B 18537 (post) |
|---|---|---|---|---|---|---|---|---|---|---|
| motavizumab | — | 1 | κ | 123 | 91 | 9 | 17 | 83 | 22 | 84 |
| palivizumab | — | 1 | κ | 11,000 | 1270 | 212 | 19 | 24 | 46 | 81 |
| AM14 | — | 1 | κ | 14 | 58 | 43 | 106 | > | > | 198 |

EC$_{50}$ values correspond to the concentration at which half-maximum signal was obtained in enzyme-linked immunosorbent assay, based on optical density at 405 nm. Neutralization values were determined using a plaque-reduction assay, where the IC$_{50}$ corresponds to the mAb concentration at which 50% plaque reduction was observed.
> indicates signal was not detected below 1 μg/mL.

TABLE 6

Antibody gene usage for selected neutralizing mAbs

| | Heavy chain | | | | | Light chain | | | |
|---|---|---|---|---|---|---|---|---|---|
| mAh | V$_H$ gene % Identity | J$_H$ gene % Identity | D$_H$ gene | HCDR lengths | Junction | V$_L$ gene % Identity | J$_L$ gene % Identity | LCDR lengths | Junction |
| 12 | IGHV1-18*01 89% | IGHJ4*02 85% | IGHD6-13*01 | 8.8.14 | CARGPPVIAAVSLEYW (SEQ ID NO: 131) | IGKV2-30*02 96% | IGKJ2*04 95% | 11.3.9 | CMQATHWPGSF (SEQ ID NO: 132) |
| 131 | IGHV1-18*01 93% | IGHJ4*02 87% | IGHD6-13*01 | 8.8.15 | CAREPPSLTAAGLLDYW (SEQ ID NO: 133) | IGKV2-30*01 82% | IGKJ4*01 97% | 11.3.9 | CQQYNNWPLTF (SEQ ID NO: 134) |
| 61 | IGHV1-18*01 93% | IGHJ4*02 83% | IGHD2-15*01 | 8.8.13 | CARDNGVVVGPPDYW (SEQ ID NO: 135) | IGKV1-5*03 96% | IGKJ1*01 94% | 6.3.8 | CQYYHSLSAF (SEQ ID NO: 136) |
| 139 | IGHV1-18*01 92% | IGHJ1*01 84% | IGHD3-10*02 | 8.8.14 | CSRQSGVSGVPEFQDW (SEQ ID NO: 137) | IGKV2-30*01 96% | IGKJ5*01 95% | 11.3.10 | CMQGTHWPPPTF (SEQ ID NO: 138) |
| 90 | IGHV3-9*01 97% | IGHJ6*02 89% | IGHD3-10*01 | 8.8.18 | CVRDAYVSGSDYYYYGLDVW (SEQ ID NO: 139) | IGKV3-15*01 96% | IGKJ4*01 83% | 6.3.9 | CQQYNNWPLTF (SEQ ID NO: 140) |
| 20 | IGHV3-9*01 97% | IGHJ6*02 92% | IGHD3-10*01 | 8.8.21 | CVKDNYASGSYSSYYYYYGLDLW (SEQ ID NO: 141) | IGKV3-15*01 96% | IGKJ5*01 100% | 6.3.9 | CQQYNNWPITF (SEQ ID NO: 142) |
| 130 | IGHV3-9*01 92% | IGHJ6*02 77% | IGHD3-22*01 | 8.8.19 | CVKDSHYFDNSGSYTYGLDVW (SEQ ID NO: 143) | IGKV3-15*01 94% | IGKJ4*01 97% | 6.3.9 | CQQYNNWPLTF (SEQ ID NO: 144) |
| 97 | IGHV3-9*01 91% | IGHJ4*02 85% | IGHD6-19*01 | 8.8.17 | CGKDVFWAVAGTGGPIDSW (SEQ ID NO: 145) | IGKV1-27*01 95% | IGKJ2*04 84% | 6.3.10 | CQNYNSAQMCSF (SEQ ID NO: 146) |

MAbs are grouped based on heavy chain V gene analysis. hRSV90, hRSV20, hRSV130, and hRSV97 use similar V$_H$ genes, and hRSV12, hRSV131, hRSV61, and hRSV139 use similar V$_H$ genes. hRSV90 and hRSV20 have nearly identical gene usage, and hRSV20 has an HCDR3 insertion. Analysis was carried out by IMGT/VQUEST[18]. The percent identity for each predicted gene usage based on IMGT/VQUEST predictions is also displayed for V$_H$ and J$_H$ or V$_L$ and J$_L$ genes.

TABLE 7

Binding characteristics for hRSV mAbs to variant F proteins mutated at residues that contact mAb hRSV90

Binding to indicated recombinant RSV F point mutant variant protein for residues contacting the indicated CDR of hRSV90 [EC$_{50}$ (ng/mL)]

| hRSV mAb | HCDR1 | | HCDR2 | | HCDR3 | | | | | | LCDR1/2 | | LCDR3 | |
|---|---|---|---|---|---|---|---|---|---|---|---|---|---|---|
| | K201A | K201R | S169A | S169R | S173A | S173R | D194A | D194R | N175A | N175R | D263A | D263R | T174A | T174R |
| 90 | 21 | 18 | 23 | 19 | 10 | > | 42 | 32 | 28 | 11 | 22 | 18 | 18 | > |
| 20 | 20 | 13 | 15 | 14 | 365 | > | 20 | 19 | 50 | 20 | 16 | 18 | 16 | > |
| 75 | 19 | 15 | 14 | 16 | 16 | 17 | 26 | 22 | 66 | 20 | 15 | 23 | 7 | 12 |
| 12 | 25 | 17 | 24 | 26 | 29 | 47 | 33 | 30 | 24 | > | 17 | > | 23 | 27 |

TABLE 7-continued

Binding characteristics for hRSV mAbs to variant F proteins mutated at residues that contact mAb hRSV90

Binding to indicated recombinant RSV F point mutant variant protein for residues contacting the indicated CDR of hRSV90
[$EC_{50}$ (ng/mL)]

| hRSV mAb | HCDR1 | | HCDR2 | | HCDR3 | | | | | | LCDR1/2 | | LCDR3 | |
|---|---|---|---|---|---|---|---|---|---|---|---|---|---|---|
| | K201A | K201R | S169A | S169R | S173A | S173R | D194A | D194R | N175A | N175R | D263A | D263R | T174A | T174R |
| 130 | 280 | 160 | 195 | 201 | 260 | > | 302 | 344 | 480 | > | 1,074 | 250 | 270 | > |
| 61 | 43 | 47 | 59 | 65 | 62 | 98 | 144 | 105 | 72 | 48 | 49 | > | 41 | > |
| 137 | 31 | 26 | 34 | 77 | 29 | 37 | 99 | > | 22 | > | 29 | > | 40 | > |
| 106 | 55 | 45 | 48 | 50 | 51 | 83 | 134 | 197 | 82 | 116 | 46 | 124 | 48 | 39 |
| 139 | 34 | 31 | 37 | 40 | 43 | 75 | 54 | 78 | 56 | > | 36 | > | 41 | 164 |
| 141 | 32 | 30 | 39 | 196 | 36 | 41 | 140 | > | > | > | 44 | > | 271 | > |
| 131 | 21 | 15 | 18 | 18 | 21 | 18 | 27 | 28 | 68 | 22 | 19 | 23 | 19 | 14 |
| 7 | 92 | 62 | 79 | 95 | 71 | 186 | 748 | 695 | 158 | 255 | 62 | 163 | 86 | 64 |
| 97 | 84 | 65 | 63 | 62 | 46 | 173 | 178 | 286 | 106 | 106 | 42 | 145 | 55 | 37 |
| Control mAbs | | | | | | | | | | | | | | |
| D25 | 630 | 21 | 19 | 21 | 35 | 21 | 107 | 44 | 690 | 22 | 19 | 27 | 21 | 16 |
| AM14 | 28 | 23 | 18 | 26 | 170 | 1 | > | 58 | > | > | 27 | 26 | 28 | 18 | hRSV90 CDR loops interacting with specified RSV F SC-TM amino acid residues in the X-ray structure are indicated above each mutation. Both alanine and arginine mutations were tested at each of the seven positions.

TABLE S1

Data collection and refinement statistics

| | hRSV90 + RSV A2F SC-TM | |
|---|---|---|
| Data collection * | | |
| Beamline | LS-CAT 21-ID-G | Anisotropy correction |
| Number of crystals | 1 | |
| Space group | R 3 2 H | |
| Cell dimensions | | |
| a, b, c (Å) | 148.2, 148.2, 538.2 | |
| α, β, γ (°) | 90, 90, 120 | |
| Resolution (Å) | 49.23 – 3.14 | a = 3.6, b = 3.6, |
| | (3.26 – 3.14) | c = 3.1 |
| $R_{merge}$ | 0.385 (4.715) | 0.266 (0.768) |
| I/σI | 5.2 (0.5) | 6.7 (2.2) |
| Completeness (%) | 99.9 (99.8) | 75.2 (4.1) |
| Redundancy | 5.9 (5.9) | 4.4 (0.2) |
| Refinement | | |
| Resolution (Å) | | 48.31 – 3.14 |
| No. unique reflections | | 30527 (272) |
| $R_{work}/R_{free}$ | | 0.2212 (0.2603) |
| No. atoms | | |
| Protein | | 7077 |
| B-factors | | |
| Protein | | 71.68 |
| R.m.s. deviations | | |
| Bond lengths (Å) | | 0.012 |
| Bond angles (°) | | 1.41 |
| Ramachandran statistics | | |
| Favored regions (%) | | 95 |
| Allowed regions (%) | | 4.8 |
| Outliers (%) | | 0.22 |

Values in parentheses are for the highest resolution data shell.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. REFERENCES

The following references, to the extent that they provide exemplary procedural or other details supplementary to those set forth herein, are specifically incorporated herein by reference.

Adams et al. (2010) PHENIX: a comprehensive Python-based system for macromolecular structure solution. *Acta Cryst* 66(Pt 2):213-21.

"Antibodies: A Laboratory Manual," Cold Spring Harbor Press, Cold Spring Harbor, N.Y., 1988.

Abbondanzo et al., *Am. J. Pediatr. Hematol. Oncol.*, 12(4), 480-489, 1990.

Allred et al., *Arch. Surg.*, 125(1), 107-113, 1990.

Anderson et al. (1985) Antigenic characterization of respiratory syncytial virus strains with monoclonal antibodies. *J Infect Dis* 151(4):626-633.

Atherton et al., *Biol. of Reproduction*, 32, 155-171, 1985.

Brown et al., *J. Immunol. Meth.*, 12; 130(1):111-121, 1990.

Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.

Capaldi et al., *Biochem. Biophys. Res. Comm.*, 74(2):425-433, 1977.

Corti et al., Cross-neutralization of four paramyxoviruses by a human monoclonal antibody. *Nature* 501, 439-43 (2013).

Davidson, E. & Doranz, B. J., *Immunology* 143, 13-20, 2014.

De Jager et al., *Semin. Nucl. Med.* 23(2), 165-179, 1993.

Dholakia et al., *J. Biol. Chem.*, 264, 20638-20642, 1989.

Doolittle and Ben-Zeev, *Methods Mol. Biol.*, 109:215-237, 1999.
Emsley & Cowtan (2004) Coot: model-building tools for molecular graphics. *Acta Cryst* 60(Pt 12 Pt 1):2126-32.
Gefter et al., *Somatic Cell Genet.*, 3:231-236, 1977.
Gilman et al. (2015) Characterization of a prefusion-specific antibody that recognizes a quaternary, cleavage-dependent epitope on the RSV fusion glycoprotein. *PLoS Pathog* 11(7):e1005035.
Group TIm-RS (1998) Palivizumab, a humanized respiratory syncytial virus monoclonal antibody, reduces hospitalization from respiratory syncytial virus infection in high-risk infants. *Pediatrics* 102:531-537.
Gulbis and Galand, *Hum. Pathol.* 24(12), 1271-1285, 1993.
Hall C B, et al. (2009) The burden of respiratory synctial virus in young children. *N Engl J Med* 360:588-598.
Kabsch W (2010) *Xds*. *Acta Cryst* 66(2):125-132.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Krarup et al. (2015) A highly stable prefusion RSV F vaccine derived from structural analysis of the fusion mechanism. *Nat Commun* 6:8143.
Kyte and Doolittle, *J. Mol. Biol.*, 157(1):105-132, 1982.
Lopez et al., Antigenic structure of human respiratory syncytial virus fusion glycoprotein. *J. Virol.* 72, 6922-6928 (1998).
McLellan et al., Structure of respiratory syncytial virus fusion glycoprotein in the postfusion conformation reveals preservation of neutralizing epitopes. *J. Virol.* 85, 7788-7796 (2011).
McLellan et al. (2013a) Structure of RSV fusion glycoprotein trimer bound to a prefusion-specific neutralizing antibody. *Science* 340:1113-1117.
McLellan et al. (2013b) Structure-based design of a fusion glycoprotein vaccine for respiratory syncytial virus. *Science* 342(6158):592-598.
McLellan, J. S. (2015) Neutralizing epitopes on the respiratory syncytial virus fusion glycoprotein. *Curr Opin Virol* 11:70-75.
Mousa et al., Structural basis for non-neutralizing antibody competition at antigenic site II of the respiratory syncytial virus fusion protein. *PNAS* (2016).
Nakamura et al., In: *Enzyme Immunoassays: Heterogeneous and Homogeneous Systems*, Chapter 27, 1987.
Ngwuta et al., Prefusion F— specific antibodies determine the magnitude of RSV neutralizing activity in human sera. *Sci. Transl. Med.* 7, 309ra162 (2015).
O'Shannessy et al., *J. Immun. Meth.*, 99, 153-161, 1987.
Persic et al., *Gene* 187:1, 1997
Potter and Haley, *Meth. Enzymol.*, 91, 613-633, 1983.
*Remington's Pharmaceutical Sciences*, 15th Ed., 3:624-652, 1990.
Smith et al., Viral entry mechanisms: the increasing diversity of paramyxovirus entry. *FEBS J.* 276, 7217-7227 (2009).
Smith & Crowe (2015) Use of human hybridoma technology to isolate human monoclonal antibodies. *Microbiol Spectr* 3:1-12.
Strong et al., Toward the structural genomics of complexes: crystal structure of a PE/PPE protein complex from *Mycobacterium tuberculosis*. *PNAS* 103, 8060-8065 (2006).
Tang et al., *J. Biol. Chem.*, 271:28324-28330, 1996.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
Wawrzynczak & Thorpe, In: *Immunoconjugates, Antibody Conuugates In Radioimaging And Therapy Of Cancer*, Vogel (Ed.), NY, Oxford University Press, 28, 1987.
Wu et al. (2007a) Characterization of the epitope for anti-human respiratory syncytial virus F protein monoclonal antibody 101F using synthetic peptides and genetic approaches. *J Gen Virol* 88(10):2719-2723.
Wu et al. (2007b) Development of motavizumab, an ultrapotent antibody for the prevention of respiratory syncytial virus infection in the upper and lower respiratory tract. *J Mol Biol* 368(3):652-665.
Yu et al., (2008) An optimized electrofusion-based protocol for generating virus-specific human monoclonal antibodies. *J Immunol Methods* 336(2):142-151.

What is claimed is:

1. A method of treating a subject infected with human respiratory syncytial virus, or reducing the likelihood of infection of a subject at risk of contracting human respiratory syncytial virus, comprising delivering to said subject an antibody or antibody fragment having clone-paired heavy and light chain CDR sequences from Tables 3 and 4, respectively.

2. The method of claim 1, the antibody or antibody fragment is encoded by clone-paired light and heavy chain variable sequences as set forth in Table 1.

3. The method of claim 1, the antibody or antibody fragment is encoded by clone-paired light and heavy chain variable sequences having 95% identify to clone-paired sequences from Table 1.

4. The method of claim 1, wherein said antibody or antibody fragment is encoded by light and heavy chain variable sequences having 70%, 80%, or 90% identity to clone-paired sequences from Table 1.

5. The method of claim 1, wherein said antibody or antibody fragment comprises light and heavy chain variable sequences according to clone-paired sequences from Table 2.

6. The method of claim 1, wherein said antibody or antibody fragment comprises light and heavy chain variable sequences having 70%, 80% or 90% identity to clone-paired sequences from Table 2.

7. The method of claim 1, encoded by light and heavy chain variable sequences having 95% identity to clone-paired sequences from Table 2.

8. The method of claim 1, wherein the antibody fragment is a recombinant scFv (single chain fragment variable) antibody, Fab fragment, F(ab')$_2$ fragment, or Fv fragment, a chimeric antibody and/or is an IgG.

9. The method of claim 1, wherein said antibody or antibody fragment recognizes an epitope on pre-fusion RSV F protein in antigenic site VIII, and optionally is specific for an epitope on pre-fusion RSV F protein in antigenic site VIII.

10. The method of claim 9, wherein said antibody or antibody fragment neutralizes RSV A and B subgroups, and/or binds to metapneumovirus fusion protein.

11. The method of claim 1, wherein said antibody or antibody fragment is administered prior to infection.

12. The method of claim 1, wherein said antibody or antibody fragment is administered after infection.

13. The method of claim 1, wherein delivering comprises antibody or antibody fragment administration, or genetic delivery with an RNA or DNA sequence or vector encoding the antibody or antibody fragment.

* * * * *

SEQUENCE LISTING

```
<160> NUMBER OF SEQ ID NOS: 148

<210> SEQ ID NO 1
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 1
gaagtgcagc tggtggagtc tgggggaggc ttggtacagc ctcgcaggtc cctgagactc      60
tcctgtgcag cctctggatt caccttttgat gattatacca tacactgggt ccgccaagct     120
```

| ccagggaagg gcctggagtg ggtctcaggt attacttgga atagtggtta cattggctat | 180 |
| gcggactctg tgaagggccg attcaccatc tccagagaca acgccaggaa ctccctgtat | 240 |
| ctgcaaatga acagtctgag agctgaggac acggccttgt attactgtgt aagagatgcc | 300 |
| tatgtttcgg ggagtgatta ctactactac ggtttggacg tctggggccg agggaccctg | 360 |
| gtcaccgtct cctca | 375 |

<210> SEQ ID NO 2
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 2

| gaaatagtga tgacgtcgtc tccagccacc ctgtctgtgt ctccagggga aagagccacc | 60 |
| ctcttttgca gggccagtca gagtgtgatc agcaacttag cctggtacca gcagaaatct | 120 |
| ggccaggctc ccaggctcct catctatggt gcatccacca gggccactgg tatcccagcc | 180 |
| aggttcagtg gcagtgggtc tgggacagag ttcactctca ccatcagcag cctacagtct | 240 |
| gaagattttg cagtttattt ttgtcagcag tataataact ggcctctcac tttcggcgga | 300 |
| gggacccagg tgaacgtcca aa | 322 |

<210> SEQ ID NO 3
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 3

| caagtgcagc tggtggagtc tggggggaggc ttggtacagc ctggcaggtc cctgagactc | 60 |
| tcctgtgcag cctctggatt cacctttgat gattatgcca tgcactgggt ccggcaagct | 120 |
| ccagggaggg gcctggagtg ggtctcaggt attagttgga atagtggtat cgcagtctat | 180 |
| gcggactctg tgaagggccg attcaccatc tccagagaca acgccaagaa atccctgtat | 240 |
| ctgcaaatca acagtctgag agctgaggac acggccttgt attactgtgt aaaagataac | 300 |
| tatgcttcgg ggagttattc ttcttactac tactactacg gtctggacct ctggggccaa | 360 |
| gggaccctgg tcaccgtctc ctca | 384 |

<210> SEQ ID NO 4
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 4

| gaaattgtga tgactcagtc tccagccacc ctgtctgtgt ctccagggga aagagccacc | 60 |
| ctctcctgca gggccagtca gagtattatc agcaacttag cctggtacca gcaaaaacct | 120 |
| ggccaggctc ccaggctcct catttatggt gtatccacca gggccactgg tatcccagcc | 180 |
| aggttcagtg gcagtgggtc tgacacagag ttcactctct ccatcagcag cctgcagtct | 240 |
| gaagattttg cagtttatta ctgtcagcag tataataact ggccgatcac cttcggccaa | 300 |
| gggacacgac tggagattaa ac | 322 |

<210> SEQ ID NO 5
<211> LENGTH: 378
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t

<400> SEQUENCE: 5

```
nnngtgcagc tggtgcagtc tgggggaggc tggtacagc  ctggcaggtc cctgagactc      60
tcctgtagag cctctggatt tagatttgat gattacgcca tgcactgggt ccggcaagtt     120
ccagggaagg gcctggagtg gtctcaggt  atcagttggc acagtggtca tagagactat     180
gcggactctg tgaagggccg attcaccatc tccagagaca cgccaagaa  ttccctgtat     240
ctagaaatga acagtttgag agctgaggac acggccttgt attattgtgt aaaagacagt     300
cactattttg ataatagtgg ttcttatacc tatggtttgg atgtctgggg ccaagggacc     360
ctggtcaccg tctcctca                                                   378
```

<210> SEQ ID NO 6
<211> LENGTH: 321
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t

<400> SEQUENCE: 6

```
cagnttgtga tgactcagtc tccagccaca ttgtctgtgt ctccagggga aagagccacc      60
ctctcctgca gggccagtca gagtgttctc agcaacttag cctggtacca gcagaaacct     120
agccaggctc ccaggctcct catctatgga gcatctgcca gggccactgg tatcccagcc     180
aggttcagtg gcagtgggtc tgggacagac ttcactctca ccatcagcag cctgcagtct     240
gaagattttg cagtctatta ctgtcagcag tataataatt ggcctctcac tttcggcgga     300
gggaccaagg tggagatcaa g                                               321
```

<210> SEQ ID NO 7
<211> LENGTH: 361
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagc tggtgcagtc tggagctgag ctgaagaagc ctggggcctc agtgaaggtc      60
tcgtgcaagg cttccggtta cacctttacc aatcatggta tcacctgggt gcgacaggcc     120
cctggacaag gcttgagtg  gatgtcatgg atcagcggtt acaatggtaa cacacagtat     180
gcacagaagt tccagggcag agtcaccatg accacagaca catccacgag gacggcctac     240
atggagttga ggagcctgac atctgacgac acggccgtct attattgtgc gagagacaat     300
ggagtcgtag tgggacctcc cgactactgg ggccaggaa  ccctggtcac cgtctcctca     360
g                                                                     361
```

<210> SEQ ID NO 8

<211> LENGTH: 319
<212> TYPE: DNA
<213> ORGANISM: Artificial sequence
<220> FEATURE:
<223> OTHER INFORMATION: Synthetic oligonucleotide

<400> SEQUENCE: 8

```
gacatccaga tgacccagtc tccttccacc ctgtctgcat ccgtaggaga cagagtcacc    60
atatcttgcc gggccagtca gagtattagt agctggttgg cctggtatca gcagaaacca   120
gggaaacccc ctaaactcct gatctataag gcgtccggtt acaaactggg gtcccatca    180
aggttcagcg gcagtggatc tgggacagaa ttcactctca ccatcagcag cctgcagcct   240
gatgattttg caacttatta ctgccaatat tatcatagtc tttcggcttt cggccaaggg   300
accaaggtgg aaatcaaac                                                 319
```

<210> SEQ ID NO 9
<211> LENGTH: 388
<212> TYPE: DNA
<213> ORGANISM: Artificial sequence
<220> FEATURE:
<223> OTHER INFORMATION: Synthetic oligonucleotide

<400> SEQUENCE: 9

```
gaggtgcagc tggtggagtc tgggggaggc ttggtacagc ccgggggtc cctgagactg     60
tcctgtgcag cctctggatt cactttagg aactacgcca tgagctgggt ccgccaggct   120
ccagggaagg gctggagtg gtctcagat atcagtagtg gtggtgatac cacatactac    180
gcagagtccc tgaagggccg gatcaccatc tccagagaca attccaagaa cacgctgtat   240
ctgcaaatga acagcctgag agccgaggac gcggccattt atttctgtgc gaaacattta   300
ctatcccta tgtacgttaa taccgatgtg tttccggact ggtacttcga atctggggc    360
cgtggcaccc tggtcaccgt ctcctcag                                       388
```

<210> SEQ ID NO 10

<400> SEQUENCE: 10

000

<210> SEQ ID NO 11
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 11

```
caagtgcagc tggtgcagtc tggaactgag gtgaagaagc ctgggacctc agtgaaggtc     60
tcctgcaagg cttctggtta cattttagc aactatggaa tcagttgggt gcgacaggcc   120
cctggacaag gcttgagtg gatggggtgg atcagcgttt acaatggtaa cacaaactat   180
gcacagaagt tccagggcag agtcaccttg accacagaca catccacgaa cactgcctac   240
atggaggtga ggagtctgag ctctgacgac acggccgtat attactgtgc gagagaaccc   300
ccgagtctta cagcagctgg gcttcttgac tactggggcc agggaaccct ggtcaccgtc   360
tcctca                                                               366
```

<210> SEQ ID NO 12
<211> LENGTH: 336
<212> TYPE: DNA

<213> ORGANISM: Artificial sequence
<220> FEATURE:
<223> OTHER INFORMATION: Synthetic oligonucleotide

<400> SEQUENCE: 12

```
caggctgtgg tgactcagtc tccactctcc ctgcccgtca cccttggaca gccggcctcc    60
atctcctgca ggtctagtca aagccccgta tacagtgatg gaaacaccta cttgagttgg   120
tttcagcaga ggccaggcca atctccaagg cgcctcatct atggagcatc tgccagggcc   180
actggtatcc cagccaggtt cagtggcagt gggtctggga cagacttcac tctcaccatc   240
agcagcctgc agtctgaaaa ttttgcattc tattactgtc agcagtataa taattggcct   300
ctcactttcg gcggagggac caaggtggag atcaag                             336
```

<210> SEQ ID NO 13
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 13

```
gaggtgcagc tggtggagtc tgggggaggc ctggtcaagc ctgggggtgtc cctgaggctc    60
tcctgtgcag cctctggatt caccttccgt agttatagca tgaactgggt ccgccaggct   120
ccagggaagg ggctggagtg ggtctcatcc attactagta gcagtagtta catagactac   180
gcagactcag tgaagggccg attcaccatc tccagagaca cgccaagaa ctcactgtat    240
cttcaaatga acagcctgag agccgaggac acggctgtgt attactgcgc gagagcatat   300
tgtggtggtg actgctcggt tgaccacttc cagcactggg gccagggcac cctggtcacc   360
gtctcctcag                                                          370
```

<210> SEQ ID NO 14
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 14

```
cagtctgtgc tgactcagcc gccctcagtg tctggggccc cagggcagag ggtcaccatc    60
tcctgcactg ggagcagctc caacatcggg gcaggttatg atgtacactg gtaccagcac   120
cttccaggaa cagcccccaa actcctcatc tatgttaaca gcaatcggcc ctcaggggtc   180
cctgaccgct tctctgcctc caagtctggc acctcagcct ccctggccat cactgggctc   240
caggctgagg acgaggctga ttattactgc cagtcctatg acaaaagcct gagtggtttt   300
tatgtcttcg gaactgggac caaggtcacc gtcctag                            337
```

<210> SEQ ID NO 15
<211> LENGTH: 364
<212> TYPE: DNA
<213> ORGANISM: Artificial sequence
<220> FEATURE:
<223> OTHER INFORMATION: Synthetic oligonucleotide

<400> SEQUENCE: 15

```
caggttcagc tggtgcagtc tggagctgag gttaagaagc ctgggacctc agtgagggtc    60
tcctgcaaga cttctggtta taactttatg aactatggta tctactgggt gcggcaggcc   120
cctggacagg gacttgagtg ggtgggatgg atcagcgcct acaatggtca aacagaccgt   180
```

```
gcacagaagt tccagggcag agtcaccatg accacagaca tatccacgaa cacaggttac    240
atggacctga ggagtctcag atctgacgac acggccgtgt attttgtgc gagagggccc    300 cctgttatag cagcagtgtc cttagaatat tggggccggg aaccctggt caccgtctcc    360 tcag                                                                  364

<210> SEQ ID NO 16
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 16
gaggttgtga tgactcagtc tccactctcc ctgcccgtca cccttgggca gccggcctcc     60
atctcctgca gtctagtca aagtctcgta cacagtaatg gagacaccta cctgaattgg    120
tttcagcaga ggccaggcca atctccaagg cgcctaattt ataaggtttc taaccgggac    180
tctggggtcc cagatagatt cagcggcagc gggtcaggca ctgatttcac actgaaaatc    240
agtagggtgg agactgagga tgttggggtt tattactgca tgcaagctac acactggcca    300
ggcagttttg gccaggggac caagctggag atcaaac                             337

<210> SEQ ID NO 17
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 17
caagtgcagc tggtgcagtc tggggctgag gtgaagaagc ctggggcctc agtgaaggtc     60
tcctgcaagg cttctggata caccttcacc aactactata tgcactgggt gcgacaggcc    120
cctggacaag gcttgagtg gatgggatgg atcaaccta acagaggtgg cacaaactat    180
gcacagaagt ttcagggcag ggtcaccatg accctggaca cgtccatcag tacagcctac    240
atagagctga gcaggctgag atctgacgac acggccgtgt attactgtgc gagagatctg    300
accttgggga cggactactg ggccaggga accctggtca ccgtctcctc a              351

<210> SEQ ID NO 18
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 18
caggctgtgg tgactcagcc tgcctccgtg tttgggtttc ctggacagtc gatcaccatt     60
tcctgcactg gaaccagcag tgacgttggt ggttataaat atgtttcctg gtaccaacag    120
cgcccaggca aagcccccaa atcatgatt tatgaggtca gtaatcggcc ctcagggtt     180 tctaatcgct tctctggctc caagtctggc aacacggcct ccctgaccat ctctgggctc    240
caggctgagg acgaggctga ttattactgc aactcatata caagcagcaa ctcttatgtc    300
ttcggaactg ggaccaaggt caccgtc                                         327

<210> SEQ ID NO 19
<211> LENGTH: 364
<212> TYPE: DNA
```

<213> ORGANISM: Artificial sequence
<220> FEATURE:
<223> OTHER INFORMATION: Synthetic oligonucleotide

<400> SEQUENCE: 19

```
caggttcagc tggtgcagtc tggagctgag gtgaagaagc ctggggcctc actgaaggtc    60
tcctgcaagg cttctggtta cacttttttcc aactatggtc ttagttgggt gcgacaggcc   120
cctggacaag gcttgagtg gatgggatgg atcagcgatt acaatggtaa cacagagtat   180
gcacagaagt tccagggcag agtcaccatg accacagaca gatccacgag cactgcctac   240
atggaactaa agagcctgag atctgacgac acggccgtgt attactgtgc gagagacccc   300
cctgcagcag cagctgccac ttatgactac tggggccagg gaaccctggt caccgtctcc   360
tcag                                                                 364
```

<210> SEQ ID NO 20
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 20

```
cagactgtga tgactcagtc tccaccctcc ctgtctgcat ctataggaga cagagtcacc    60
atcacttgcc gggtgagtca gggcattgcc agttacttaa attggaatcg cagaaaacca   120
gggaactttc ctaaggtcct gatgcagagt atatccaatt tgcaatctgg agtcccatct   180
cgcttcagcg gcagtgggtc tgggacagat ttcactcgca ccatcagcag cctgcagcct   240
gaagatgttg cgacttatta cggtcgacgg acttacaatg cccctcttgc acttttggcc   300
aggggaccaa cctgcagatc aaac                                           324
```

<210> SEQ ID NO 21
<211> LENGTH: 391
<212> TYPE: DNA
<213> ORGANISM: Artificial sequence
<220> FEATURE:
<223> OTHER INFORMATION: Synthetic oligonucleotide

<400> SEQUENCE: 21

```
cagatcaccct tgaaggagtc tggtcctacg ctggtgaagc ccacacagac cctcacgctg    60
acttgtacct tctctggttt ctcactcacc actcgtggag tgggtgtggc ctggatccgt   120
cagcccccag gcaaggccct ggagtggctt gcactcattt attgggatga tgataagcgc   180
tacaggtcat ctccaaaggg cagactcacc atcaccaagg acaactccaa aaaccaggtg   240
gtccttataa tgaccaacat ggaccctgtg gacacagcca catattactg tgcccacgcc   300
atggatgatt cggggagtta ttatgtcgga ttgtcaaagg accccactt tgactcctgg   360
ggccacggaa ccctggtcac cgtctcctca g                                   391
```

<210> SEQ ID NO 22
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 22

```
tcctatgagc tgactcagcc accctcagtg tccgtgtccc caggacagac agccagcatt    60
acctgctctg gtgatgtatt gtttaataaa tttgcttcct ggtatcagca gaagccaggc   120
```

```
cagtctcctg tgctggtcat ctatcaggat agtaagcggc cctcagggat ccctgaacga    180
ttctctggct ccaactctgg gaacacagcc actctgacca tcaggggac ccaggctatg    240 gatgaggccg actattactg tcaggcgcgg ggcagcaccg ctgcacatgt gattttcggc    300 gggggggacca aggtgaccgt cctag                                          325

<210> SEQ ID NO 23
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 23
caggtgcagc tggtgcagtc tggagctgag gtgaagaagc tggggcctc agtaaaggtc      60 tcctgtaagg cctctggtta cgtctttagc aattatggta tcagttgggt gcgacaggcc   120
cctggacagg ggcttgagtg gatgggatgg atcagcgctt ataatggcaa cacagagttt   180
gcacagaagt tccagggcag aatcaccatg accacagaca catccacgaa cacagcctac   240
ctggaggtga ggggcctgag atctgacgac acggccgtct attattgttc acgacaatca   300
ggtgtttcag gagttccaga gtttcaggac tggggccagg gaaccctggt caccgtctcc   360
tca                                                                   363

<210> SEQ ID NO 24
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 24
caggctgtgg tgactcagtc tccgctctcc ctgcccgtca cccttggaca gccggcctcc      60
atctcctgca ggtctagtca aagcctcgtg tacagtaatg agacaccta cttgagttgg   120 tttcagcaga ggccaggcca gtctccaagg cgcctaatct ataaggtttc taaccgggac   180
tctggggtcc cagacagatt cagcgccagt gggtcaggca ctgatttcac actgaaaatc   240
agcagggtgg aggctgagga tgttggggtt tattactgca tgcagggtac acactggcct   300
ccgcccacct tcggccaagg gacacgactg gagattaaa                            339

<210> SEQ ID NO 25
<211> LENGTH: 373
<212> TYPE: DNA
<213> ORGANISM: Artificial sequence
<220> FEATURE:
<223> OTHER INFORMATION: Synthetic oligonucleotide

<400> SEQUENCE: 25
gaagtgcagc tggtggagtc tggggggaacc ttggtgcagc ctggcaggtc cctgagactc     60
tcctgtgccg cctctggatt caattttgaa gaatatgcca tgcactgggt caggcaagtt   120
ccagggaagg gcctggagtg ggtcgcacga attaattgga atggcggtat cataggctat   180
gcggactctg tgaagggccg atttacgatc tccagagaca cgccaagaa gtccttgtat   240 ctgcaaatga acagtctgag aactgacgat tcggccttgt attactgtgg aaaagatgtg   300
ttttgggcag tggctggtac gggggggcct attgactcct ggggccaggg aaccctggtc   360
accgtctcct cag                                                        373
```

<210> SEQ ID NO 26
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 26

```
gacatcgtga tgacccagtc tccatcctcc ctgtctgcat ctataggaga cagagtcacc      60
atctcttgcc gggcgagtcg ggacattagt aattatttag cctggtatca gcagaaatca     120
gggaaagtcc ctaaactcct gatatatgct gcatccactt tggaatcagg ggtcccgtct     180
cgcttcagtg gcagtggatc tgggacagat ttcactctca ccatcagcag cctgcagcct     240
gaagatgttg caacttatta ctgtcaaaac tataacagtg cccagatgtg cagttttggc     300
cagggaccaa gcttggagat caaa                                            324
```

<210> SEQ ID NO 27
<211> LENGTH: 125
<212> TYPE: PRT
<213> ORGANISM: Artificial sequence
<220> FEATURE:
<223> OTHER INFORMATION: Synthetic amino acid

<400> SEQUENCE: 27

```
Glu Val Gln Leu Val Glu Ser Gly Gly Gly Leu Val Gln Pro Arg Arg
1               5                   10                  15

Ser Leu Arg Leu Ser Cys Ala Ala Ser Gly Phe Thr Phe Asp Asp Tyr
            20                  25                  30

Thr Ile His Trp Val Arg Gln Ala Pro Gly Lys Gly Leu Glu Trp Val
        35                  40                  45

Ser Gly Ile Thr Trp Asn Ser Gly Tyr Ile Gly Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Ala Tyr Val Ser Gly Ser Asp Tyr Tyr Tyr Tyr Gly Leu
            100                 105                 110

Asp Val Trp Gly Arg Gly Thr Leu Val Thr Val Ser Ser
        115                 120                 125
```

<210> SEQ ID NO 28
<211> LENGTH: 107
<212> TYPE: PRT
<213> ORGANISM: Artificial sequence
<220> FEATURE:
<223> OTHER INFORMATION: Synthetic amino acid

<400> SEQUENCE: 28

```
Glu Ile Val Met Thr Ser Ser Pro Ala Thr Leu Ser Val Ser Pro Gly
1               5                   10                  15

Glu Arg Ala Thr Leu Phe Cys Arg Ala Ser Gln Ser Val Ile Ser Asn
            20                  25                  30

Leu Ala Trp Tyr Gln Gln Lys Ser Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
```

```
                65                  70                  75                  80
Glu Asp Phe Ala Val Tyr Phe Cys Gln Gln Tyr Asn Asn Trp Pro Leu
                    85                  90                  95

Thr Phe Gly Gly Gly Thr Gln Val Asn Val Gln
                100                 105

<210> SEQ ID NO 29
<211> LENGTH: 128
<212> TYPE: PRT
<213> ORGANISM: Artificial sequence
<220> FEATURE:
<223> OTHER INFORMATION: Synthetic amino acid

<400> SEQUENCE: 29

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Arg Gly Leu Glu Trp Val
            35                  40                  45

Ser Gly Ile Ser Trp Asn Ser Gly Ile Ala Val Tyr Ala Asp Ser Val
        50                  55                  60

Lys Gly Arg Phe Thr Ile Ser Arg Asp Asn Ala Lys Lys Ser Leu Tyr
65                  70                  75                  80

Leu Gln Ile Asn Ser Leu Arg Ala Glu Asp Thr Ala Leu Tyr Tyr Cys
                85                  90                  95

Val Lys Asp Asn Tyr Ala Ser Gly Ser Tyr Ser Ser Tyr Tyr Tyr Tyr
                100                 105                 110

Tyr Gly Leu Asp Leu Trp Gly Gln Gly Thr Leu Val Thr Val Ser Ser
            115                 120                 125

<210> SEQ ID NO 30
<211> LENGTH: 107
<212> TYPE: PRT
<213> ORGANISM: Artificial sequence
<220> FEATURE:
<223> OTHER INFORMATION: Synthetic amino acid

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ile Ser Asn
                20                  25                  30

Leu Ala Trp Tyr Gln Gln Lys Pro Gly Gln Ala Pro Arg Leu Leu Ile
            35                  40                  45

Tyr Gly Val Ser Thr Arg Ala Thr Gly Ile Pro Ala Arg Phe Ser Gly
        50                  55                  60

Ser Gly Ser Asp Thr Glu Phe Thr Leu Ser Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys
                100                 105

<210> SEQ ID NO 31
<211> LENGTH: 126
<212> TYPE: PRT
<213> ORGANISM: Artificial sequence
<220> FEATURE:
```

<223> OTHER INFORMATION: Synthetic amino acid
<220> FEATURE:
<221> NAME/KEY: misc_feature
<222> LOCATION: (1)..(1)
<223> OTHER INFORMATION: Xaa can be any naturally occurring amino acid

<400> SEQUENCE: 31

Xaa Val Gln Leu Val Gln Ser Gly Gly Gly Leu Val Gln Pro Gly Arg
1               5                   10                  15

Ser Leu Arg Leu Ser Cys Arg Ala Ser Gly Phe Arg Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp His Ser Gly His Arg Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Ala Glu Asp Thr Ala Leu Tyr Tyr Cys
                85                  90                  95

Val Lys Asp Ser His Tyr Phe Asp Asn Ser Gly Ser Tyr Thr Tyr Gly
            100                 105                 110

Leu Asp Val Trp Gly Gln Gly Thr Leu Val Thr Val Ser Ser
        115                 120                 125

<210> SEQ ID NO 32
<211> LENGTH: 107
<212> TYPE: PRT
<213> ORGANISM: Artificial sequence
<220> FEATURE:
<223> OTHER INFORMATION: Synthetic amino acid
<220> FEATURE:
<221> NAME/KEY: misc_feature
<222> LOCATION: (2)..(2)
<223> OTHER INFORMATION: Xaa can be any naturally occurring amino acid

<400> SEQUENCE: 32

Gln Xaa Val Met Thr Gln Ser Pro Ala Thr Leu Ser Val Ser Pro Gly
1               5                   10                  15

Glu Arg Ala Thr Leu Ser Cys Arg Ala Ser Gln Ser Val Leu Ser Asn
            20                  25                  30

Leu Ala Trp Tyr Gln Gln Lys Pro Ser Gln Ala Pro Arg Leu Leu Ile
        35                  40                  45

Tyr Gly Ala Ser Ala Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 33
<211> LENGTH: 120
<212> TYPE: PRT
<213> ORGANISM: Artificial sequence
<220> FEATURE:
<223> OTHER INFORMATION: Synthetic amino acid

<400> SEQUENCE: 33

Gln Val Gln Leu Val Gln Ser Gly Ala Glu Leu Lys Lys Pro Gly Ala
1               5                   10                  15

```
Ser Val Lys Val Ser Cys Lys Ala Ser Gly Tyr Thr Phe Thr Asn His
            20                  25                  30

Gly Ile Thr Trp Val Arg Gln Ala Pro Gly Gln Gly Leu Glu Trp Met
        35                  40                  45

Ser Trp Ile Ser Gly Tyr Asn Gly Asn Thr Gln Tyr Ala Gln Lys Phe
 50                  55                  60

Gln Gly Arg Val Thr Met Thr Thr Asp Thr Ser Thr Arg Thr Ala Tyr
 65                  70                  75                  80

Met Glu Leu Arg Ser Leu Thr Ser Asp Thr Ala Val Tyr Tyr Cys
                85                  90                  95

Ala Arg Asp Asn Gly Val Val Gly Pro Pro Asp Tyr Trp Gly Gln
            100                 105                 110

Gly Thr Leu Val Thr Val Ser Ser
            115                 120
```

<210> SEQ ID NO 34
<211> LENGTH: 106
<212> TYPE: PRT
<213> ORGANISM: Artificial sequence
<220> FEATURE:
<223> OTHER INFORMATION: Synthetic amino acid

<400> SEQUENCE: 34

```
Asp Ile Gln Met Thr Gln Ser Pro Ser Thr Leu Ser Ala Ser Val Gly
 1               5                  10                  15

Asp Arg Val Thr Ile Ser Cys Arg Ala Ser Gln Ser Ile Ser Ser Trp
            20                  25                  30

Leu Ala Trp Tyr Gln Gln Lys Pro Gly Lys Pro Pro Lys Leu Leu Ile
        35                  40                  45

Tyr Lys Ala Ser Gly Leu Gln Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Tyr Tyr His Ser Leu Ser Ala
                85                  90                  95

Phe Gly Gln Gly Thr Lys Val Glu Ile Lys
            100                 105
```

<210> SEQ ID NO 35
<211> LENGTH: 129
<212> TYPE: PRT
<213> ORGANISM: Artificial sequence
<220> FEATURE:
<223> OTHER INFORMATION: Synthetic amino acid

<400> SEQUENCE: 35

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Asp Ile Ser Ser Gly Gly Asp Thr Thr Tyr Tyr Ala Glu Ser Leu
 50                  55                  60

Lys Gly Arg Ile Thr Ile Ser Arg Asp Asn Ser Lys Asn Thr Leu Tyr
 65                  70                  75                  80

Leu Gln Met Asn Ser Leu Arg Ala Glu Asp Ala Ala Ile Tyr Phe Cys
```

```
                    85                  90                  95

Ala Lys His Leu Leu Ser Pro Met Tyr Val Asn Thr Asp Val Phe Pro
                100                 105                 110

Asp Trp Tyr Phe Glu Ile Trp Gly Arg Gly Thr Leu Val Thr Val Ser
            115                 120                 125

Ser

<210> SEQ ID NO 36

<400> SEQUENCE: 36

000

<210> SEQ ID NO 37
<211> LENGTH: 122
<212> TYPE: PRT
<213> ORGANISM: Artificial sequence
<220> FEATURE:
<223> OTHER INFORMATION: Synthetic amino acid

<400> SEQUENCE: 37

Gln Val Gln Leu Val Gln Ser Gly Thr Glu Val Lys Lys Pro Gly Thr
1               5                   10                  15

Ser Val Lys Val Ser Cys Lys Ala Ser Gly Tyr Ile Phe Ser Asn Tyr
                20                  25                  30

Gly Ile Ser Trp Val Arg Gln Ala Pro Gly Gln Gly Leu Glu Trp Met
            35                  40                  45

Gly Trp Ile Ser Val Tyr Asn Gly Asn Thr Asn Tyr Ala Gln Lys Phe
    50                  55                  60

Gln Gly Arg Val Thr Leu Thr Thr Asp Thr Ser Thr Asn Thr Ala Tyr
65                  70                  75                  80

Met Glu Val Arg Ser Leu Ser Ser Asp Asp Thr Ala Val Tyr Tyr Cys
                85                  90                  95

Ala Arg Glu Pro Pro Ser Leu Thr Ala Ala Gly Leu Leu Asp Tyr Trp
                100                 105                 110

Gly Gln Gly Thr Leu Val Thr Val Ser Ser
            115                 120

<210> SEQ ID NO 38
<211> LENGTH: 112
<212> TYPE: PRT
<213> ORGANISM: Artificial sequence
<220> FEATURE:
<223> OTHER INFORMATION: Synthetic amino acid

<400> SEQUENCE: 38

Gln Ala Val Val Thr Gln Ser Pro Leu Ser Leu Pro Val Thr Leu Gly
1               5                   10                  15

Gln Pro Ala Ser Ile Ser Cys Arg Ser Ser Gln Ser Pro Val Tyr Ser
                20                  25                  30

Asp Gly Asn Thr Tyr Leu Ser Trp Phe Gln Gln Arg Pro Gly Gln Ser
            35                  40                  45

Pro Arg Arg Leu Ile Tyr Lys Ile Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95
```

Thr His Trp Pro Arg Thr Phe Gly Gln Gly Thr Lys Val Glu Ile Lys
        100                 105                 110

<210> SEQ ID NO 39
<211> LENGTH: 123
<212> TYPE: PRT
<213> ORGANISM: Artificial sequence
<220> FEATURE:
<223> OTHER INFORMATION: Synthetic amino acid

<400> SEQUENCE: 39

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Ser Ile Thr Ser Ser Ser Tyr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Cys Gly Gly Asp Cys Ser Val Asp His Phe Gln His
            100                 105                 110

Trp Gly Gln Gly Thr Leu Val Thr Val Ser Ser
        115                 120

<210> SEQ ID NO 40
<211> LENGTH: 112
<212> TYPE: PRT
<213> ORGANISM: Artificial sequence
<220> FEATURE:
<223> OTHER INFORMATION: Synthetic amino acid

<400> SEQUENCE: 40

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln His Leu Pro Gly Thr Ala Pro Lys Leu
        35                  40                  45

Leu Ile Tyr Val Asn Ser Asn Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Lys Ser
                85                  90                  95

Leu Ser Gly Phe Tyr Val Phe Gly Thr Gly Thr Lys Val Thr Val Leu
            100                 105                 110

<210> SEQ ID NO 41
<211> LENGTH: 121
<212> TYPE: PRT
<213> ORGANISM: Artificial sequence
<220> FEATURE:
<223> OTHER INFORMATION: Synthetic amino acid

<400> SEQUENCE: 41

Gln Val Gln Leu Val Gln Ser Gly Ala Glu Val Lys Lys Pro Gly Thr

```
                1               5                  10                 15
Ser Val Arg Val Ser Cys Lys Thr Ser Gly Tyr Asn Phe Met Asn Tyr
                    20                  25                 30

Gly Ile Tyr Trp Val Arg Gln Ala Pro Gly Gln Gly Leu Glu Trp Val
            35                  40                 45

Gly Trp Ile Ser Ala Tyr Asn Gly Gln Thr Asp Arg Ala Gln Lys Phe
        50                  55                 60

Gln Gly Arg Val Thr Met Thr Thr Asp Ile Ser Thr Asn Thr Gly Tyr
65                  70                 75                  80

Met Asp Leu Arg Ser Leu Arg Ser Asp Thr Ala Val Tyr Phe Cys
                    85                  90                 95

Ala Arg Gly Pro Pro Val Ile Ala Ala Val Ser Leu Glu Tyr Trp Gly
                    100                 105                110

Arg Gly Thr Leu Val Thr Val Ser Ser
            115                 120
```

<210> SEQ ID NO 42
<211> LENGTH: 112
<212> TYPE: PRT
<213> ORGANISM: Artificial sequence
<220> FEATURE:
<223> OTHER INFORMATION: Synthetic amino acid

<400> SEQUENCE: 42

```
Glu Val Val Met Thr Gln Ser Pro Leu Ser Leu Pro Val Thr Leu Gly
1               5                  10                 15

Gln Pro Ala Ser Ile Ser Cys Lys Ser Ser Gln Ser Leu Val His Ser
                20                  25                 30

Asn Gly Asp Thr Tyr Leu Asn Trp Phe Gln Gln Arg Pro Gly Gln Ser
            35                  40                 45

Pro Arg Arg Leu Ile Tyr Lys Val Ser Asn Arg Asp Ser Gly Val Pro
        50                  55                 60

Asp Arg Phe Ser Gly Ser Gly Ser Gly Thr Asp Phe Thr Leu Lys Ile
65                  70                 75                  80

Ser Arg Val Glu Thr Glu Asp Val Gly Val Tyr Tyr Cys Met Gln Ala
                    85                  90                 95

Thr His Trp Pro Gly Ser Phe Gly Gln Gly Thr Lys Leu Glu Ile Lys
                    100                 105                110
```

<210> SEQ ID NO 43
<211> LENGTH: 119
<212> TYPE: PRT
<213> ORGANISM: Artificial sequence
<220> FEATURE:
<223> OTHER INFORMATION: Synthetic amino acid

<400> SEQUENCE: 43

```
Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Asn Tyr
                20                  25                 30

Tyr Met His Trp Val Arg Gln Ala Pro Gly Gln Gly Leu Glu Trp Met
            35                  40                 45

Gly Trp Ile Asn Pro Asn Arg Gly Gly Thr Asn Tyr Ala Gln Lys Phe
        50                  55                 60

Gln Gly Arg Val Thr Met Thr Leu Asp Thr Ser Ile Ser Thr Ala Tyr
65                  70                 75                  80
```

```
Ile Glu Leu Ser Arg Leu Arg Ser Asp Asp Thr Ala Val Tyr Tyr Cys
                85                  90                  95

Ala Arg Asp Leu Thr Leu Gly Thr Asp Tyr Trp Gly Gln Gly Thr Leu
            100                 105                 110

Val Thr Val Ser Ser Ala Ser
        115
```

<210> SEQ ID NO 44
<211> LENGTH: 110
<212> TYPE: PRT
<213> ORGANISM: Artificial sequence
<220> FEATURE:
<223> OTHER INFORMATION: Synthetic amino acid

<400> SEQUENCE: 44

```
Gln Ala Val Val Thr Gln Pro Ala Ser Val Phe Gly Phe Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Arg Pro Gly Lys Ala Pro Lys Leu
        35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Ser
                85                  90                  95

Asn Ser Tyr Val Phe Gly Thr Gly Thr Lys Val Thr Val Leu
            100                 105                 110
```

<210> SEQ ID NO 45
<211> LENGTH: 121
<212> TYPE: PRT
<213> ORGANISM: Artificial sequence
<220> FEATURE:
<223> OTHER INFORMATION: Synthetic amino acid

<400> SEQUENCE: 45

```
Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Thr Phe Ser Asn Tyr
            20                  25                  30

Gly Leu Ser Trp Val Arg Gln Ala Pro Gly Gln Gly Leu Glu Trp Met
        35                  40                  45

Gly Trp Ile Ser Asp Tyr Asn Gly Asn Thr Glu Tyr Ala Gln Lys Phe
50                  55                  60

Gln Gly Arg Val Thr Met Thr Thr Asp Arg Ser Thr Ser Thr Ala Tyr
65                  70                  75                  80

Met Glu Leu Lys Ser Leu Arg Ser Asp Asp Thr Ala Val Tyr Tyr Cys
                85                  90                  95

Ala Arg Asp Pro Pro Ala Ala Ala Ala Thr Tyr Asp Tyr Trp Gly
            100                 105                 110

Gln Gly Thr Leu Val Thr Val Ser Ser
        115                 120
```

<210> SEQ ID NO 46
<211> LENGTH: 108
<212> TYPE: PRT
<213> ORGANISM: Artificial sequence

```
<220> FEATURE:
<223> OTHER INFORMATION: Synthetic amino acid

<400> SEQUENCE: 46

Gln Thr Val Met Thr Gln Ser Pro Ser Leu Ser Ala Ser Ile Gly
1               5                   10                  15

Asp Arg Val Thr Ile Thr Cys Arg Val Ser Gln Gly Ile Ala Ser Tyr
            20                  25                  30

Leu Asn Trp Asn Arg Gln Lys Pro Gly Asn Phe Pro Lys Val Leu Met
        35                  40                  45

Gln Ser Ile Ser Asn Leu Gln Ser Gly Val Pro Ser Arg Phe Ser Gly
    50                  55                  60

Ser Gly Ser Gly Thr Asp Phe Thr Arg Thr Ile Ser Ser Leu Gln Pro
65                  70                  75                  80

Glu Asp Val Ala Thr Tyr Tyr Gly Arg Arg Thr Tyr Asn Ala Pro Leu
                85                  90                  95

Ala Leu Leu Ala Arg Gly Pro Thr Cys Arg Ser Asn
            100                 105

<210> SEQ ID NO 47
<211> LENGTH: 130
<212> TYPE: PRT
<213> ORGANISM: Artificial sequence
<220> FEATURE:
<223> OTHER INFORMATION: Synthetic amino acid

<400> SEQUENCE: 47

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Thr Thr Arg
            20                  25                  30

Gly Val Gly Val Ala Trp Ile Arg Gln Pro Pro Gly Lys Ala Leu Glu
        35                  40                  45

Trp Leu Ala Leu Ile Tyr Trp Asp Asp Lys Arg Tyr Arg Ser Ser
    50                  55                  60

Pro Lys Gly Arg Leu Thr Ile Thr Lys Asp Asn Ser Lys Asn Gln Val
65                  70                  75                  80

Val Leu Ile Met Thr Asn Met Asp Pro Val Asp Thr Ala Thr Tyr Tyr
                85                  90                  95

Cys Ala His Ala Met Asp Asp Ser Gly Ser Tyr Val Gly Leu Ser
            100                 105                 110

Lys Asp Pro His Phe Asp Ser Trp Gly His Gly Thr Leu Val Thr Val
        115                 120                 125

Ser Ser
    130

<210> SEQ ID NO 48
<211> LENGTH: 108
<212> TYPE: PRT
<213> ORGANISM: Artificial sequence
<220> FEATURE:
<223> OTHER INFORMATION: Synthetic amino acid

<400> SEQUENCE: 48

Ser Tyr Glu Leu Thr Gln Pro Pro Ser Val Ser Val Ser Pro Gly Gln
1               5                   10                  15

Thr Ala Ser Ile Thr Cys Ser Gly Asp Val Leu Phe Asn Lys Phe Ala
            20                  25                  30
```

Ser Trp Tyr Gln Gln Lys Pro Gly Gln Ser Pro Val Leu Val Ile Tyr
         35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Arg Gly Thr Gln Ala Met
65                   70                  75                  80

Asp Glu Ala Asp Tyr Tyr Cys Gln Ala Arg Gly Ser Thr Ala Ala His
                 85                  90                  95

Val Ile Phe Gly Gly Gly Thr Lys Val Thr Val Leu
            100                 105

<210> SEQ ID NO 49
<211> LENGTH: 121
<212> TYPE: PRT
<213> ORGANISM: Artificial sequence
<220> FEATURE:
<223> OTHER INFORMATION: Synthetic amino acid

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Ser Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Glu Phe Ala Gln Lys Phe
    50                  55                  60

Gln Gly Arg Ile Thr Met Thr Thr Asp Thr Ser Thr Asn Thr Ala Tyr
65                  70                  75                  80

Leu Glu Val Arg Gly Leu Arg Ser Asp Asp Thr Ala Val Tyr Tyr Cys
                85                  90                  95

Ser Arg Gln Ser Gly Val Ser Gly Val Pro Glu Phe Gln Asp Trp Gly
            100                 105                 110

Gln Gly Thr Leu Val Thr Val Ser Ser
        115                 120

<210> SEQ ID NO 50
<211> LENGTH: 113
<212> TYPE: PRT
<213> ORGANISM: Artificial sequence
<220> FEATURE:
<223> OTHER INFORMATION: Synthetic amino acid

<400> SEQUENCE: 50

Gln Ala Val Val Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asp Thr Tyr Leu Ser Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Ala Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Arg Leu Glu Ile
            100                 105                 110

Lys

```
<210> SEQ ID NO 51
<211> LENGTH: 124
<212> TYPE: PRT
<213> ORGANISM: Artificial sequence
<220> FEATURE:
<223> OTHER INFORMATION: Synthetic amino acid

<400> SEQUENCE: 51
```

Glu Val Gln Leu Val Glu Ser Gly Gly Thr Leu Val Gln Pro Gly Arg
1               5                   10                  15

Ser Leu Arg Leu Ser Cys Ala Ala Ser Gly Phe Asn Phe Glu Glu Tyr
            20                  25                  30

Ala Met His Trp Val Arg Gln Val Pro Gly Lys Gly Leu Glu Trp Val
        35                  40                  45

Ala Arg Ile Asn Trp Asn Gly Gly Ile Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Thr Asp Asp Ser Ala Leu Tyr Tyr Cys
                85                  90                  95

Gly Lys Asp Val Phe Trp Ala Val Ala Gly Thr Gly Gly Pro Ile Asp
            100                 105                 110

Ser Trp Gly Gln Gly Thr Leu Val Thr Val Ser Ser
        115                 120

```
<210> SEQ ID NO 52
<211> LENGTH: 108
<212> TYPE: PRT
<213> ORGANISM: Artificial sequence
<220> FEATURE:
<223> OTHER INFORMATION: Synthetic amino acid

<400> SEQUENCE: 52
```

Asp Ile Val Met Thr Gln Ser Pro Ser Ser Leu Ser Ala Ser Ile Gly
1               5                   10                  15

Asp Arg Val Thr Ile Ser Cys Arg Ala Ser Arg Asp Ile Ser Asn Tyr
            20                  25                  30

Leu Ala Trp Tyr Gln Gln Lys Ser Gly Lys Val Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Ala Gln Met
                85                  90                  95

Cys Ser Phe Gly Gln Gly Pro Ser Leu Glu Ile Lys
            100                 105

```
<210> SEQ ID NO 53
<211> LENGTH: 8
<212> TYPE: PRT
<213> ORGANISM: Artificial sequence
<220> FEATURE:
<223> OTHER INFORMATION: Synthetic amino acid

<400> SEQUENCE: 53
```

Gly Phe Thr Phe Asp Asp Tyr Thr

```
<210> SEQ ID NO 54
<211> LENGTH: 8
<212> TYPE: PRT
<213> ORGANISM: Artificial sequence
<220> FEATURE:
<223> OTHER INFORMATION: Synthetic amino acid

<400> SEQUENCE: 54

Ile Thr Trp Asn Ser Gly Tyr Ile
1               5

<210> SEQ ID NO 55
<211> LENGTH: 18
<212> TYPE: PRT
<213> ORGANISM: Artificial sequence
<220> FEATURE:
<223> OTHER INFORMATION: Synthetic amino acid

<400> SEQUENCE: 55

Val Arg Asp Ala Tyr Val Ser Gly Ser Asp Tyr Tyr Tyr Gly Leu
1               5                   10                  15

Asp Val

<210> SEQ ID NO 56
<211> LENGTH: 8
<212> TYPE: PRT
<213> ORGANISM: Artificial sequence
<220> FEATURE:
<223> OTHER INFORMATION: Synthetic amino acid

<400> SEQUENCE: 56

Gly Phe Thr Phe Asp Asp Tyr Ala
1               5

<210> SEQ ID NO 57
<211> LENGTH: 8
<212> TYPE: PRT
<213> ORGANISM: Artificial sequence
<220> FEATURE:
<223> OTHER INFORMATION: Synthetic amino acid

<400> SEQUENCE: 57

Ile Ser Trp Asn Ser Gly Ile Ala
1               5

<210> SEQ ID NO 58
<211> LENGTH: 21
<212> TYPE: PRT
<213> ORGANISM: Artificial sequence
<220> FEATURE:
<223> OTHER INFORMATION: Synthetic amino acid

<400> SEQUENCE: 58

Val Lys Asp Asn Tyr Ala Ser Gly Ser Tyr Ser Ser Tyr Tyr Tyr
1               5                   10                  15

Tyr Gly Leu Asp Leu
            20

<210> SEQ ID NO 59
<211> LENGTH: 8
<212> TYPE: PRT
<213> ORGANISM: Artificial sequence
<220> FEATURE:
<223> OTHER INFORMATION: Synthetic amino acid
```

<400> SEQUENCE: 59

Gly Phe Arg Phe Asp Asp Tyr Ala
1               5

<210> SEQ ID NO 60
<211> LENGTH: 8
<212> TYPE: PRT
<213> ORGANISM: Artificial sequence
<220> FEATURE:
<223> OTHER INFORMATION: Synthetic amino acid

<400> SEQUENCE: 60

Ile Ser Trp His Ser Gly His Arg
1               5

<210> SEQ ID NO 61
<211> LENGTH: 19
<212> TYPE: PRT
<213> ORGANISM: Artificial sequence
<220> FEATURE:
<223> OTHER INFORMATION: Synthetic amino acid

<400> SEQUENCE: 61

Val Lys Asp Ser His Tyr Phe Asp Asn Ser Gly Ser Tyr Thr Tyr Gly
1               5                   10                  15

Leu Asp Val

<210> SEQ ID NO 62
<211> LENGTH: 8
<212> TYPE: PRT
<213> ORGANISM: Artificial sequence
<220> FEATURE:
<223> OTHER INFORMATION: Synthetic amino acid

<400> SEQUENCE: 62

Gly Tyr Thr Phe Thr Asn His Gly
1               5

<210> SEQ ID NO 63
<211> LENGTH: 8
<212> TYPE: PRT
<213> ORGANISM: Artificial sequence
<220> FEATURE:
<223> OTHER INFORMATION: Synthetic amino acid

<400> SEQUENCE: 63

Ile Ser Gly Tyr Asn Gly Asn Thr
1               5

<210> SEQ ID NO 64
<211> LENGTH: 13
<212> TYPE: PRT
<213> ORGANISM: Artificial sequence
<220> FEATURE:
<223> OTHER INFORMATION: Synthetic amino acid

<400> SEQUENCE: 64

Ala Arg Asp Asn Gly Val Val Val Gly Pro Pro Asp Tyr
1               5                   10

<210> SEQ ID NO 65
<211> LENGTH: 8
<212> TYPE: PRT
<213> ORGANISM: Artificial sequence
<220> FEATURE:

```
<223> OTHER INFORMATION: Synthetic amino acid

<400> SEQUENCE: 65

Gly Phe Thr Phe Arg Asn Tyr Ala
1               5

<210> SEQ ID NO 66
<211> LENGTH: 8
<212> TYPE: PRT
<213> ORGANISM: Artificial sequence
<220> FEATURE:
<223> OTHER INFORMATION: Synthetic amino acid

<400> SEQUENCE: 66

Ile Ser Ser Gly Gly Asp Thr Thr
1               5

<210> SEQ ID NO 67
<211> LENGTH: 22
<212> TYPE: PRT
<213> ORGANISM: Artificial sequence
<220> FEATURE:
<223> OTHER INFORMATION: Synthetic amino acid

<400> SEQUENCE: 67

Ala Lys His Leu Leu Ser Pro Met Tyr Val Asn Thr Asp Val Phe Pro
1               5                   10                  15

Asp Trp Tyr Phe Glu Ile
            20

<210> SEQ ID NO 68
<211> LENGTH: 8
<212> TYPE: PRT
<213> ORGANISM: Artificial sequence
<220> FEATURE:
<223> OTHER INFORMATION: Synthetic amino acid

<400> SEQUENCE: 68

Gly Tyr Ile Phe Ser Asn Tyr Gly
1               5

<210> SEQ ID NO 69
<211> LENGTH: 8
<212> TYPE: PRT
<213> ORGANISM: Artificial sequence
<220> FEATURE:
<223> OTHER INFORMATION: Synthetic amino acid

<400> SEQUENCE: 69

Ile Ser Val Tyr Asn Gly Asn Thr
1               5

<210> SEQ ID NO 70
<211> LENGTH: 15
<212> TYPE: PRT
<213> ORGANISM: Artificial sequence
<220> FEATURE:
<223> OTHER INFORMATION: Synthetic amino acid

<400> SEQUENCE: 70

Ala Arg Glu Pro Pro Ser Leu Thr Ala Ala Gly Leu Leu Asp Tyr
1               5                   10                  15

<210> SEQ ID NO 71
<211> LENGTH: 8
<212> TYPE: PRT
```

<213> ORGANISM: Artificial sequence
<220> FEATURE:
<223> OTHER INFORMATION: Synthetic amino acid

<400> SEQUENCE: 71

Gly Phe Thr Phe Arg Ser Tyr Ser
1               5

<210> SEQ ID NO 72
<211> LENGTH: 8
<212> TYPE: PRT
<213> ORGANISM: Artificial sequence
<220> FEATURE:
<223> OTHER INFORMATION: Synthetic amino acid

<400> SEQUENCE: 72

Ile Thr Ser Ser Ser Ser Tyr Ile
1               5

<210> SEQ ID NO 73
<211> LENGTH: 16
<212> TYPE: PRT
<213> ORGANISM: Artificial sequence
<220> FEATURE:
<223> OTHER INFORMATION: Synthetic amino acid

<400> SEQUENCE: 73

Ala Arg Ala Tyr Cys Gly Gly Asp Cys Ser Val Asp His Phe Gln His
1               5                   10                  15

<210> SEQ ID NO 74
<211> LENGTH: 8
<212> TYPE: PRT
<213> ORGANISM: Artificial sequence
<220> FEATURE:
<223> OTHER INFORMATION: Synthetic amino acid

<400> SEQUENCE: 74

Gly Tyr Asn Phe Met Asn Tyr Gly
1               5

<210> SEQ ID NO 75
<211> LENGTH: 8
<212> TYPE: PRT
<213> ORGANISM: Artificial sequence
<220> FEATURE:
<223> OTHER INFORMATION: Synthetic amino acid

<400> SEQUENCE: 75

Ile Ser Ala Tyr Asn Gly Gln Thr
1               5

<210> SEQ ID NO 76
<211> LENGTH: 14
<212> TYPE: PRT
<213> ORGANISM: Artificial sequence
<220> FEATURE:
<223> OTHER INFORMATION: Synthetic amino acid

<400> SEQUENCE: 76

Ala Arg Gly Pro Pro Val Ile Ala Ala Val Ser Leu Glu Tyr
1               5                   10

<210> SEQ ID NO 77
<211> LENGTH: 8
<212> TYPE: PRT
<213> ORGANISM: Artificial sequence

```
<220> FEATURE:
<223> OTHER INFORMATION: Synthetic amino acid

<400> SEQUENCE: 77

Gly Tyr Thr Phe Thr Asn Tyr Tyr
1               5

<210> SEQ ID NO 78
<211> LENGTH: 8
<212> TYPE: PRT
<213> ORGANISM: Artificial sequence
<220> FEATURE:
<223> OTHER INFORMATION: Synthetic amino acid

<400> SEQUENCE: 78

Ile Asn Pro Asn Arg Gly Gly Thr
1               5

<210> SEQ ID NO 79
<211> LENGTH: 10
<212> TYPE: PRT
<213> ORGANISM: Artificial sequence
<220> FEATURE:
<223> OTHER INFORMATION: Synthetic amino acid

<400> SEQUENCE: 79

Ala Arg Asp Leu Thr Leu Gly Thr Asp Tyr
1               5                   10

<210> SEQ ID NO 80
<211> LENGTH: 8
<212> TYPE: PRT
<213> ORGANISM: Artificial sequence
<220> FEATURE:
<223> OTHER INFORMATION: Synthetic amino acid

<400> SEQUENCE: 80

Gly Tyr Thr Phe Ser Asn Tyr Gly
1               5

<210> SEQ ID NO 81
<211> LENGTH: 8
<212> TYPE: PRT
<213> ORGANISM: Artificial sequence
<220> FEATURE:
<223> OTHER INFORMATION: Synthetic amino acid

<400> SEQUENCE: 81

Ile Ser Asp Tyr Asn Gly Asn Thr
1               5

<210> SEQ ID NO 82
<211> LENGTH: 14
<212> TYPE: PRT
<213> ORGANISM: Artificial sequence
<220> FEATURE:
<223> OTHER INFORMATION: Synthetic amino acid

<400> SEQUENCE: 82

Ala Arg Asp Pro Pro Ala Ala Ala Ala Ala Thr Tyr Asp Tyr
1               5                   10

<210> SEQ ID NO 83
<211> LENGTH: 10
<212> TYPE: PRT
<213> ORGANISM: Artificial sequence
<220> FEATURE:
```

```
<223> OTHER INFORMATION: Synthetic amino acid

<400> SEQUENCE: 83

Gly Phe Ser Leu Thr Thr Arg Gly Val Gly
1               5                   10

<210> SEQ ID NO 84
<211> LENGTH: 7
<212> TYPE: PRT
<213> ORGANISM: Artificial sequence
<220> FEATURE:
<223> OTHER INFORMATION: Synthetic amino acid

<400> SEQUENCE: 84

Ile Tyr Trp Asp Asp Asp Lys
1               5

<210> SEQ ID NO 85
<211> LENGTH: 22
<212> TYPE: PRT
<213> ORGANISM: Artificial sequence
<220> FEATURE:
<223> OTHER INFORMATION: Synthetic amino acid

<400> SEQUENCE: 85

Ala His Ala Met Asp Asp Ser Gly Ser Tyr Tyr Val Gly Leu Ser Lys
1               5                   10                  15

Asp Pro His Phe Asp Ser
            20

<210> SEQ ID NO 86
<211> LENGTH: 8
<212> TYPE: PRT
<213> ORGANISM: Artificial sequence
<220> FEATURE:
<223> OTHER INFORMATION: Synthetic amino acid

<400> SEQUENCE: 86

Gly Tyr Val Phe Ser Asn Tyr Gly
1               5

<210> SEQ ID NO 87
<211> LENGTH: 8
<212> TYPE: PRT
<213> ORGANISM: Artificial sequence
<220> FEATURE:
<223> OTHER INFORMATION: Synthetic amino acid

<400> SEQUENCE: 87

Ile Ser Ala Tyr Asn Gly Asn Thr
1               5

<210> SEQ ID NO 88
<211> LENGTH: 14
<212> TYPE: PRT
<213> ORGANISM: Artificial sequence
<220> FEATURE:
<223> OTHER INFORMATION: Synthetic amino acid

<400> SEQUENCE: 88

Ser Arg Gln Ser Gly Val Ser Gly Val Pro Glu Phe Gln Asp
1               5                   10

<210> SEQ ID NO 89
<211> LENGTH: 8
<212> TYPE: PRT
```

<213> ORGANISM: Artificial sequence
<220> FEATURE:
<223> OTHER INFORMATION: Synthetic amino acid

<400> SEQUENCE: 89

Gly Phe Asn Phe Glu Glu Tyr Ala
1               5

<210> SEQ ID NO 90
<211> LENGTH: 8
<212> TYPE: PRT
<213> ORGANISM: Artificial sequence
<220> FEATURE:
<223> OTHER INFORMATION: Synthetic amino acid

<400> SEQUENCE: 90

Ile Asn Trp Asn Gly Gly Ile Ile
1               5

<210> SEQ ID NO 91
<211> LENGTH: 17
<212> TYPE: PRT
<213> ORGANISM: Artificial sequence
<220> FEATURE:
<223> OTHER INFORMATION: Synthetic amino acid

<400> SEQUENCE: 91

Gly Lys Asp Val Phe Trp Ala Val Ala Gly Thr Gly Gly Pro Ile Asp
1               5                   10                  15

Ser

<210> SEQ ID NO 92
<211> LENGTH: 6
<212> TYPE: PRT
<213> ORGANISM: Artificial sequence
<220> FEATURE:
<223> OTHER INFORMATION: Synthetic amino acid

<400> SEQUENCE: 92

Gln Ser Val Ile Ser Asn
1               5

<210> SEQ ID NO 93
<211> LENGTH: 3
<212> TYPE: PRT
<213> ORGANISM: Artificial sequence
<220> FEATURE:
<223> OTHER INFORMATION: Synthetic amino acid

<400> SEQUENCE: 93

Gly Ala Ser
1

<210> SEQ ID NO 94
<211> LENGTH: 9
<212> TYPE: PRT
<213> ORGANISM: Artificial sequence
<220> FEATURE:
<223> OTHER INFORMATION: Synthetic amino acid

<400> SEQUENCE: 94

Gln Gln Tyr Asn Asn Trp Pro Leu Thr
1               5

<210> SEQ ID NO 95
<211> LENGTH: 6

```
<212> TYPE: PRT
<213> ORGANISM: Artificial sequence
<220> FEATURE:
<223> OTHER INFORMATION: Synthetic amino acid

<400> SEQUENCE: 95

Gln Ser Ile Ile Ser Asn
1               5

<210> SEQ ID NO 96
<211> LENGTH: 3
<212> TYPE: PRT
<213> ORGANISM: Artificial sequence
<220> FEATURE:
<223> OTHER INFORMATION: Synthetic amino acid

<400> SEQUENCE: 96

Gly Val Ser
1

<210> SEQ ID NO 97
<211> LENGTH: 9
<212> TYPE: PRT
<213> ORGANISM: Artificial sequence
<220> FEATURE:
<223> OTHER INFORMATION: Synthetic amino acid

<400> SEQUENCE: 97

Gln Gln Tyr Asn Asn Trp Pro Ile Thr
1               5

<210> SEQ ID NO 98
<211> LENGTH: 6
<212> TYPE: PRT
<213> ORGANISM: Artificial sequence
<220> FEATURE:
<223> OTHER INFORMATION: Synthetic amino acid

<400> SEQUENCE: 98

Gln Ser Val Leu Ser Asn
1               5

<210> SEQ ID NO 99
<211> LENGTH: 3
<212> TYPE: PRT
<213> ORGANISM: Artificial sequence
<220> FEATURE:
<223> OTHER INFORMATION: Synthetic amino acid

<400> SEQUENCE: 99

Gly Ala Ser
1

<210> SEQ ID NO 100
<211> LENGTH: 9
<212> TYPE: PRT
<213> ORGANISM: Artificial sequence
<220> FEATURE:
<223> OTHER INFORMATION: Synthetic amino acid

<400> SEQUENCE: 100

Gln Gln Tyr Asn Asn Trp Pro Leu Thr
1               5

<210> SEQ ID NO 101
<211> LENGTH: 6
<212> TYPE: PRT
```

<213> ORGANISM: Artificial sequence
<220> FEATURE:
<223> OTHER INFORMATION: Synthetic amino acid

<400> SEQUENCE: 101

Gln Ser Ile Ser Ser Trp
1               5

<210> SEQ ID NO 102
<211> LENGTH: 3
<212> TYPE: PRT
<213> ORGANISM: Artificial sequence
<220> FEATURE:
<223> OTHER INFORMATION: Synthetic amino acid

<400> SEQUENCE: 102

Lys Ala Ser
1

<210> SEQ ID NO 103
<211> LENGTH: 8
<212> TYPE: PRT
<213> ORGANISM: Artificial sequence
<220> FEATURE:
<223> OTHER INFORMATION: Synthetic amino acid

<400> SEQUENCE: 103

Gln Tyr Tyr His Ser Leu Ser Ala
1               5

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107
<211> LENGTH: 11
<212> TYPE: PRT
<213> ORGANISM: Artificial sequence
<220> FEATURE:
<223> OTHER INFORMATION: Synthetic amino acid

<400> SEQUENCE: 107

Gln Ser Pro Val Tyr Ser Asp Gly Asn Thr Tyr
1               5                   10

<210> SEQ ID NO 108
<211> LENGTH: 3
<212> TYPE: PRT
<213> ORGANISM: Artificial sequence
<220> FEATURE:
<223> OTHER INFORMATION: Synthetic amino acid

<400> SEQUENCE: 108

Gly Ala Ser
1

<210> SEQ ID NO 109
<211> LENGTH: 9
<212> TYPE: PRT
<213> ORGANISM: Artificial sequence
<220> FEATURE:
<223> OTHER INFORMATION: Synthetic amino acid

<400> SEQUENCE: 109

Gln Gln Tyr Asn Asn Trp Pro Leu Thr
1               5

<210> SEQ ID NO 110
<211> LENGTH: 9
<212> TYPE: PRT
<213> ORGANISM: Artificial sequence
<220> FEATURE:
<223> OTHER INFORMATION: Synthetic amino acid

<400> SEQUENCE: 110

Ser Ser Asn Ile Gly Ala Gly Tyr Asp
1               5

<210> SEQ ID NO 111
<211> LENGTH: 3
<212> TYPE: PRT
<213> ORGANISM: Artificial sequence
<220> FEATURE:
<223> OTHER INFORMATION: Synthetic amino acid

<400> SEQUENCE: 111

Val Asn Ser
1

<210> SEQ ID NO 112
<211> LENGTH: 12
<212> TYPE: PRT
<213> ORGANISM: Artificial sequence
<220> FEATURE:
<223> OTHER INFORMATION: Synthetic amino acid

<400> SEQUENCE: 112

Gln Ser Tyr Asp Lys Ser Leu Ser Gly Phe Tyr Val
1               5                   10

<210> SEQ ID NO 113
<211> LENGTH: 11
<212> TYPE: PRT
<213> ORGANISM: Artificial sequence
<220> FEATURE:
<223> OTHER INFORMATION: Synthetic amino acid

<400> SEQUENCE: 113

Gln Ser Leu Val His Ser Asn Gly Asp Thr Tyr
1               5                   10

<210> SEQ ID NO 114
<211> LENGTH: 3
<212> TYPE: PRT
<213> ORGANISM: Artificial sequence
<220> FEATURE:
<223> OTHER INFORMATION: Synthetic amino acid

<400> SEQUENCE: 114

Lys Val Ser

```
<210> SEQ ID NO 115
<211> LENGTH: 9
<212> TYPE: PRT
<213> ORGANISM: Artificial sequence
<220> FEATURE:
<223> OTHER INFORMATION: Synthetic amino acid

<400> SEQUENCE: 115

Met Gln Ala Thr His Trp Pro Gly Ser
1               5

<210> SEQ ID NO 116
<211> LENGTH: 9
<212> TYPE: PRT
<213> ORGANISM: Artificial sequence
<220> FEATURE:
<223> OTHER INFORMATION: Synthetic amino acid

<400> SEQUENCE: 116

Ser Ser Asp Val Gly Gly Tyr Lys Tyr
1               5

<210> SEQ ID NO 117
<211> LENGTH: 3
<212> TYPE: PRT
<213> ORGANISM: Artificial sequence
<220> FEATURE:
<223> OTHER INFORMATION: Synthetic amino acid

<400> SEQUENCE: 117

Glu Val Ser
1

<210> SEQ ID NO 118
<211> LENGTH: 10
<212> TYPE: PRT
<213> ORGANISM: Artificial sequence
<220> FEATURE:
<223> OTHER INFORMATION: Synthetic amino acid

<400> SEQUENCE: 118

Asn Ser Tyr Thr Ser Ser Asn Ser Tyr Val
1               5                   10

<210> SEQ ID NO 119
<211> LENGTH: 6
<212> TYPE: PRT
<213> ORGANISM: Artificial sequence
<220> FEATURE:
<223> OTHER INFORMATION: Synthetic amino acid

<400> SEQUENCE: 119

Gln Gly Ile Ala Ser Tyr
1               5

<210> SEQ ID NO 120
<211> LENGTH: 3
<212> TYPE: PRT
<213> ORGANISM: Artificial sequence
<220> FEATURE:
<223> OTHER INFORMATION: Synthetic amino acid

<400> SEQUENCE: 120

Ser Ile Ser
1
```

```
<210> SEQ ID NO 121
<211> LENGTH: 9
<212> TYPE: PRT
<213> ORGANISM: Artificial sequence
<220> FEATURE:
<223> OTHER INFORMATION: Synthetic amino acid

<400> SEQUENCE: 121

Arg Arg Thr Tyr Asn Ala Pro Leu Ala
1               5

<210> SEQ ID NO 122
<211> LENGTH: 6
<212> TYPE: PRT
<213> ORGANISM: Artificial sequence
<220> FEATURE:
<223> OTHER INFORMATION: Synthetic amino acid

<400> SEQUENCE: 122

Val Leu Phe Asn Lys Phe
1               5

<210> SEQ ID NO 123
<211> LENGTH: 3
<212> TYPE: PRT
<213> ORGANISM: Artificial sequence
<220> FEATURE:
<223> OTHER INFORMATION: Synthetic amino acid

<400> SEQUENCE: 123

Gln Asp Ser
1

<210> SEQ ID NO 124
<211> LENGTH: 11
<212> TYPE: PRT
<213> ORGANISM: Artificial sequence
<220> FEATURE:
<223> OTHER INFORMATION: Synthetic amino acid

<400> SEQUENCE: 124

Gln Ala Arg Gly Ser Thr Ala Ala His Val Ile
1               5                   10

<210> SEQ ID NO 125
<211> LENGTH: 11
<212> TYPE: PRT
<213> ORGANISM: Artificial sequence
<220> FEATURE:
<223> OTHER INFORMATION: Synthetic amino acid

<400> SEQUENCE: 125

Gln Ser Leu Val Tyr Ser Asn Gly Asp Thr Tyr
1               5                   10

<210> SEQ ID NO 126
<211> LENGTH: 3
<212> TYPE: PRT
<213> ORGANISM: Artificial sequence
<220> FEATURE:
<223> OTHER INFORMATION: Synthetic amino acid

<400> SEQUENCE: 126

Lys Val Ser
1
```

<210> SEQ ID NO 127
<211> LENGTH: 10
<212> TYPE: PRT
<213> ORGANISM: Artificial sequence
<220> FEATURE:
<223> OTHER INFORMATION: Synthetic amino acid

<400> SEQUENCE: 127

Met Gln Gly Thr His Trp Pro Pro Pro Thr
1               5                   10

<210> SEQ ID NO 128
<211> LENGTH: 6
<212> TYPE: PRT
<213> ORGANISM: Artificial sequence
<220> FEATURE:
<223> OTHER INFORMATION: Synthetic amino acid

<400> SEQUENCE: 128

Arg Asp Ile Ser Asn Tyr
1               5

<210> SEQ ID NO 129
<211> LENGTH: 3
<212> TYPE: PRT
<213> ORGANISM: Artificial sequence
<220> FEATURE:
<223> OTHER INFORMATION: Synthetic amino acid

<400> SEQUENCE: 129

Ala Ala Ser
1

<210> SEQ ID NO 130
<211> LENGTH: 10
<212> TYPE: PRT
<213> ORGANISM: Artificial sequence
<220> FEATURE:
<223> OTHER INFORMATION: Synthetic amino acid

<400> SEQUENCE: 130

Gln Asn Tyr Asn Ser Ala Gln Met Cys Ser
1               5                   10

<210> SEQ ID NO 131
<211> LENGTH: 16
<212> TYPE: PRT
<213> ORGANISM: Artificial sequence
<220> FEATURE:
<223> OTHER INFORMATION: Synthetic amino acid

<400> SEQUENCE: 131

Cys Ala Arg Gly Pro Pro Val Ile Ala Ala Val Ser Leu Glu Tyr Trp
1               5                   10                  15

<210> SEQ ID NO 132
<211> LENGTH: 11
<212> TYPE: PRT
<213> ORGANISM: Artificial sequence
<220> FEATURE:
<223> OTHER INFORMATION: Synthetic amino acid

<400> SEQUENCE: 132

Cys Met Gln Ala Thr His Trp Pro Gly Ser Phe
1               5                   10

```
<210> SEQ ID NO 133
<211> LENGTH: 17
<212> TYPE: PRT
<213> ORGANISM: Artificial sequence
<220> FEATURE:
<223> OTHER INFORMATION: Synthetic amino acid

<400> SEQUENCE: 133

Cys Ala Arg Glu Pro Pro Ser Leu Thr Ala Ala Gly Leu Leu Asp Tyr
1               5                   10                  15
Trp

<210> SEQ ID NO 134
<211> LENGTH: 11
<212> TYPE: PRT
<213> ORGANISM: Artificial sequence
<220> FEATURE:
<223> OTHER INFORMATION: Synthetic amino acid

<400> SEQUENCE: 134

Cys Gln Gln Tyr Asn Asn Trp Pro Leu Thr Phe
1               5                   10

<210> SEQ ID NO 135
<211> LENGTH: 15
<212> TYPE: PRT
<213> ORGANISM: Artificial sequence
<220> FEATURE:
<223> OTHER INFORMATION: Synthetic amino acid

<400> SEQUENCE: 135

Cys Ala Arg Asp Asn Gly Val Val Val Gly Pro Pro Asp Tyr Trp
1               5                   10                  15

<210> SEQ ID NO 136
<211> LENGTH: 10
<212> TYPE: PRT
<213> ORGANISM: Artificial sequence
<220> FEATURE:
<223> OTHER INFORMATION: Synthetic amino acid

<400> SEQUENCE: 136

Cys Gln Tyr Tyr His Ser Leu Ser Ala Phe
1               5                   10

<210> SEQ ID NO 137
<211> LENGTH: 16
<212> TYPE: PRT
<213> ORGANISM: Artificial sequence
<220> FEATURE:
<223> OTHER INFORMATION: Synthetic amino acid

<400> SEQUENCE: 137

Cys Ser Arg Gln Ser Gly Val Ser Gly Val Pro Glu Phe Gln Asp Trp
1               5                   10                  15

<210> SEQ ID NO 138
<211> LENGTH: 12
<212> TYPE: PRT
<213> ORGANISM: Artificial sequence
<220> FEATURE:
<223> OTHER INFORMATION: Synthetic amino acid

<400> SEQUENCE: 138

Cys Met Gln Gly Thr His Trp Pro Pro Pro Thr Phe
1               5                   10
```

```
<210> SEQ ID NO 139
<211> LENGTH: 20
<212> TYPE: PRT
<213> ORGANISM: Artificial sequence
<220> FEATURE:
<223> OTHER INFORMATION: Synthetic amino acid

<400> SEQUENCE: 139

Cys Val Arg Asp Ala Tyr Val Ser Gly Ser Asp Tyr Tyr Tyr Tyr Gly
1               5                   10                  15

Leu Asp Val Trp
            20

<210> SEQ ID NO 140
<211> LENGTH: 11
<212> TYPE: PRT
<213> ORGANISM: Artificial sequence
<220> FEATURE:
<223> OTHER INFORMATION: Synthetic amino acid

<400> SEQUENCE: 140

Cys Gln Gln Tyr Asn Asn Trp Pro Leu Thr Phe
1               5                   10

<210> SEQ ID NO 141
<211> LENGTH: 23
<212> TYPE: PRT
<213> ORGANISM: Artificial sequence
<220> FEATURE:
<223> OTHER INFORMATION: Synthetic amino acid

<400> SEQUENCE: 141

Cys Val Lys Asp Asn Tyr Ala Ser Gly Ser Tyr Ser Ser Tyr Tyr Tyr
1               5                   10                  15

Tyr Tyr Gly Leu Asp Leu Trp
            20

<210> SEQ ID NO 142
<211> LENGTH: 11
<212> TYPE: PRT
<213> ORGANISM: Artificial sequence
<220> FEATURE:
<223> OTHER INFORMATION: Synthetic amino acid

<400> SEQUENCE: 142

Cys Gln Gln Tyr Asn Asn Trp Pro Ile Thr Phe
1               5                   10

<210> SEQ ID NO 143
<211> LENGTH: 21
<212> TYPE: PRT
<213> ORGANISM: Artificial sequence
<220> FEATURE:
<223> OTHER INFORMATION: Synthetic amino acid

<400> SEQUENCE: 143

Cys Val Lys Asp Ser His Tyr Phe Asp Asn Ser Gly Ser Tyr Thr Tyr
1               5                   10                  15

Gly Leu Asp Val Trp
            20

<210> SEQ ID NO 144
<211> LENGTH: 11
<212> TYPE: PRT
<213> ORGANISM: Artificial sequence
```

```
<220> FEATURE:
<223> OTHER INFORMATION: Synthetic amino acid

<400> SEQUENCE: 144

Cys Gln Gln Tyr Asn Asn Trp Pro Leu Thr Phe
1               5                   10

<210> SEQ ID NO 145
<211> LENGTH: 19
<212> TYPE: PRT
<213> ORGANISM: Artificial sequence
<220> FEATURE:
<223> OTHER INFORMATION: Synthetic amino acid

<400> SEQUENCE: 145

Cys Gly Lys Asp Val Phe Trp Ala Val Ala Gly Thr Gly Gly Pro Ile
1               5                   10                  15

Asp Ser Trp

<210> SEQ ID NO 146
<211> LENGTH: 12
<212> TYPE: PRT
<213> ORGANISM: Artificial sequence
<220> FEATURE:
<223> OTHER INFORMATION: Synthetic amino acid

<400> SEQUENCE: 146

Cys Gln Asn Tyr Asn Ser Ala Gln Met Cys Ser Phe
1               5                   10

<210> SEQ ID NO 147
<211> LENGTH: 574
<212> TYPE: PRT
<213> ORGANISM: Artificial sequence
<220> FEATURE:
<223> OTHER INFORMATION: Synthetic polypeptide

<400> SEQUENCE: 147

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175
```

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Cys Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Gly Pro Ser Asp Glu Phe Asp Ala Ser Ile Ser Gln Val Asn
                485                 490                 495

Glu Lys Ile Asn Gln Ser Leu Ala Phe Ile Arg Lys Ser Asn Glu Leu
            500                 505                 510

Leu His Asn Val Asn Ala Val Lys Ser Thr Thr Asn Ile Met Ile Thr
        515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 148
<211> LENGTH: 574
<212> TYPE: PRT

<213> ORGANISM: Artificial sequence
<220> FEATURE:
<223> OTHER INFORMATION: Synthetic polypeptide

<400> SEQUENCE: 148

```
Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Arg Leu Leu Pro Ile Val Asn
        195                 200                 205

Gln Gln Ser Cys Arg Ile Ser Asn Ile Glu Thr Val Ile Glu Phe Gln
210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
```

-continued

```
385                 390                 395                 400

Asp Ile Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Cys Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Gly Pro Ser Asp Glu Phe Asp Ala Ser Ile Ser Gln Val Asn
            485                 490                 495

Glu Lys Ile Asn Gln Ser Leu Ala Phe Ile Arg Arg Ser Asn Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
            565                 570
```